United States Patent
Asako

(10) Patent No.: US 10,351,829 B2
(45) Date of Patent: Jul. 16, 2019

(54) OXIDASE, POLYNUCLEOTIDE THAT CODES FOR SAME, AND USE THEREOF

(71) Applicant: Sumitomo Chemical Company, Chuo-ku, Tokyo (JP)

(72) Inventor: Hiroyuki Asako, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/325,287

(22) PCT Filed: Jul. 2, 2015

(86) PCT No.: PCT/JP2015/069106
§ 371 (c)(1),
(2) Date: Jan. 10, 2017

(87) PCT Pub. No.: WO2016/006522
PCT Pub. Date: Jan. 14, 2016

(65) Prior Publication Data
US 2017/0159029 A1    Jun. 8, 2017

(30) Foreign Application Priority Data

Jul. 11, 2014 (JP) ................. 2014-143022

(51) Int. Cl.
| | | |
|---|---|---|
| *C12N 9/04* | (2006.01) | |
| *C12N 9/06* | (2006.01) | |
| *C12N 1/21* | (2006.01) | |
| *C12P 13/04* | (2006.01) | |
| *C12P 13/06* | (2006.01) | |
| *C12P 13/12* | (2006.01) | |
| *C12N 5/10* | (2006.01) | |
| *C12N 15/09* | (2006.01) | |

(52) U.S. Cl.
CPC ............ *C12N 9/0006* (2013.01); *C12N 5/10* (2013.01); *C12N 9/0016* (2013.01); *C12N 15/09* (2013.01); *C12P 13/04* (2013.01); *C12P 13/06* (2013.01); *C12P 13/12* (2013.01); *C12Y 104/01009* (2013.01); *C07K 2319/21* (2013.01)

(58) Field of Classification Search
None
See application file for complete search history.

(56) References Cited

U.S. PATENT DOCUMENTS

| 4,782,020 A | 11/1988 | Leuchtenberger et al. |
| 4,824,781 A | 4/1989 | Hummel et al. |
| 2011/0281309 A1 | 11/2011 | Kanamaru et al. |

FOREIGN PATENT DOCUMENTS

| JP | S55-102557 A | 8/1980 |
| JP | S62-100286 A | 5/1987 |
| WO | 2012036302 A1 | 3/2012 |

OTHER PUBLICATIONS

Achromobacter denitrificans (ATCC 55564), Product Sheet, American Type Culture Collection, 2012.*
Guo et al., Protein tolerance to random amino acid change, Proc. Natl. Acad. Sci. USA , 2004,101, 9205-10.*
Langer et al., Conversion of the alpha-hydroxy and alpha-keto analogues of methionine to methionine by cell-free extracts of adult female Ascaris suum, J. Parasitology, 1971, 57, 836-39.*
Dengler et al., Crystal structure of a ternary complex of D-2-hydroxy-isocaproate dehydrogenase form Lactobacillus casei, J. Mol. Biol., 1997, 267, 640-60.*
Wilms et al., Development of an *Escherichia coli* whole cell biocatalyst for production of L-amino acids, J. Biotechnol., 2001, 86, 19-30.*
Uniprot, Accession No. A0A1Z3HDY2, 2017, www.uniprot.org.*
Uniprot, Accession No. A0A1Z3H3V4, 2017, www.uniprot.org.*
Extended Search Report dated Feb. 9, 2018 in EP Application No. 15819639.4.
Arfi et al, "Catabolism of volatile sulfur compounds precursors by Brevibacterium linens and Geotrichum candidum, two microorganisms of the cheese ecosystem," Journal of Biotechnology, vol. 105, No. 3, pp. 245-253, Nov. 6, 2003.
Uniprot-Q76GS2, "Nucleotide sequence, cloning, overexpression and sigt-directed mutagenesis of the leucine dehydrogenase gene from Bacillus spaericus," Jul. 5, 2004, downloaded from web page: http://www.uniprot.org/uniprot/Q76GS2; Download date Jan. 2018; 1 page.
Biagini et al, "In Vitro Oxidative Decarboxylation of L-2-Hydroxy-4-Methylthiobutanoic Acid by L-2-Hydroxy Acid Oxidase A from Chicken Liver," Biochimie, vol. 77, pp. 249-255 (1995).
Kataoka et al, "Alteration of Substrate Specificity of Leucine Dehydrogenase by Site-Directed Mutagenesis," Journal of Molecular Catalysis B: Enzymatic, vol. 23, pp. 299-309 (2003).
Katoh et al, "Cloning and Sequencing of the Leucine Dehydrogenase Gene from Bacillus Sphaericus IFO 3525 and Importance of the C-Terminal Region for the Enzyme Activity," Journal of Molecular Catalysis B: Enzymatic, vol. 23, pp. 239-247 (2003).
Written Opinion dated Sep. 29, 2015 in Int'l Application No. PCT/JP2015/069106.
Int'l Search Report dated Sep. 29, 2015 in Int'l Application No. PCT/JP2015/069106.
Hummel et al, "Dehydrogenases for the Synthesis of Chiral Compounds," Eur. J. Biochem, col. 184, pp. 1-13 (1989).

(Continued)

*Primary Examiner* — Robert B Mondesi
*Assistant Examiner* — Todd M Epstein
(74) *Attorney, Agent, or Firm* — Panitch Schwarze Belisario & Nadel LLP

(57) ABSTRACT

A polynucleotide encoding an amino acid sequence represented by SEQ ID NO: 1 or 3; a protein having an amino acid sequence represented by SEQ ID NO: 1 or 3; and a method for producing an L-α-amino acid compound are provided. The method includes a step (1) of reacting the protein described herein with an α-hydroxycarboxylic acid compound to obtain a corresponding α-oxocarboxylic acid compound; and a step of reacting a protein having the ability to aminate an α-oxocarboxylic acid compound and convert the same into a corresponding L-α-amino acid compound with the α-oxocarboxylic acid compound obtained in step (1) to obtain a corresponding L-α-amino acid compound.

17 Claims, No Drawings

Specification includes a Sequence Listing.

(56) References Cited

OTHER PUBLICATIONS

Hummel et al, "D-2-Hydroxyisocaproate Dehydrogenase from Lactobacillus Casei," Applied Microbiology and Biotechnology, vol. 21, pp. 7-15 (1985).
Hummel et al, "D-(-)—Mandelic Acid Dehydrogenase from Lactobacillus Curvatus," Applied Microbiology and Biotechnology, vol. 28, pp. 433-439 (1988).
Tichy et al, "Modelling of a Multi-Enzyme System," Chem. Biochem, vol. 1, pp. 25-30 (1987).
Search Report dated Nov. 20, 2017 in SG Application No. 11201700101W (English Translation Only).
Martin-Venegas et al., Intestinal Cell Conversion of DL-2-hydroxy-(4-methylthio)Butanoic Acid in vitro: Dietary Up-Regulation by this Methionine Precursor, British Journal of Nutrition, vol. 106, pp. 350-356 (Mar. 3, 2011).
Martin-Venegas et al., "Conversion of the Methionine Hydroxy Analogue DL-2-Hydroxy-(4_Methylthio) Butanoic Acid to Sulfur-Containing Amino Acids in the Chicken Small Intestine," Poultry Science, vol. 85, pp. 1932-1938 (Nov. 30, 2006).
Uniprot-H0FEG1, "D-isomer specific 2-hydroxyacid dehydrogenaswe NAD-binding protein from Acromobacter arsenitoxydans SY8," Feb. 22, 2012; http://www.uniprot.org/uniprot/H0FEG1; Download date Feb. 2018, 4 pages.
Uniprot-J4YI00, "L-lactate dehydrogenase from Acromobacter piechaudii HLE," Oct. 31, 2012; downloaded from web page: http://www.unitrot.org/uniprot/J4YI00; download date Feb. 2018, 3 pages.
Uniport-H0F2X2, "L-lactate dehyrgenase from Achromobacter arsenitoxydans SY8," Feb. 22, 2012; downloaded from web page: http://www.uniprot.org/uniprot/H0F2X2; Download date Feb. 2018, 3 pages.
Uniprot-E3HUM7, "L lactate dehydrogenase from Achromobacter xylosoxidans (strain A8)," Jan. 11, 2011; Downloaded from web page: http://www.uniprot.org/uniprot/E3HMU7, Download date Feb. 2018, 4 pages.
Langer, "The Conversion of 2-hydroxy-4-methyl Thiobutyric Acidto Methionine by Rat Tissue in vitro," Mar. 1966; Downloaded from web page: http://afrims.amedd.army.mil/weblib/eapr/1966/APR66p289.pdf, Download date: Feb. 2018, 1 page.
Arfi et al., "Catabolism of volatile sulfur compounds precursors by Brevibacterium linens and Geotrichum candidum, two microorganisms of the cheese ecosystem," Journal of Biotechnology, vol. 105, pp. 245-253 (2003).
Office Action dated Dec. 19, 2018 in CN Application No. 201580037342.3.

* cited by examiner

OXIDASE, POLYNUCLEOTIDE THAT CODES FOR SAME, AND USE THEREOF

CROSS-REFERENCE TO RELATED APPLICATION

This application is a Section 371 of International Application No. PCT/JP2015/069106, filed Jul. 2, 2015, which was published in the Japanese language on Jan. 14, 2016, under International Publication No. WO 2016/006522 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "600630-435US Sequence Listing" and a creation date of Jun. 26, 2015, and having a size of 31.5 kB. The sequence listing submitted via EFS-Web is part of the specification and is herein incorporated by reference in its entirety.

TECHNICAL FIELD

The present invention relates to an oxidase, a polynucleotide encoding the same, and a method for producing an α-amino acid compound, etc. using these.

BACKGROUND ART

An α-amino acid compound has been used for various uses in the field of agriculture, forestry, and fisheries, the field of food, the field of medicine, the field of cosmetics, and the like. For example, methionine has been used as a feed additive for animals. To produce the compound, acrolein is reacted with methyl mercaptan to produce 3-(methylthio)propionaldehydehyde, and this is further reacted with prussic acid, ammonia, and carbon dioxide to produce 5-(2-methyl-mercaptoethyl)-hydantoin (methionine hydantoin). Finally, this is hydrolyzed with an alkali to produce alkali metal methionate, and then neutralized by using an acid, for example, sulfuric acid or carbonic acid, to release methionine (see, for example, Patent Document 1, etc.).

PRIOR ART DOCUMENT

Patent Document

Patent Document 1: JP 55-102557 A

DISCLOSURE OF THE INVENTION

Problems to be Solved by the Invention

The production method mentioned above uses prussic acid and acrolein as a C1- or C3-component, and the handling of these raw material compounds requires sufficient control and suitable facilities, etc. Therefore, development of a new method for producing an α-amino acid compound such as methionine is expected.

Means for Solving the Problems

The present invention provides the followings:
Item 1. A polynucleotide encoding any one of the following amino acid sequences (A1) to (A5):

(A1) an amino acid sequence represented SEQ ID NO: 3,
(A2) an amino acid sequence i) having at least 85% sequence identity to an amino acid sequence represented by SEQ ID NO: 3, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(A3) an amino acid sequence represented by i) SEQ ID NO: 3 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(A4) an amino acid sequence ii encoded by a polynucleotide hybridized under a stringent condition to a polynucleotide composed of a sequence complementary to a base sequence represented by SEQ ID NO: 4 or 13, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or
(A5) an amino acid sequence i) represented by SEQ ID NO: 3 which is an altered amino acid sequence having one or more amino acid substitutions selected from the group consisting of substitution of the 109th valine by isoleucine, substitution of the 191st glycine by aspartic acid, and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative (hereinafter sometimes referred to as the present invented polynucleotide (A));

Item 2. The polynucleotide according to the above item 1, which has an altered base sequence comprising a codon selected so that the frequency of use of codon of a base sequence encoding the amino acid sequence corresponds to the frequency of use of codon in *E. coli;*

Item 3. A polynucleotide in which a promoter which can function in a host cell is connected with the polynucleotide according to the above item 1 or 2 so that they can function;

Item 4. A recombinant vector comprising the polynucleotide according to any one of the above items 1 to 3 (hereinafter sometimes referred to as the present invented recombinant vector (A));

Item 5. A transformant in which the polynucleotide according to any one of the above items 1 to 3 or the recombinant vector according to the above item 4 is introduced into a host cell;

Item 6. The transformant according to the above item 5, wherein the host cell is a microorganism or *E. coli;*

Item 7. A transformant having the polynucleotide according to any one of the above items 1 to 3;

Item 8. A method for producing a recombinant vector, which comprises the step of integrating the polynucleotide according to any one of the above items 1 to 3 into a vector which can be replicated in a host cell;

Item 9. A method for producing a transformant, which comprises the step of introducing the polynucleotide according to any one of the above items 1 to 3 or the recombinant vector according to the above item 4 into a host cell;

Item 10. A polynucleotide encoding any one of the following amino acid sequences (B1) to (B4):
(B1) an amino acid sequence represented by SEQ ID NO: 1,
(B2) an amino acid sequence i) having at least 95% sequence identity to an amino acid sequence represented by SEQ ID NO: 1, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(B3) an amino acid sequence represented by i) SEQ ID NO: 1 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or
(B4) an amino acid sequence i) encoded by a polynucleotide hybridized under a stringent condition to a polynucleotide composed of a sequence complementary to a base sequence represented by SEQ ID NO: 2, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative (hereinafter sometimes referred to as the present invented polynucleotide (B));

Item 11. A polynucleotide in which a promoter which can function in a host cell is connected with the polynucleotide according to the above item 10 so that they can function;

Item 12. A recombinant vector comprising the polynucleotide according to the above item 10 or 11 (hereinafter sometimes referred to as the present invented recombinant vector (B));

Item 13. A transformant in which the polynucleotide according to the above item 10 or 11 or the recombinant vector according to the above item 12 is introduced into a host cell;

Item 14. The transformant according to the above item 13, wherein the host cell is a microorganism or E. coli;

Item 15. A transformant having the polynucleotide according to the above item 10 or 11;

Item 16. A method for producing a recombinant vector, which comprises the step of integrating the polynucleotide according to the above item 10 or 11 into a vector which can be replicated in a host cell;

Item 17. A method for producing a transformant, which comprises the step of introducing the polynucleotide according to the above item 10 or 11 or the recombinant vector according to the above item 12 into a host cell;

Item 18. A recombinant vector comprising the polynucleotide according to any one of the above items 1 to 3 and the polynucleotide according to the above item 10 or 11 (hereinafter sometimes referred to as the present invented recombinant vector (AB));

Item 19. The recombinant vector according to the above item 18, which further comprises a polynucleotide encoding an amino acid sequence of a protein having the ability to aminate an α-oxocarboxylic acid compound and convert the same into a corresponding L-α-amino acid compound, or a polynucleotide in which the polynucleotide is connected with a promoter which can function in a host cell so that they can function (hereinafter sometimes referred to as the present invented recombinant vector (ABC));

Item 20. The recombinant vector according to the above item 19, wherein the protein having the ability to aminate an α-oxocarboxylic acid compound and convert the same into a corresponding L-α-amino acid compound is a leucine dehydrogenase;

Item 21. The recombinant vector according to the above item 19 or 20, wherein the amino acid sequence of the protein having the ability to aminate an α-oxocarboxylic acid compound and convert the same into a corresponding L-α-amino acid compound is any one of the following amino acid sequences (C1) to (C3):
(C1) an amino acid sequence represented by SEQ ID NO: 7,
(C2) an amino acid sequence i) having at least 90% sequence identity to an amino acid sequence represented by SEQ ID NO: 7, and ii) of a protein having the ability to aminate an α-oxocarboxylic acid compound and convert the same into a corresponding L-α-amino acid compound, or
(C3) an amino acid sequence i) represented by SEQ ID NO: 7 in which one or plural amino acids are deleted, substituted, or added, and ii) of a protein having the ability to aminate an α-oxocarboxylic acid compound and convert the same into a corresponding L-α-amino acid compound;

Item 22. A transformant in which the recombinant vector according to any one of the above items 18 to 21 is introduced into a host cell;

Item 23. The transformant according to the above item 22, wherein the host cell is a microorganism or E. coli;

Item 24. A transformant having the followings:
i) a polynucleotide having a base sequence encoding an amino acid sequence of a protein having the ability to aminate an α-oxocarboxylic acid compound and convert the same into a corresponding L-α-amino acid compound, or a polynucleotide in which the polynucleotide is connected with a promoter which can function in a host cell so that they can function;
ii) the polynucleotide according to any one of the above items 1 to 3; and
iii) the polynucleotide according to the above item 10 or 11;

Item 25. A protein having any one of the following amino acid sequences (A1) to (A5):
(A1) an amino acid sequence represented SEQ ID NO: 3,
(A2) an amino acid sequence i) having at least 85% sequence identity to an amino acid sequence represented by SEQ ID NO: 3, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(A3) an amino acid sequence represented by i) SEQ ID NO: 3 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, (A4) an amino acid sequence i) encoded by a polynucleotide hybridized under a stringent condition to a polynucleotide composed of a sequence complementary to a base sequence represented by SEQ ID NO: 4 or 13, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or (A5) an amino acid sequence i) represented by SEQ ID NO: 3 which is an altered amino acid sequence having one or more amino acid substitutions selected from the group consisting of substitution of the 109th valine by isoleucine, substitution of the 191st glycine by aspartic acid, and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative (hereinafter sometimes referred to as the present invented protein (A));

Item 26. A protein having any one of the following amino acid sequences (B1) to (B4):

(B1) an amino acid sequence represented by SEQ ID NO: 1,
(B2) an amino acid sequence i) having at least 95% sequence identity to an amino acid sequence represented by SEQ ID NO: 1, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(B3) an amino acid sequence represented by i) SEQ ID NO: 1 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or
(B4) an amino acid sequence i) encoded by a polynucleotide hybridized under a stringent condition to a polynucleotide composed of a sequence complementary to a base sequence represented by SEQ ID NO: 2, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative (hereinafter sometimes referred to as the present invented protein (B));

Item 27. A method for producing an L-α-amino acid compound, which comprises (1) the step of reacting any one or both of a protein having any one of the following amino acid sequences (A1) to (A5):

(A1) an amino acid sequence represented SEQ ID NO: 3,
(A2) an amino acid sequence i) having at least 85% sequence identity to an amino acid sequence represented by SEQ ID NO: 3, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, (A3) an amino acid sequence represented by i) SEQ ID NO: 3 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, (A4) an amino acid sequence i) encoded by a polynucleotide hybridized under a stringent condition to a polynucleotide composed of a sequence complementary to a base sequence represented by SEQ ID NO: 4 or 13, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or (A5) an amino acid sequence i) represented by SEQ ID NO: 3 which is an altered amino acid sequence having one or more amino acid substitutions selected from the group consisting of substitution of the 109th valine by isoleucine, substitution of the 191st glycine by aspartic acid, and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative;

and a protein having any one of the following amino acid sequences (B1) to (B4):

(B1) an amino acid sequence represented by SEQ ID NO: 1,
(B2) an amino acid sequence i) having at least 95% sequence identity to an amino acid sequence represented by SEQ ID NO: 1, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(B3) an amino acid sequence represented by i) SEQ ID NO: 1 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or
(B4) an amino acid sequence i) encoded by a polynucleotide hybridized under a stringent condition to a polynucleotide composed of a sequence complementary to a base sequence represented by SEQ ID NO: 2, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative;

with an α-hydroxycarboxylic acid compound to obtain a corresponding α-oxocarboxylic acid compound, and (2) the step of reacting a protein having the ability to aminate an α-oxocarboxylic acid compound and convert the same into a corresponding L-α-amino acid compound with the α-oxocarboxylic acid compound obtained in the step (1) to obtain a corresponding L-α-amino acid compound (hereinafter sometimes referred to as the present invented production method);

Item 28. The production method according to the above item 27, wherein the α-hydroxycarboxylic acid compound is a sulfur-containing α-hydroxycarboxylic acid compound, the corresponding α-oxocarboxylic acid compound is a sulfur-containing α-oxocarboxylic acid compound, the corresponding L-α-amino acid compound is a sulfur-containing L-α-amino acid compound, the protein reacted with an α-hydroxycarboxylic acid compound in the step (1) is a protein at least having the ability to oxidize a 2-hydroxy-4-(methylthio)butyric acid derivative and convert the same into a corresponding 2-oxo-4-(methylthio)butyric acid derivative;

Item 29. The production method according to the above item 28, wherein the sulfur-containing α-hydroxycarboxylic acid compound is a compound represented by formula (1):

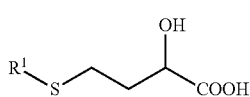

(1)

wherein $R^1$ represents a hydrogen atom or an optionally substituted C1-8 alkyl group;
the sulfur-containing α-oxocarboxylic acid compound is a compound represented by formula (2):

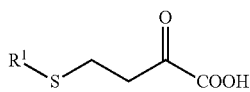

(2)

wherein $R^1$ is the same as defined above;
and the sulfur-containing L-α-amino acid compound is a compound represented by formula (3):

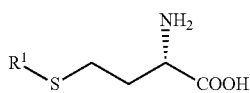

(3)

wherein R is the same as defined above:

Item 30. The production method according to the above item 27, wherein the α-hydroxycarboxylic acid compound is α-hydroxy-isocaproic acid, the corresponding α-oxocarboxylic acid compound is α-oxo-isocaproic acid, the corresponding L-α-amino acid compound is L-leucine, and the protein reacted with an α-hydroxycarboxylic acid compound in the step (1) is a protein at least having the ability to oxidize an α-hydroxy-isocaproic acid derivative and convert the same into a corresponding α-oxo-isocaproic acid derivative;

Item 31. The production method according to any one of the above items 27 to 30, wherein the protein having the ability to aminate an α-oxocarboxylic acid compound and convert the same into a corresponding L-α-amino acid compound is a leucine dehydrogenase;

Item 32. The production method according to any one of the above items 27 to 31, wherein the amino acid sequence of a protein having the ability to aminate an α-oxocarboxylic acid compound and convert the same into a corresponding L-α-amino acid compound is any one of the following amino acid sequences (C1) to (C3):

(C1) an amino acid sequence represented by SEQ ID NO: 7,
(C2) an amino acid sequence i) having at least 90% sequence identity to an amino acid sequence represented by SEQ ID NO: 7, and ii) of a protein having the ability to aminate an α-oxocarboxylic acid compound and convert the same into a corresponding L-α-amino acid compound, or
(C3) an amino acid sequence i) represented by SEQ ID NO: 7 in which one or plural amino acids are deleted, substituted, or added, and ii) of a protein having the ability to aminate an α-oxocarboxylic acid compound and convert the same into a corresponding L-α-amino acid compound;

Item 33. The production method according to any one of the above items of 27 to 32, wherein the protein reacted with an α-hydroxycarboxylic acid compound in the step (1) is provided in a reaction system in the form in which the protein is included in a transformant in which a polynucleotide encoding the protein is introduced into a host cell or in a treated product thereof;

Item 34. The production method according to the above item 33, wherein the transformant is the transformant according to any one of the above items 5, 6, 7, 13, 14, 15, 22, 23, and 24;

Item 35. The production method according to any one of the above items 27 to 34, wherein the protein having the ability to aminate an α-oxocarboxylic acid compound and convert the same into a corresponding L-α-amino acid compound is provided in a reaction system in the form in which the protein is included in a transformant in which a polynucleotide encoding the protein is introduced into a host cell or in a treated product thereof;

Item 36. The production method according to the above item 35, wherein the transformant is the transformant according to any one of the above items 22, 23, and 24;

Item 37. The production method according to any one of the above items 27 to 36, wherein the step (1) is performed in the presence of a protein having the ability to convert a reduced β-nicotinamide adenine dinucleotide or a reduced β-nicotinamide adenine dinucleotide phosphate into its oxidized form;

Item 38. The production method according to the above item 37, wherein the protein having the ability to convert a reduced β-nicotinamide adenine dinucleotide or a reduced β-nicotinamide adenine dinucleotide phosphate into its oxidized form is a protein further having the ability to aminate an α-oxocarboxylic acid compound and convert the same into a corresponding L-α-amino acid compound;

Item 39. The production method according to the above item 37 or 38, wherein the protein having the ability to convert a reduced β-nicotinamide adenine dinucleotide or a reduced β-nicotinamide adenine dinucleotide phosphate into its oxidized form is provided in a reaction system in the form in which the protein is included in a transformant in which a polynucleotide encoding the protein is introduced into a host cell or in a treated product thereof;

Item 40. The production method according to any one of the above items 27 to 39, wherein the step (2) is performed in the presence of a protein having the ability to convert an oxidized β-nicotinamide adenine dinucleotide or an oxidized β-nicotinamide adenine dinucleotide phosphate into its reduced form;

Item 41. The production method according to the above item 40, wherein the protein having the ability to convert an oxidized β-nicotinamide adenine dinucleotide or an oxidized β-nicotinamide adenine dinucleotide phosphate into its reduced form is a protein further having the ability to oxidize an α-hydroxycarboxylic acid compound and convert the same into a corresponding α-oxocarboxylic acid compound;

Item 42. The production method according to the above item 40 or 41, wherein the protein having the ability to convert an oxidized β-nicotinamide adenine dinucleotide or an oxidized β-nicotinamide adenine dinucleotide phosphate into its reduced form is provided in a reaction system in the form in which the protein is included in a transformant in which a polynucleotide encoding the protein is introduced into a host cell or in a treated product thereof;

Item 43. The production method according to any one of the above items 27 to 42, wherein the step (1) and the step (2) are performed in one reaction system; and the like.

Effects of the Invention

According to the present invention, it is possible to provide an oxidase, a polynucleotide encoding the same, a method for producing an α-amino acid compound such as methionine and leucine using these, and the like.

MODE FOR CARRYING OUT THE INVENTION

In the present invention, examples of a method for artificially altering an amino acid include a method in which a site-specific mutation is introduced into a polynucleotide encoding an amino acid sequence including an amino acid to be altered and then this polynucleotide is expressed by a conventional method. Examples of a method for introducing a site-specific mutation can include the methods by Olfert Landt et al. (Gene 96 125-128 1990), Smith et al. (Genetic Engineering 3 1 Setlow, J. and Hollaender, A Plenum: New York), Vlasuk et al. (Experimental Manipulation of Gene Expression, Inouye, M.: Academic Press, New York), Hos. N. Hunt et al. (Gene 77 51 1989), and the like, and a method for using commercial kits such as Mutan-Express Km (manufactured by Takara Bio), TaKaRa La PCR in vitro Mutagenesis Kit (manufactured by Takara Bio), and Quick-Change II Site-Directed Mutagenesis Kit (manufactured by STRATAGENE).

Examples of the method for artificially altering an amino acid also include a method in which a mutation is randomly introduced into a polynucleotide encoding an amino acid sequence including an amino acid to be altered and then this polynucleotide is expressed by a conventional method. Examples of a method for randomly introducing a mutation include a method in which PCR is performed using a polynucleotide encoding the above amino acid sequences as a template and using a primer pair which can amplify the full length of the polynucleotide, under a reaction condition in which the concentration of each of dATP, dTTP, dGTP, and dCTP added which is used as a substrate is changed from the normal concentration, or a reaction condition in which the concentration of $Mg^{2+}$, which accelerates the polymerase reaction, is increased compared with the normal concentration. Examples of such PCR method include the method mentioned in Method in Molecular Biology, (31), 1994, 97-112.

"Sequence identity" means the identity between two amino acid sequences or base sequences. The "sequence identity" is determined by comparing two sequences aligned to an optimal state over all regions of sequences to be compared. In optimal alignment of amino acid sequences or base sequences to be compared, addition or deletion (e.g., gap, etc.) may be allowed. Such sequence identity can be calculated by using, for example, sequence analysis tools such as the BESTFIT program (Devereux et al. (1984) Nucleic Acids Research 12, p 387-395) provided by UWGCG Package, PILEUP, and the BLAST algorithm (Altschul S. F. (1993) J Mol Evol 36:290-300; Altschul S. F. (1990) J Mol Biol 215:403-10). Sequence identity can also be calculated by using commercial sequence analysis software.

In the present invention, microorganisms as a source of a target polynucleotide may be separated naturally, or may be obtained through purchase from culture collection institutes.

Examples of the culture collection institutes from which such microorganisms can be obtained can include the following culture collection institutes.

1. Institute for Fermentation, Osaka (IFO) Collection

At present, it is transferred to the NITE Biological Resource Center (NBRC). For obtaining microorganisms, it is only necessary to apply purchase to the NBRC. For purchase application, for example, it is only necessary to access the website of the NBRC.

2. American Type Culture Collection (ATCC)

Microorganisms can be obtained through the ATCC Business Group of Summit Pharmaceuticals International Corporation. For purchasing microorganisms, for example, it is only necessary to access the website of the Group. Microorganisms may be purchased directly from the ATCC.

3. Japan Collection of Microorganisms (JCM)

At present, it is transferred to the Japan Collection of Microorganisms of RIKEN BioResource Center (RIKEN BRC). For obtaining microorganisms, it is only necessary to apply purchase to the institute, and, for example, to access websites related to culture collection on the website of the institute.

4. IAM Culture Collection

At present, among the IAM Culture Collection preserved strains, bacteria, yeasts, filamentous fungi are transferred to the RIKEN BRC-JCM, and microalgae are transferred to the Microbial Culture Collection at the National Institute for Environmental Studies (NIES). For obtaining microorganisms, it is only necessary to apply purchase to these institutes, and, for example, to access websites related to culture collection on the websites of these institutes.

Examples of a method for hybridizing a probe to chromosomal DNA or a DNA library for cloning of a target polynucleotide include colony hybridization and plaque hybridization, and a method can be selected according to the type of the vector used for preparation of the library.

When a library to be used has been prepared by using a plasmid vector, it is better to use colony hybridization. Specifically, the DNA of the library is introduced into a host microorganism to obtain a transformant, and the transformant thus obtained is diluted, and then the dilution is seeded on an agar medium and cultured until a colony appears.

When a library to be used has been prepared by using a phage vector, it is better to use plaque hybridization. Specifically, a host microorganism and a phage of the library are mixed under an infectible condition, and further mixed with a soft agar medium, and then the mixture is seeded on an agar medium and cultured until a plaque appears.

In any hybridization above, a membrane is placed on the above cultured agar medium, a transformant or a phage is adsorbed/transcribed on the membrane. After this membrane is treated with an alkali, it is neutralized, and then DNA is immobilized on the membrane. More specifically, for example, in the case of plaque hybridization, a nitrocellulose membrane or a nylon membrane (e.g., Hybond-N+ (GE Healthcare Japan, trade mark)) is placed on the agar medium, and allowed to stand for about one minute to adsorb/transcribe a phage particle to the membrane. Next, phage DNA is eluted on the membrane by immersing the membrane in an alkali solution (e.g., 1.5 M sodium chloride and 0.5 M sodium hydroxide) for about 3 minutes to dissolve the phage particle, and the membrane is immersed in a neutralizing solution (e.g., 1.5 M sodium chloride and 0.5 M Tris-hydrochloric acid buffer pH 7.5) for about 5 minutes. Subsequently, the membrane is washed with a rinsing fluid (e.g., 0.3 M sodium chloride, 30 mM citric acid, and 0.2 M Tris-hydrochloric acid buffer pH 7.5) for about 5 minutes, and then, for example, the membrane is heated at about 80° C. for about 90 minutes to immobilize the phage DNA on the membrane.

Using the membrane prepared in this way, hybridization of a probe is performed. Hybridization can be performed in accordance with, for example, the description such as J. Sambrook, E. F. Frisch, T. Maniatis "Molecular Cloning: A Laboratory Manual 2nd edition (1989)" Cold Spring Harbor Laboratory Press.

DNA to be used as a probe may be labeled by a radioisotope ox labeled by a fluorochrome.

Examples of a method for labeling DNA to be used as a probe by a radioisotope include a method in which PCR is performed using DNA to be used as a probe as a template by substituting dCTP in a PCR reaction solution by ($\alpha$-$^{32}$P) dCTP by using the Random Primer DNA Labeling Kit (manufactured by Takara Bio), etc.

When DNA used as a probe is labeled by a fluorochrome, for example, the ECL Direct Nucleic Acid Labeling and Detection System (manufactured by GE Healthcare Japan), etc. can be used.

Hybridization can be performed, for example, as follows. A prehybridization solution containing 450 to 900 mM sodium chloride and 45 to 90 mM sodium citrate, containing sodium dodecyl sulfate (SDS) at a concentration of 0.1 to 1.0% by weight, containing denatured non-specific DNA at a concentration of 0 to 200 µl/ml, and optionally containing albumin, Ficoll, polyvinylpyrrolidone, and the like at a concentration of 0 to 0.2% by weight each (preferably, a prehybridization solution containing 900 mM sodium chloride, 90 mM sodium citrate, 1.0% by weight of SDS, and 100 µl/ml of denatured calf-thymus DNA) is prepared in the proportion within a range of 50 to 200 µl based on 1 cm$^2$ of the membrane prepared as mentioned above, and the membrane is immersed in the prehybridization solution and incubated at 42 to 65° C. for 1 to 4 hours.

Next, a solution prepared by mixing, for example, a hybridization solution containing 450 to 900 mM sodium chloride and 45 to 90 mM sodium citrate, containing SDS at a concentration of 0.1 to 1.0% by weight, containing denatured non-specific DNA at a concentration of 0 to 200 µg/ml, and optionally containing albumin, Ficoll, polyvinylpyrrolidone, and the like at a concentration of 0 to 0.2% by weight each (preferably, a hybridization solution containing 900 mM sodium chloride, 90 mM sodium citrate, 1.0% by weight of SDS, and 100 µg/ml of denatured calf-thymus DNA) with a probe obtained by preparation using the method mentioned above (the amount corresponds to 1.0× 10$^4$ to 2.0×10$^6$ cpm based on 1 cm$^2$ of the membrane) is prepared in the proportion within a range of 50 to 200 µl based on 1 cm$^2$ of the membrane, and the membrane is immersed in the hybridization solution and incubated at 42 to 65° C. for 12 to 20 hours.

After the hybridization, the membrane is removed, and washed with a rinsing fluid at 42 to 65° C. containing 15 to 300 mM sodium chloride, 1.5 to 30 mM sodium citrate, 0.1 to 1.0% by weight of SDS, and the like (preferably, a rinsing fluid at 65° C. containing 15 mM sodium chloride, 1.5 mM sodium citrate, and 1.0% by weight of SDS), etc. The washed membrane is gently washed with 2×SSC (300 mM sodium chloride and 30 mM sodium citrate), and then dried. By subjecting this membrane to, for example, autoradiography, etc. to detect the position of the probe on the membrane, a clone at the position on the membrane of DNA to be hybridized to the probe used is identified on the original agar medium, and fishing of this is performed to isolate a clone having the DNA.

From a cultured cell obtained by culture of the clone thus obtained, a target polynucleotide can be prepared.

To express a target polynucleotide in a host cell, for example, a polynucleotide in which a promoter which can function in a host cell is connected with the polynucleotide so that they can function is prepared, and introduced into a host cell.

As used herein, "connected so that they can function" means that when a host cell is transformed by introducing a target polynucleotide into the host cell, the polynucleotide is bound to a promoter so that it is expressed under control of the promoter.

Examples of the promoter which can function in a microorganism include a lactose operon promoter of *E. coli*, a tryptophan operon promoter of *E. coli*, a T7 phage promoter, or a synthetic promoter which can function in *E. coli*, such as a tac promoter, a trc promoter, or a T7lac promoter.

A recombinant vector can be prepared by integrating a target polynucleotide, or a polynucleotide in which a promoter which can function in a host cell is connected with the polynucleotide so that they can function into a vector. Examples of the vector to be used can include a vector which contains genetic information replicable in a host cell, can proliferate autonomously, can be isolated and purified from a host cell, and encodes a detectable marker. Examples of a vector available when the host cell is *E. coli* include pUC119 (manufactured by Takara Bio), pTV118N (manufactured by Takara Bio), pBluescriptII (manufactured by Toyobo), pCR2.1-TOPO (Invitrogen), pTrc99A (manufactured by GE Healthcare Japan), pKK22 3-3 (manufactured by GE Healthcare Japan), pET-22b (manufactured by Novagen), and pET-15b (manufactured by Novagen). When a vector containing a selection marker gene (e.g., an antibiotic resistance-imparting gene such as a kanamycin resistance gene and a neomycin resistance gene) is used as the vector, a transformant into which the vector is introduced can be selected using the phenotype, etc. of the selection marker gene as an index.

A transformant to be used in the present invention can be produced by introducing a target polynucleotide, a polynucleotide in which a promoter which can function in a host cell is connected with the polynucleotide so that they can function, or a recombinant vector containing these polynucleotides into a host cell.

Examples of the host cell include a microorganism belonging to the genus *Escherichia*, *Bacillus*, *Corynebacterium*, *Staphylococcus*, *Streptomyces*, *Saccharomyces*, *Kluyveromyces*, *Pichia*, *Rhodococcus*, or *Aspergillus*.

As a method for introducing a polynucleotide or a recombinant vector into a host cell, a usually used introduction method can be applied depending on a host cell to be used, and examples thereof include the calcium chloride method mentioned in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X, and the like, and electroporation mentioned in "Methods in Electroporation: Gene Pulser/*E. coli* Pulser System" Bio-Rad Laboratories, (1993), and the like.

A transformant into which a target polynucleotide or a recombinant vector, etc. is introduced can be selected by, for example, using the phenotype of a selection marker gene contained in a vector as mentioned above as an index.

The fact that the obtained transformant has the target polynucleotide can be confirmed by, for example, performing confirmation of a restriction enzyme site, analysis of a base sequence, Southern hybridization, Western hybridization, and the like, in accordance with a usual method mentioned in "Molecular Cloning: A Laboratory Manual 2nd edition" (1989), Cold Spring Harbor Laboratory Press, and the like.

As a medium for culture of the transformant to be used in the present invention, for example, various media appropriately containing a carbon source, a nitrogen source, an organic salt, an inorganic salt, and the like which are usually used for culture of host cells of microorganisms, etc. can be used.

Examples of the carbon source include saccharides such as glucose, dextrin, and sucrose; sugar alcohols such as glycerol; organic acids such as fumaric acid, citric acid, and pyruvic acid; animal oil; vegetable oil; and molasses. The amount of these carbon sources added to a medium is usually within a range of about 0.1 to 30% (w/v) based on the amount of a culture solution.

Examples of the nitrogen source include natural organic sources of nitrogen such as meat extract, peptone, yeast extract, malt extract, soy flour, corn steep liquor, cottonseed flour, dried yeast, and casamino acid; amino acids; sodium salts of inorganic acids such as sodium nitrate; ammonium salts of inorganic acids such as ammonium chloride, ammonium sulfate, and ammonium phosphate; ammonium salts of organic acids such as ammonium fumarate and ammonium citrate; and urea. Of these, ammonium salts of organic acids, natural organic sources of nitrogen, amino acids, and the like can also be often used as a carbon source. The amount of these nitrogen sources added to a medium is usually within a range of about 0.1 to 30% (w/v) based on the amount of a culture solution.

Examples of the organic salt and the inorganic salt can include chlorides, sulfates, acetates, carbonates, and phosphates of potassium, sodium, magnesium, iron, manganese, cobalt, zinc, and the like. Specific examples thereof include sodium chloride, potassium chloride, magnesium sulfate, ferrous sulfate, manganese sulfate, cobalt chloride, zinc sulfate, copper sulfate, sodium acetate, calcium carbonate, monopotassium hydrogenphosphate, and dipotassium hydrogenphosphate. The amount of these organic salts and/or inorganic salts added to a medium is usually within a range of about 0.0001 to 5% (w/v) based on the amount of a culture solution.

In the case of a transformant into which a polynucleotide is introduced in which a promoter induced by allolactose such as a tac promoter, a trc promoter, a T7lac promoter, and a lac promoter is connected with a polynucleotide encoding a target protein so that they can function, for example, a small amount of isopropyl thio-β-D-galactoside (IPTG) may be added to a medium as an inducer for inducing the production of the target protein. Also, in the case of culture of a transformant in which a polynucleotide in which a T7 phage promoter is connected with a polynucleotide encoding a target protein so that they can function is introduced into a lysogen of bacteriophage DE3 (λDE3 lysogen) in which a T7 RNA polymerase gene is integrated under control of an lacUV5 promoter, a small amount of IPTG may be added to a medium as an inducer for inducing the production of the target protein.

Culture of the transformant can be performed in accordance with a method usually used for culture of host cells such as microorganisms, and examples thereof include liquid culture and solid culture such as test tube-shaking culture, reciprocal shaking culture, jar fermenter culture, and tank culture.

The culture temperature can be appropriately changed in a range so that the transformant can grow, and is usually about 15° C. to about 40° C. The pH of the medium is preferably within a range of about 6 to about 8. The culture time varies depending on the culture condition, and is usually preferably about one day to about 5 days.

As a method for purifying a target protein from a cultured product of a transformant producing the target protein having a polynucleotide encoding the target protein, for example, a transformant in which a polynucleotide encoding the target protein is introduced into a host cell, a usual method used for purification of proteins can be applied, and examples thereof can include the following methods:

Cells are collected by centrifugation, etc. from a cultured product of the transformant, and then the cells are disrupted by physical disruption such as sonication, Dyno-Mill treatment, or French press treatment or by chemical disruption using surfactants or lytic enzymes such as lysozyme, etc. From the disruption liquid thus obtained, impurities are removed by centrifugation, membrane filter filtration, and the like to prepare a cell-free extract. The extract is fractionated by appropriately using a separation and purification method such as cation exchange chromatography, anion exchange chromatography, hydrophobic interaction chromatography, gel filtration chromatography, metal chelate chromatography, and affinity chromatography, and thereby the target protein can be purified.

Examples of a carrier to be used in the chromatography include an insoluble macromolecular carrier such as cellulose, dextrin, or agarose into which a carboxymethyl (CM) group, a diethylaminoethyl (DEAE) group, a phenyl group, or a butyl group is introduced. A commercial carrier-filled column can be used, and examples of the commercial carrier-filled column include Q-Sepharose FF (trade name, manufactured by GE Healthcare Japan), Phenyl-Sepharose HP (trade name, manufactured by GE Healthcare Japan), and TSK-gel G3000SW (trade name, manufactured by Tosoh Corporation).

When the target protein is a protein in which consecutive several residues of histidine are added to its amino-terminal or carboxy-terminal domain, the protein can be purified by using a metal chelate affinity column. When the target protein is produced as a protein fused with a glutathione S-transferase, the protein can be purified by using a glutathione S-transferase monoclonal antibody column.

Examples of "treated product of transformant" as used herein include a freeze-dried transformant, an organic solvent-treated transformant, a dried transformant, a triturated transformant, an autolysate of a transformant, a sonicate of a transformant, a transformant extract, and an alkali-treated product of a transformant. Examples of the transformant extract include a cell-free extract, a partially purified protein or a purified protein prepared from a transformant, and an immobilized product thereof. Examples of a method for obtaining the immobilized product include the carrier binding method (a method for adsorbing a target protein, etc. to an inorganic carrier such as a silica gel and a ceramic, cellulose, or an ion exchange resin, etc.) and the entrapment method (a method for trapping a target protein, etc. in a macromolecular meshwork such as polyacrylamide, a sulfur-containing polysaccharide gel (e.g., a carrageenan gel), an alginic acid gel, or an agar gel, etc.).

Taking account of industrial production using a transformant, rather than use of a living transformant, use of a treated product obtained by killing the transformant is preferable in terms of less limitation on a production facility. Examples of a method for killing a transformant include physical sterilization (heating, drying, freezing, light, sonication, filtration, electrification) and chemical sterilization (alkali, acid, halogen, an oxidizing agent, sulfur, boron, arsenic, metal, alcohol, phenol, amine, sulfide, ether, aldehyde, ketone, cyanogen, and an antibiotic). Generally, of these sterilization methods, it is desirable to select a treatment method which does not inactivate the enzyme activity of the target protein as possible and has less effects on the reaction system such as residue and contamination.

The present invented polynucleotide (A) encodes any one of the following amino acid sequences (A1) to (A5):
(A1) an amino acid sequence represented SEQ ID NO: 3,
(A2) an amino acid sequence i) having at least 85% sequence identity to an amino acid sequence represented by SEQ ID NO: 3, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(A3) an amino acid sequence represented by i) SEQ ID NO: 3 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative,
(A4) an amino acid sequence i) encoded by a polynucleotide hybridized under a stringent condition to a polynucleotide composed of a sequence complementary to a base sequence represented by SEQ ID NO: 4 or 13, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or
(A5) an amino acid sequence i) represented by SEQ ID NO: 3 which is an altered amino acid sequence having one or more amino acid substitutions selected from the group consisting of substitution of the 109th valine by isoleucine, substitution of the 191st glycine by aspartic acid, and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative.

The present invented protein (A) has any one of the above amino acid sequences (A1) to (A5).

A difference which is sometimes observed between an amino acid sequence encoded by the present invented polynucleotide (A) or an amino acid sequence of the present invented protein (A) and an amino acid sequence represented by SEQ ID NO: 3 is deletion, substitution, or addition, etc. of some amino acids (hereinafter sometimes generally referred to as alteration of an amino acid). The "addition" includes not only addition of an amino acid to the end of a sequence but also insertion of an amino acid into a sequence. Examples of the alteration of an amino acid can include (a) deletion by intracellular processing of a protein having an amino acid sequence represented by SEQ ID NO: 3, (b) deletion, substitution, or addition of an amino acid as a result of a naturally occurring gene mutation due to the species difference or individual difference of an organism from which the protein is derived, or (c) deletion, substitution, or addition of an amino acid occurring due to a mutation of an artificially introduced gene, etc.

The number of amino acids to be altered is not limited as long as the number is within a range so that a protein having the above altered amino acid sequence can exert the same ability as that of a protein before alteration, namely any one or both of the ability to oxidize a 2-hydroxy-4-(methylthio) butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative.

Examples of "plural amino acids" in the amino acid sequence (A3) encoded by the present invented polynucleotide (A) or the amino acid sequence (A3) of the present invented protein (A) include 2, 3, 4, 5, 6, 7, 10, 15, 20, 25, 30, 35, 40, 45, or 48 amino acids.

Examples of the substitution of an amino acid include conservative substitution to an amino acid having similar hydrophobicity, electric charge, pK, conformational characteristics, or the like. Specific examples of such substitution include substitution of (1) glycine, alanine; (2) valine, isoleucine, leucine; (3) aspartic acid, glutamic acid, asparagine, glutamine, (4) serine, threonine; (5) lysine, arginine; (6) phenylalanine, tyrosine; and the like in the group.

Examples of the addition of an amino acid can include addition of about 7 to 25 residues of amino acid including about consecutive 6 residues of histidine to the amino terminus or carboxy terminus of an amino acid sequence of a protein. More specific examples can include addition of an amino acid sequence represented by SEQ ID NO: 44 to the amino terminus of an amino acid sequence of a protein, and addition of an amino acid sequence represented by SEQ ID NO: 45 to the carboxy terminus of an amino acid sequence of a protein.

Examples of "at least 85% sequence identity" in the amino acid sequence (A2) encoded by the present invented polynucleotide (A) or the amino acid sequence (A2) of the present invented protein (A) include at least 85, 90, 95, 98, or 99% sequence identity.

In an amino acid sequence encoded by the present invented polynucleotide (A) or an amino acid sequence of the present invented protein (A), "polynucleotide hybridized under a stringent condition to a polynucleotide composed of a sequence complementary to a base sequence represented by SEQ ID NO: 4 ox 13" means a polynucleotide (1) which form a hybrid by base pairing with a polynucleotide composed of a sequence complementary to a base sequence represented by SEQ ID NO: 4 or 13 by being hybridized at 65° C. under a high ionic concentration [for example, 6×SSC (900 mM sodium chloride and 90 mM sodium citrate)] and (2) in which the hybrid is maintained even after being incubated at 65° C. for 30 minutes under a low ionic concentration [for example, 0.1×SSC (15 mM sodium chloride and 1.5 mM sodium citrate)] in the Southern hybridization mentioned in, for example, "Cloning and Sequence" (supervised by Itaru Watanabe, edited by Masahiro Sugiura, 1989, published by Nosonbunka-sha), etc.

Specific examples of the above polynucleotide include a polynucleotide having a base sequence represented by SEQ ID NO: 4 or 13, a polynucleotide having a base sequence represented by SEQ ID NO: 4 or 13 in which some bases are deleted, substituted, or added, or a polynucleotide having a base sequence having at least 90%, 95%, 98%, or 99% sequence identity to a base sequence represented by SEQ ID NO: 4 or 13.

Specific examples of the amino acid sequence (A5) encoded by the present invented polynucleotide (A) or the amino acid sequence (A5) of the present invented protein (A) will be described below.

(A5-1) an amino acid sequence i) represented by SEQ ID NO: 3 which is an altered amino acid sequence having substitution of the 109th valine by isoleucine, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative (hereinafter sometimes referred to as the altered amino acid sequence V109I);

(A5-2) an amino acid sequence i) represented by SEQ ID NO: 3 which is an altered amino acid sequence having substitution of the 191st glycine by aspartic acid, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative (hereinafter sometimes referred to as the altered amino acid sequence G191D);

(A5-3) an amino acid sequence i) represented by SEQ ID NO: 3 which is an altered amino acid sequence having substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative (hereinafter sometimes referred to as the altered amino acid sequence Q246R);

(A5-4) an amino acid sequence i) represented by SEQ ID NO: 3 which is an altered amino acid sequence having substitution of the 109th valine by isoleucine and substitution of the 191st glycine by aspartic acid, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative (hereinafter sometimes referred to as the altered amino acid sequence V109I/G191D);

(A5-5) an amino acid sequence i) represented by SEQ ID NO: 3 which is an altered amino acid sequence having substitution of the 109th valine by isoleucine and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative (hereinafter sometimes referred to as the altered amino acid sequence V109I/Q246R);

(A5-6) an amino acid sequence i) represented by SEQ ID NO: 3 which is an altered amino acid sequence having substitution of the 191st glycine by aspartic acid and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio) butyric acid derivative and the ability to oxidize an α-hydroxy-isocaproic acid derivative and convert the same into a corresponding α-oxo-isocaproic acid derivative (hereinafter sometimes referred to as the altered amino acid sequence G191D/Q246R); and (A5-7) an amino acid sequence i) represented by SEQ ID NO: 3 which is an altered amino acid sequence having substitution of the 109th valine by isoleucine, substitution of the 191st glycine by aspartic acid, and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative (hereinafter sometimes referred to as the altered amino acid sequence V109I/G191D/Q246R).

Specific examples of the altered amino acid sequence V109I/G191D/Q246R can include an amino acid sequence represented by SEQ ID NO: 5. Examples of a base sequence encoding an amino acid sequence represented by SEQ ID NO: 5 can include a base sequence represented by SEQ ID NO: 6.

The present invented polynucleotide (A) may be a polynucleotide cloned from DNAs existing in the natural world, a polynucleotide into which deletion, substitution, or addition of some bases in a base sequence of this cloned polynucleotide is artificially introduced, or a chemically synthesized polynucleotide.

The present invented polynucleotide (A) can be obtained from, for example, a microorganism having the ability to oxidize α-hydroxycarboxylic acid to corresponding α-oxocarboxylic acid, and specifically, a microorganism belonging to the genus *Achromobacter* such as an *Achromobacter denitrificans* ATCC55564 strain.

For example, a DNA library is prepared from a microorganism belonging to the genus *Achromobacter* such as *Achromobacter denitrificans*, etc. in accordance with a usual genetic engineering method (e.g., the method mentioned in "New Cell Engineering Experimental Protocol" (edited by Department of Oncology, Institute of Medical Science, the University of Tokyo, Shujunsha Co., Ltd., 1993)). Then, by performing PCR using the DNA library thus prepared as a template and using an appropriate primer, a polynucleotide encoding an amino acid sequence represented by SEQ ID NO: 3, a polynucleotide encoding an amino acid sequence represented by SEQ ID NO: 3 in which one or plural amino acids are deleted, substituted, or added, or a polynucleotide having a base sequence represented by SEQ ID NO: 4, etc. is amplified, and thereby the present invented polynucleotide (A) can be prepared.

A restriction enzyme recognition sequence, etc. may be added to the 5' end side, the 3' end side, or both of a primer used for the above PCR.

For example, by performing PCR using the above DNA library as a template and using an oligonucleotide having a base sequence represented by SEQ ID NO: 11 and an oligonucleotide having a base sequence represented by SEQ ID NO: 12 as a primer, a polynucleotide composed of a base sequence represented by SEQ ID NO: 4 can be amplified.

Examples of a condition for the above PCR include a condition in which a reaction solution prepared by mixing 20 µM each of 4 dNTPs, 15 pmol each of 2 oligonucleotide primers, 1.3 U of a Taq polymerase, and a DNA library as a template is incubated at 94° C. for 2 minutes, and then an incubation cycle consisting of incubation at 94° C. for 10 seconds, followed by 65° C. for 30 seconds, followed by 72° C. for 90 seconds is performed 10 times, subsequently an incubation cycle consisting of incubation at 94° C. for 10 seconds, followed by 65° C. for 30 seconds, followed by 72° C. for one minute and 5 seconds is performed 20 times, and further the solution is maintained at 72° C. for 7 minutes.

Also by performing PCR using the above DNA library as a template and using an oligonucleotide having a partial base sequence selected from a base sequence encoding an amino acid sequence represented by SEQ ID NO: 3 (e.g., an oligonucleotide composed of a base sequence of at least about 14 bases at the 5' end of a base sequence encoding an amino acid sequence represented by SEQ ID NO: 3) and an oligonucleotide of at least about 14 bases composed of a base sequence complementary to a base sequence near the DNA insertion site of the vector used for the DNA library construction as a primer, a polynucleotide having a base sequence encoding an amino acid sequence represented by SEQ ID NO: 3, or a polynucleotide having a base sequence encoding an amino acid sequence represented by SEQ ID NO: 3 in which one or plural amino acids are deleted, substituted, or added, etc. is amplified, and thereby the present invented polynucleotide (A) can be prepared.

The present invented polynucleotide (A) can also obtained by, for example, hybridizing, as a probe, DNA composed of a base sequence of at least about 15 bases having a partial base sequence selected from a base sequence encoding an amino acid sequence represented by SEQ ID NO: 3 to a DNA library into which a vector derived from a microorganism or a phage is inserted under the condition mentioned above to detect DNA to which the probe specifically binds.

The present invented polynucleotide (A) can also be prepared by performing chemical synthesis of a nucleic acid having a target base sequence in accordance with a usual method such as, for example, the phosphite-triester method (Hunkapiller, M. et al., Nature, 310, 105, 1984), based on its base sequence.

The present invented polynucleotide (A) can also be prepared by selecting, as a codon encoding any one of the above amino acid sequences (A1) to (A5), a codon so that the frequency of use of codon corresponds to that in E. coli to design a base sequence, and by chemically synthesizing a polynucleotide composed of the base sequence thus designed.

Specifically, for example, a codon corresponding to each amino acid contained in an amino acid sequence represented by SEQ ID NO: 3 is selected so that the frequency of use of codon is close to that in a microbial cell to be expressed (e.g., E. coli) to design a base sequence encoding a target amino acid sequence. Information on the frequency of use of codon in E. coli, etc. can be obtained by, for example, using the DNA database well known for a person skilled in the art (GenBank, EMBL, DDBJ, and the like).

Specific procedures will be described below.

The number of respective amino acids contained in a target amino acid sequence is calculated. Codons to be used are assigned to the amino acids with the number calculated above so that the frequency is closest to the mean appearance frequency of codon in a microbial cell in which a polynucleotide is expressed. The use order of each codon is assigned so that the same codon is not consecutive as possible. From an amino acid at the N-terminal side in order, a codon is selected for each amino acid in the determined order, and is tentatively determined as a codon of its amino acid residue. By repeating these procedures, codons of all amino acids up to the C terminus are tentatively determined, and finally a termination codon is placed. With respect to a base sequence composed of the tentatively determined codons, the fact that a base sequence inhibiting the transcription of genes in a microbial cell and a base sequence recognized by restriction enzymes to be used in the subsequent operations do not exist is confirmed. If such base sequence exists, the codon involved in this base sequence is replaced by a codon used in other parts. In such base sequence design, it is preferable to add a base sequence recognized by appropriate restriction enzymes to the 5' end side and the 3' end side for the subsequent operations.

Synthesis of a polynucleotide having a base sequence designed in this way can be performed by the long-chain DNA synthesis method using PCR (Cell Engineering Supplement, Plant Cell Engineering Series 7 "PCR Experimental Protocol for Plants", p 95-100, supervised by Takumi Shimamoto and Takuji Sasaki, Shujunsha Co., Ltd., published on Jul. 1, 1997) (hereinafter this method is sometimes referred to as the assembly PCR method). In the method, DNA is synthesized using only a long synthetic oligonucleotide primer. A primer pair is synthesized so that the 3' end of each primer has a complementary strand or an overlap of about 10 bp to about 12 bp, and DNA synthesis is performed using mutual primers as a template. Examples of the full length of the primer can include about 60 mer to about 100 mer. Preferably, examples thereof include about 80 mer to about 100 mer.

By binding these oligonucleotide primers in order by PCR reaction, DNA having a target base sequence is obtained. The DNA thus obtained is introduced into a cloning vector and cloned in accordance with a conventional method. The base sequence of the clone thus obtained is confirmed with a DNA sequencer, and the fact that a polynucleotide having the target base sequence was obtained is confirmed. In this way, the present invented polynucleotide (A) can be obtained by, for example, artificially synthesizing a polynucleotide having a base sequence represented by SEQ ID NO: 13.

The present invented polynucleotide (B) encodes any one of the following amino acid sequences (B1) to (B4):
(B1) an amino acid sequence represented by SEQ ID NO: 1,
(B2) an amino acid sequence ii having at least 95% sequence identity to an amino acid sequence represented by SEQ ID NO: 1, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, (B3) an amino acid sequence represented by i) SEQ ID NO: 1 in which one or plural amino acids are deleted, substituted, or added, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or (B4) an amino acid sequence i) encoded by a polynucleotide hybridized under a stringent condition to a polynucleotide composed of a sequence complementary to a base sequence represented by SEQ ID NO: 2, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative.

The present invented protein (B) has any one of the above amino acid sequences (B1) to (B4).

A difference which is sometimes observed between an amino acid sequence encoded by the present invented polynucleotide (B) or an amino acid sequence of the present invented protein (B) and an amino acid sequence represented by SEQ ID) NO: 1 is deletion, substitution, or addition, etc. of some amino acids (hereinafter sometimes generally referred to as alteration of an amino acid). The "addition" includes not only addition of an amino acid to the end of a sequence but also insertion of an amino acid into a sequence. Examples of the alteration of an amino acid can include (a) deletion by intracellular processing of a protein having an amino acid sequence represented by SEQ ID NO: 1, (b) deletion, substitution, or addition of an amino acid as a result of a naturally occurring gene mutation due to the species difference or individual difference of an organism from which the protein is derived, or (c) deletion, substitution, or addition of an amino acid occurring due to a mutation of an artificially introduced gene, etc.

The number of amino acids to be altered is not limited as long as the number is within a range so that a protein having the above altered amino acid sequence can exert the same ability as that of a protein before alteration, namely any one or both of the ability to oxidize a 2-hydroxy-4-(methylthio) butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative.

Examples of "plural amino acids" in the amino acid sequence (B3) encoded by the present invented polynucleotide (B) or the amino acid sequence (B3) of the present invented protein (B) include 2, 3, 4, 5, 6, 7, 8, 10, 12, 15, or 17 amino acids.

Examples of the substitution of an amino acid include conservative substitution to an amino acid having similar hydrophobicity, electric charge, pK, conformational characteristics, or the like. Specific examples of such substitution include substitution of (1) glycine, alanine; (2) valine, isoleucine, leucine; (3) aspartic acid, glutamic acid, asparagine, glutamine, (4) serine, threonine; (5) lysine, arginine; (6) phenylalanine, tyrosine; and the like in the group.

Examples of the addition of an amino acid can include addition of about 7 to 25 residues of amino acid including about consecutive 6 residues of histidine to the amino terminus or carboxy terminus of an amino acid sequence of a protein. More specific examples can include addition of an amino acid sequence represented by SEQ ID NO: 44 to the amino terminus of an amino acid sequence of a protein, and addition of an amino acid sequence represented by SEQ ID NO: 45 to the carboxy terminus of an amino acid sequence of a protein.

Examples of "at least 95% sequence identity" in the amino acid sequence (B2) encoded by the present invented polynucleotide (B) or the amino acid sequence (B2) of the present invented protein (B) include at least 95, 98, or 99% sequence identity.

In an amino acid sequence encoded by the present invented polynucleotide (B) or an amino acid sequence of the present invented protein (B), "polynucleotide hybridized under a stringent condition to a polynucleotide composed of a sequence complementary to a base sequence represented by SEQ ID NO: 2" means a polynucleotide (1) which form a hybrid by base pairing with a polynucleotide composed of a sequence complementary to a base sequence represented by SEQ ID NO: 2 by being hybridized at 65° C. under a high ionic concentration [for example, 6×SSC (900 mM sodium chloride and 90 mM sodium citrate)] and (2) in which the hybrid is maintained even after being incubated at 65° C. for 30 minutes under a low ionic concentration [for example, 0.1×SSC (15 mM sodium chloride and 1.5 mM sodium citrate)] in the Southern hybridization mentioned in, for example, "Cloning and Sequence" (supervised by Itaru Watanabe, edited by Masahiro Sugiura, 1989, published by Nosonbunka-sha), etc.

Specific examples of the above polynucleotide include a polynucleotide having a base sequence represented by SEQ ID NO: 2, a polynucleotide having a base sequence represented by SEQ ID NO: 2 in which some bases are deleted, substituted, or added, or a polynucleotide having a base sequence having at least 95%, 98%, or 99% sequence identity to a base sequence represented by SEQ ID NO: 2.

The present invented polynucleotide (B) may be a polynucleotide cloned from DNAs existing in the natural world, a polynucleotide into which deletion, substitution, or addition of some bases in a base sequence of this cloned polynucleotide is artificially introduced, or a chemically synthesized polynucleotide.

The present invented polynucleotide (B) can be obtained from, for example, a microorganism having the ability to oxidize α-hydroxycarboxylic acid to corresponding α-oxo-carboxylic acid, and specifically, a microorganism belonging to the genus *Achromobacter* such as an *Achromobacter denitrificans* ATCC55564 strain.

For example, a DNA library is prepared from a microorganism belonging to the genus *Achromobacter* such as *Achromobacter denitrificans*, etc. in accordance with a usual genetic engineering method (e.g., the method mentioned in "New Cell Engineering Experimental Protocol" (edited by Department of Oncology, Institute of Medical Science, the University of Tokyo, Shujunsha Co., Ltd., 1993)). Then, by performing PCR using the DNA library thus prepared as a template and using an appropriate primer, a polynucleotide encoding an amino acid sequence represented by SEQ ID NO: 1, a polynucleotide encoding an amino acid sequence represented by SEQ ID NO: 1 in which one or plural amino acids are deleted, substituted, or added, or a polynucleotide having a base sequence represented by SEQ ID NO: 2, etc. is amplified, and thereby the present invented polynucleotide (B) can be prepared.

A restriction enzyme recognition sequence, etc. may be added to the 5' end side, the 3' end side, or both of a primer used for the above PCR.

For example, by performing PCR using the above DNA library as a template and using an oligonucleotide having a base sequence represented by SEQ ID NO: 9 and an oligonucleotide having a base sequence represented by SEQ ID NO: 10 as a primer, a polynucleotide composed of a base sequence represented by SEQ ID NO: 2 can be amplified.

Examples of a condition for the above PCR include a condition in which a reaction solution prepared by mixing 20 μM each of 4 dNTPs, 15 pmol each of 2 oligonucleotide primers, 1.3 U of a Taq polymerase, and a DNA library as a template is incubated at 94° C. for 2 minutes, and then an incubation cycle consisting of incubation at 94° C. for 10 seconds, followed by 65° C. for 30 seconds, followed by 72° C. for 90 seconds is performed 10 times, subsequently an incubation cycle consisting of incubation at 94° C. for 10 seconds, followed by 65° C. for 30 seconds, followed by 72° C. for one minute and 5 seconds is performed 20 times, and further the solution is maintained at 72° C. for 7 minutes.

Also by performing PCR using the above DNA library as a template and using an oligonucleotide having a partial base sequence selected from a base sequence encoding an amino acid sequence represented by SEQ ID NO: 1 (e.g., an oligonucleotide composed of a base sequence of at least about 14 bases at the 5' end of a base sequence encoding an amino acid sequence represented by SEQ ID NO: 1) and an oligonucleotide of at least about 14 bases composed of a base sequence complementary to a base sequence near the DNA insertion site of the vector used for the DNA library construction as a primer, a polynucleotide having a base sequence encoding an amino acid sequence represented by SEQ ID NO: 1, or a polynucleotide having a base sequence encoding an amino acid sequence represented by SEQ ID NO: 1 in which one or plural amino acids are deleted, substituted, or added, etc. is amplified, and thereby the present invented polynucleotide (B) can be prepared.

The present invented polynucleotide (B) can also obtained by, for example, hybridizing, as a probe, DNA composed of a base sequence of at least about 15 bases having a partial base sequence selected from a base sequence encoding an amino acid sequence represented by SEQ ID NO: 1 to a DNA library into which a vector derived from a microorganism or a phage is inserted under the condition mentioned above to detect DNA to which the probe specifically binds.

The present invented polynucleotide (B) can also be prepared by performing chemical synthesis of a nucleic acid having a target base sequence in accordance with a usual method such as, for example, the phosphite-triester method (Hunkapiller, M. et al., Nature, 310, 105, 1984), based on its base sequence.

The present invented polynucleotide (B) can also be prepared by selecting, as a codon encoding any one of the above amino acid sequences (B1) to (B4), a codon so that the frequency of use of codon corresponds to that in *E. coli* to design a base sequence, and by chemically synthesizing a polynucleotide composed of the base sequence thus designed.

Specifically, for example, a codon corresponding to each amino acid contained in an amino acid sequence represented by SEQ ID NO: 1 is selected so that the frequency of use of codon is close to that in a microbial cell to be expressed (e.g., *E. coli*) to design a base sequence encoding a target amino acid sequence.

The polynucleotide prepared as mentioned above can be cloned into a vector in accordance with the method mentioned in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X, and the like.

The base sequence of the polynucleotide prepared as mentioned above can be analyzed by the dideoxy terminator method, etc. mentioned in F. Sanger, S. Nicklen, A. R. Coulson, Proceeding of Natural Academy of Science U.S.A. (1977) 74: 5463-5467, etc. For sample preparation for base sequence analysis, for example, a commercial reagent such as ABI PRISM Dye Terminator Cycle Sequencing Ready Reaction Kit by PerkinElmer Inc. may be used.

The fact that the polynucleotide prepared as mentioned above encodes an amino acid sequence of a protein having the ability to oxidize α-hydroxycarboxylic acid (e.g., 2-hydroxy-4-(methylthio)butyric acid or α-hydroxy-isocaproic acid) and convert the same into corresponding α-oxocarboxylic acid (e.g., 2-oxo-4-(methylthio)butyric acid or α-oxo-isocaproic acid) can be confirmed by, for example, the following procedures.

The polynucleotide obtained as mentioned above is inserted into a vector so that the polynucleotide is connected downstream of a promoter which can function in a host cell, and the recombinant vector thus obtained is introduced into a host cell to obtain a transformant. A cultured product of the transformant thus obtained is reacted with α-hydroxycarboxylic acid (e.g., 2-hydroxy-4-(methylthio)butyric acid or α-hydroxy-isocaproic acid). By analyzing the amount of corresponding α-oxocarboxylic acid in the reaction product (e.g., 2-oxo-4-(methylthio)butyric acid or α-oxo-isocaproic acid), the fact that the polynucleotide thus obtained encodes an amino acid sequence of a protein having target ability can be confirmed.

To express the present invented polynucleotide (A) or the present invented polynucleotide (B) in a host cell, for example, a polynucleotide in which a promoter which can function in a host cell is connected with the present invented polynucleotide (A) or the present invented polynucleotide (B) so that they can function is prepared, and introduced into a host cell.

Examples of the promoter which can function in a microorganism include a synthetic promoter which can function in *E. coli* as mentioned above. A promoter which controls the expression of the present invented polynucleotide (A) or the present invented polynucleotide (B) in *Achromobacter denitrificans* may be used.

The present invented recombinant (A) can be prepared by integrating the present invented polynucleotide (A), or a polynucleotide in which a promoter which can function in a host cell is connected with the present invented polynucleotide (A) so that they can function into a vector.

The present recombinant vector (B) can be prepared by integrating the present invented polynucleotide (B), or a polynucleotide in which a promoter which can function in a host cell is connected with the present invented polynucleotide (B) so that they can function into a vector.

The present invented recombinant vector (AB) can be prepared by integrating:
i) the present invented polynucleotide (A), or a polynucleotide in which a promoter which can function in a host cell is connected with the present invented polynucleotide (A) so that they can function; and
ii) the present invented polynucleotide (B), or a polynucleotide in which a promoter which can function in a host cell is connected with the present invented polynucleotide (B) so that they can function;
into a vector.

The present invented recombinant vector (AB) can also further include a polynucleotide encoding an amino acid sequence of a protein having the ability to aminate an α-oxocarboxylic acid compound and convert the same into a corresponding L-α-amino acid compound (hereinafter sometimes referred to as the present protein (C)), or a polynucleotide in which the polynucleotide is connected with a promoter which can function in a host cell so that they can function.

For example, the present invented recombinant vector (ABC) can be prepared by integrating
a) the present invented polynucleotide (A), or a polynucleotide in which a promoter which can function in a host cell is connected with the present invented polynucleotide (A) so that they can function;
b) the present invented polynucleotide (B), or a polynucleotide in which a promoter which can function in a host cell is connected with the present invented polynucleotide (B) so that they can function; and
c) a polynucleotide encoding an amino acid sequence of the present protein (C), or a polynucleotide in which the polynucleotide is connected with a promoter which can function in a host cell so that they can function;
into a vector.

Examples of the protein having the ability to aminate an α-oxocarboxylic acid compound and convert the same into a corresponding L-α-amino acid compound include an amino acid dehydrogenase and an aminotransferase. Specific examples of the amino acid dehydrogenase can include an alanine dehydrogenase, a glutamic acid dehydrogenase, a leucine dehydrogenase, and a phenylalanine dehydrogenase, and preferably a leucine dehydrogenase.

More specific examples of the above protein having the ability to aminate an α-oxocarboxylic acid compound and convert the same into a corresponding L-α-amino acid compound can include a leucine dehydrogenase derived from a *Bacillus sphaericus* IFO03525 strain mentioned in Journal of Molecular Catalysis B: Enzymatic 23 (2003) 239-247, and a protein having an amino acid sequence of the leucine dehydrogenase in which the 113th alanine is converted to glycine.

An amino acid sequence represented by SEQ ID NO: 42 is an amino acid sequence of a leucine dehydrogenase derived from a *Bacillus sphaericus* IFO3525 strain mentioned in Journal of Molecular Catalysis B: Enzymatic 23 (2003) 239-247.

An amino acid sequence represented by SEQ ID NO: 7 is an amino acid sequence represented by SEQ ID NO: 42 in which the 113th alanine is converted to glycine.

Specific examples of the amino acid sequence of a protein having the ability to aminate an α-oxocarboxylic acid compound and convert the same into a corresponding L-α-amino acid compound can also include any one of the following amino acid sequences (C1) to (C3):
(C1) an amino acid sequence represented by SEQ ID NO: 7,
(C2) an amino acid sequence i) having at least 90% sequence identity to an amino acid sequence represented by SEQ ID NO: 7, and ii) of a protein having the ability to aminate an α-oxocarboxylic acid compound and convert the same into a corresponding L-α-amino acid compound, or
(C3) an amino acid sequence i) represented by SEQ ID NO: 7 in which one or plural amino acids are deleted, substituted, or added, and ii) of a protein having the ability to aminate an α-oxocarboxylic acid compound and convert the same into a corresponding L-α-amino acid compound.

A difference which is sometimes observed between the amino acid sequence of the present protein (C) and an amino acid sequence represented by SEQ ID NO: 7 is deletion, substitution, or addition, etc. of some amino acids. The "addition" includes not only addition of an amino acid to the end of a sequence but also insertion of an amino acid into a sequence. Examples of the alteration of an amino acid can include (a) deletion by intracellular processing of a protein having an amino acid sequence represented by SEQ ID NO: 7, (b) deletion, substitution, or addition of an amino acid as a result of a naturally occurring gene mutation due to the species difference or individual difference of an organism from which the protein is derived, or (c) deletion, substitution, or addition of an amino acid occurring due to a mutation of an artificially introduced gene, etc.

The number of amino acids to be altered is not limited as long as the number is within a range so that a protein having the above altered amino acid sequence can exert the ability to aminate an α-oxocarboxylic acid compound and convert the same into a corresponding L-α-amino acid compound. Examples of "plural amino acids" in the above amino acid sequence (C3) of the present protein (C) include 2, 3, 4, 5, 6, 7, 10, 15, 18, 20, 25, 30, 35, 36, or 40 amino acids.

Examples of the substitution of an amino acid include conservative substitution to an amino acid having similar hydrophobicity, electric charge, pK, conformational characteristics, or the like. Specific examples of such substitution include substitution of (1) glycine, alanine; (2) valine, isoleucine, leucine; (3) aspartic acid, glutamic acid, asparagine, glutamine, (4) serine, threonine; (5) lysine, arginine; (6) phenylalanine, tyrosine; and the like in the group.

Examples of the addition of an amino acid can include addition of about 20 residues of amino acid including about consecutive 6 residues of histidine to the amino terminus or carboxy terminus of an amino acid sequence. More specific examples can include addition of an amino acid sequence represented by SEQ ID NO: 44 to the amino terminus of an amino acid sequence of a protein, and addition of an amino acid sequence represented by SEQ ID NO: 45 to the carboxy terminus of an amino acid sequence of a protein.

Examples of "at least 90% sequence identity" in the above amino acid sequence (C2) of the present protein (C) include at least 90, 95, 98, or 99% sequence identity.

A polynucleotide encoding an amino acid sequence of a protein having the ability to aminate an α-oxocarboxylic acid compound and convert the same into a corresponding L-α-amino acid compound (hereinafter sometimes referred to as the present polynucleotide (C)) can be obtained from, for example, a microorganism having the ability to aminate an α-oxocarboxylic acid compound and convert the same into a corresponding L-α-amino acid compound, for example, a microorganism belonging to the genus *Bacillus* such as a *Bacillus sphaericus* IFO3525 strain.

A DNA library is prepared from a microorganism belonging to the genus *Bacillus* such as a *Bacillus sphaericus* IFO3525 strain, etc. in accordance with a usual genetic engineering method. Then, by performing PCR using the DNA library thus prepared as a template and using an appropriate primer, a polynucleotide encoding an amino acid sequence represented by SEQ ID NO: 42, or a polynucleotide encoding an amino acid sequence represented by SEQ ID NO: 42 in which one or plural amino acids are deleted, substituted, or added, etc. is amplified, and thereby the present polynucleotide (C) can be prepared.

For example, as a primer for amplification of a polynucleotide having a base sequence represented by SEQ ID NO: 43 encoding an amino acid sequence represented by SEQ ID NO: 42, an oligonucleotide having a base sequence represented by SEQ ID NO: 14 and an oligonucleotide having a base sequence represented by SEQ ID NO: 15 are synthesized. As a primer for mutation introduction for converting the 113th alanine in an amino acid sequence represented by SEQ ID NO: 42 to glycine, an oligonucleotide having a base sequence represented by SEQ ID NO: 16 and an oligonucleotide having a base sequence represented by SEQ ID NO: 17 are synthesized.

By performing PCR using the above DNA library as a template and using an oligonucleotide having a base sequence represented by SEQ ID NO: 14 and an oligonucleotide having a base sequence represented by SEQ ID NO: 15 as a primer, a polynucleotide having a base sequence represented by SEQ ID NO: 43 is amplified. The polynucleotide thus amplified is integrated into a vector to obtain a recombinant vector containing a polynucleotide having a base sequence represented by SEQ ID NO: 43. PCR is performed using the recombinant vector thus obtained as a template and using an oligonucleotide having a base sequence represented by SEQ ID NO: 16 and an oligonucleotide having a base sequence represented by SEQ ID NO: 17 as a primer, and the PCR product thus obtained is processed with Dpn I, and then introduced into E. coli. The base sequence of the recombinant vector of the transformant thus obtained is analyzed to obtain a polynucleotide encoding an amino acid sequence into which the target amino acid mutation is introduced, namely an amino acid sequence represented by SEQ ID NO: 42 in which the 113th alanine is substituted by glycine (an amino acid sequence represented by SEQ ID NO: 7). Examples of a base sequence encoding an amino acid sequence represented by SEQ ID NO: 7 include a base sequence represented by SEQ ID NO: 8.

The present polynucleotide (C) can also be prepared by performing chemical synthesis of a nucleic acid having a target base sequence in accordance with a usual method such as, for example, the phosphite-triester method (Hunkapiller, M. et al., Nature, 310, 105, 1984), based on its base sequence.

The present polynucleotide (C) can also be prepared by selecting, as a codon encoding any one of the above amino acid sequences (C1) to (C3), a codon so that the frequency of use of codon corresponds to that in E. coli to design a base sequence, and by chemically synthesizing a polynucleotide composed of the base sequence thus designed.

To express the present polynucleotide (C) in a host cell, for example, a polynucleotide in which a promoter which can function in a host cell is connected with the present polynucleotide (C) so that they can function is prepared, and introduced into a host cell.

Examples of the promoter which can function in a microorganism include a synthetic promoter which can function in E. coli as mentioned above. A promoter which controls the expression of the present polynucleotide (C) in a microorganism belonging to the genus Bacillus such as Bacillus sphaericus may be used.

The fact that the polynucleotide prepared as mentioned above encodes an amino acid sequence of a protein having the ability to aminate an α-oxocarboxylic acid compound (e.g., 2-oxo-4-(methylthio)butyric acid or α-oxo-isocaproic acid) and convert the same into a corresponding L-α-amino acid compound (e.g., L-methionine or L-leucine) can be confirmed by, for example, the following procedures.

The polynucleotide obtained as mentioned above is inserted into a vector so that the polynucleotide is connected downstream of a promoter which can function in a host cell, and the recombinant vector thus obtained is introduced into a host cell to obtain a transformant. A cultured product of the transformant thus obtained is reacted with α-oxocarboxylic acid (e.g., 2-oxo-4-(methylthio)butyric acid or α-oxo-isocaproic acid). By analyzing the amount of corresponding L-α-amino acid in the reaction product (e.g., L-methionine or L-leucine), the fact that the polynucleotide thus obtained encodes an amino acid sequence of a protein having target ability can be confirmed.

A transformant can be produced by introducing the present invented polynucleotide (A), the present invented polynucleotide (B), or the present polynucleotide (C), or a recombinant vector containing at least one of these polynucleotides into a host cell.

Examples of the host cell include a microorganism belonging to the genus Escherichia, Bacillus, Corynebacterium, Staphylococcus, Streptomyces, Saccharomyces, Kluyveromyces, Pichia, Rhodococcus, or Aspergillus.

As mentioned above, by introducing the present invented polynucleotide (A), or a polynucleotide in which a promoter which can function in a host cell is connected with the present invented polynucleotide (A) so that they can function into a host cell, a transformant having the present invented polynucleotide (A), or a polynucleotide in which a promoter which can function in a host cell is connected with the present invented polynucleotide (A) so that they can function can be obtained. Examples of the transformant can also include a transformant in which the above exogenous polynucleotide is introduced into a chromosome of a host cell, namely a transformant having the above exogenous polynucleotide on a chromosome.

By introducing the present invented polynucleotide (B), or a polynucleotide in which a promoter which can function in a host cell is connected with the present invented polynucleotide (B) so that they can function into a host cell, a transformant having the present invented polynucleotide (B), or a polynucleotide in which a promoter which can function in a host cell is connected with the present invented polynucleotide (B) so that they can function can be obtained. Examples of the transformant can also include a transformant in which the above exogenous polynucleotide is introduced into a chromosome of a host cell, namely a transformant having the above exogenous polynucleotide on a chromosome.

As mentioned above, by introducing
a) the present invented polynucleotide (A), or a polynucleotide in which a promoter which can function in a host cell is connected with the present invented polynucleotide (A) so that they can function;
b) the present invented polynucleotide (B), or a polynucleotide in which a promoter which can function in a host cell is connected with the present invented polynucleotide (B) so that they can function; and
c) a polynucleotide encoding an amino acid sequence of the present protein (C), or a polynucleotide in which the polynucleotide is connected with a promoter which can function in a host cell so that they can function;
into a host cell, a transformant having:
a) the present invented polynucleotide (A), or a polynucleotide in which a promoter which can function in a host cell is connected with the present invented polynucleotide (A) so that they can function;
b) the present invented polynucleotide (B), or a polynucleotide in which a promoter which can function in a host cell is connected with the present invented polynucleotide (B) so that they can function; and
c) a polynucleotide encoding an amino acid sequence of the present protein (C), or a polynucleotide in which the polynucleotide is connected with a promoter which can function in a host cell so that they can function;

can be obtained.

The above a) polynucleotide, b) polynucleotide, and c) polynucleotide may be separately integrated into a different vector and introduced into a host cell, or one or more of these may be integrated into the same vector and introduced into a host cell. When one or more polynucleotides are integrated into a single vector, for example, the polynucleotide(s) may be integrated into a vector by linking a region involved in the expression control such as a promoter and a terminator to each of target polynucleotides, or the polynucleotide(s) may be integrated into a vector as an operon containing plural cistrons such as a lactose operon so that target polynucleotides are expressed. Any one or one or more of the above a) polynucleotide, b) polynucleotide, and c) polynucleotide may be on a chromosome of a host cell.

The present invented protein (A) can be produced by, for example, culturing a transformant having the present invented polynucleotide (A) to express the present invented protein (A).

The present invented protein (B) can be produced by, for example, culturing a transformant having the present invented polynucleotide (B) to express the present invented protein (B).

The present protein (C) can be produced by, for example, culturing a transformant having the present polynucleotide (C) to express the present protein (C).

As a method for purifying the present invented protein (A), the present invented polynucleotide (B), or the present protein (C) from a cultured product of a transformant having the present invented polynucleotide (A), the present invented polynucleotide (B), or the present protein (C), a usual method used for purification of proteins can be applied.

A fraction containing the present invented protein (A) and a fraction containing the present invented protein (B) can be selected by, for example, using the ability to oxidize 2-hydroxy-4-(methylthio)butyric acid and preferentially produce 2-oxo-4-(methylthio)butyric acid or the ability to oxidize α-hydroxy-isocaproic acid and preferentially produce α-oxo-isocaproic acid as an index.

A fraction containing the present protein (C) can be selected by, for example, using the ability to aminate 2-oxo-4-(methylthio)butyric acid and preferentially produce L-methionine or the ability to aminate α-oxo-isocaproic acid and preferentially produce L-leucine as an index.

The present invented production method is a method for producing an L-α-amino acid compound, which includes:
(1) the step of reacting any one or both of the present invented protein (A) and the present invented protein (B) with an α-hydroxycarboxylic acid compound to obtain a corresponding α-oxocarboxylic acid compound, and
(2) the step of reacting a protein having the ability to aminate an α-oxocarboxylic acid compound and convert the same into a corresponding L-α-amino acid compound with the α-oxocarboxylic acid compound obtained in the step (1) to obtain a corresponding L-α-amino acid compound.

Examples of the above α-hydroxycarboxylic acid include α-hydroxycarboxylic acid represented by formula (4):

$$R^2—CH(OH)COOH \tag{4}$$

wherein $R^2$ represents a hydrogen atom, a C1-10 linear, branched-chain, or cyclic alkyl group, or a C1-10 linear or branched-chain alkyl group having a substituent of amide, amino, monoalkylamino, dialkylamino, monoalkylamide, dialkylamide, alkoxy, alkylthio, hydroxy, mercapto, carboxyl, or alkoxycarbonyl, or a 1H-imidazolyl group, a phenyl group, a 3'-indolyl group, a p-hydroxyphenyl group, or a p-alkoxyphenyl group, and the number of carbon atoms in alkyl and alkoxy included in the substituent is 1-3 each.

Examples of the above L-α-amino acid compound include L-asparagine, L-aspartic acid, L-cysteine, L-glutamine, L-glutamic acid, L-histidine, L-serine, L-threonine, L-tryptophan, L-tyrosine, L-alanine, glycine, L-isoleucine, L-leucine, L-methionine, L-phenylalanine, and L-valine, and preferably L-alanine, glycine, L-isoleucine, L-leucine, L-methionine, L-phenylalanine, or L-valine.

Examples of the above α-hydroxycarboxylic acid compound can preferably include α-hydroxy-isocaproic acid, examples of the corresponding α-oxocarboxylic acid compound can include α-oxo-isocaproic acid, and examples of the corresponding L-α-amino acid compound can include L-leucine.

Examples of the above α-hydroxycarboxylic acid compound can also preferably include a sulfur-containing α-hydroxycarboxylic acid compound, examples of the corresponding α-oxocarboxylic acid compound can include a sulfur-containing α-oxocarboxylic acid compound, and examples of the corresponding L-α-amino acid compound can include a sulfur-containing L-α-amino acid compound.

Examples of the above sulfur-containing α-hydroxycarboxylic acid compound include sulfur-containing α-hydroxycarboxylic acid represented by formula (1):

wherein $R^1$ represents a hydrogen atom or an optionally substituted C1-8 alkyl group.

Examples of a sulfur-containing α-oxocarboxylic acid compound obtained by reacting the above sulfur-containing α-hydroxycarboxylic acid represented by formula (1) with any one or both of the present invented protein (A) and the present invented protein (B) include sulfur-containing α-oxocarboxylic acid represented by formula (2):

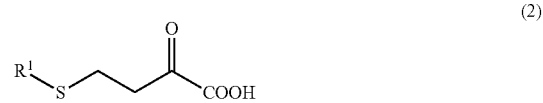

wherein $R^1$ is the same as defined above.

Examples of a sulfur-containing L-α-amino acid compound obtained by reacting the above sulfur-containing α-oxocarboxylic acid represented by formula (2) with the present protein (C) include sulfur-containing L-α-amino acid represented by formula (3):

In the sulfur-containing α-hydroxycarboxylic acid represented by formula (1), the sulfur-containing α-oxocarboxylic acid represented by formula (2), and the sulfur-containing L-α-amino acid represented by formula (3), examples of a C1-8 alkyl group in the C1-8 alkyl group which is optionally substituted represented by $R^1$ include a methyl group, an ethyl group, a propyl group, an isopropyl group, a butyl group, a pentyl group, a hexyl group, a heptyl group, and an octyl group.

Specific examples of the sulfur-containing α-hydroxycarboxylic acid represented by formula (1) can include 2-hydroxy-4-(methylthio)butyric acid, 2-hydroxy-4-(ethylthio)butyric acid, 2-hydroxy-4-(propylthio)butyric acid, 2-hydroxy-4-(butylthio)butyric acid, 2-hydroxy-4-(pentylthio)butyric acid, 2-hydroxy-4-(hexylthio)butyric acid, 2-hydroxy-4-(heptylthio)butyric acid, and 2-hydroxy-4-(octylthio)butyric acid.

Specific examples of the sulfur-containing α-oxo carboxylic acid represented by formula (2) can include 2-oxo-4-(methylthio)butyric acid, 2-oxo-4-(ethylthio)butyric acid, 2-oxo-4-(propylthio)butyric acid, 2-oxo-4-(butylthio)butyric acid, 2-oxo-4-(pentylthio)butyric acid, 2-oxo-4-(hexylthio)butyric acid, 2-oxo-4-(heptylthio)butyric acid, and 2-oxo-4-(octylthio)butyric acid.

Specific examples of the sulfur-containing L-α-amino acid represented by formula (3) can include 2-amino-4-(methylthio)butyric acid, 2-amino-4-(ethylthio)butyric acid, 2-amino-4-(propylthio)butyric acid, 2-amino-4-(butylthio)butyric acid, 2-amino-4-(pentylthio)butyric acid, 2-amino-4-(hexylthio)butyric acid, 2-amino-4-(heptylthio)butyric acid, and 2-amino-4-(octylthio)butyric acid.

As the C1-8 alkyl group which is optionally substituted represented by $R^1$, a methyl group is preferable, and as the sulfur-containing α-hydroxycarboxylic acid represented by formula (1), 2-hydroxy-4-(methylthio)butyric acid is preferably exemplified.

In the step (1) of the present invented production method, when α-hydroxy-isocaproic acid is used as a substrate, α-oxo-isocaproic acid is obtained in the step (1) and L-leucine is obtained in the step (2).

In the step (1) of the present invented production method, when 2-hydroxy-4-(methylthio)butyric acid is used as a substrate, 2-oxo-4-(methylthio)butyric acid is obtained in the step (1) and L-methionine is obtained in the step (2).

In the step (1) of the present invented production method, each of the present invented protein (A) and the present invented protein (B) can be provided to a reaction system for reaction with an α-hydroxycarboxylic acid compound, in various forms. Each of the present invented protein (A) and the present invented protein (B) may be provided to a reaction system in the step (1) of the present invented production method in the form of a purified protein, or may be provided to the reaction system in the form in which the protein is included in a microorganism producing the protein or in a treated product of the microorganism. "Treated product of microorganism" means that prepared in a similar manner to the above mentioned "treated product of transformant". Each of the present invented protein (A) and the present invented protein (B) may be provided to the above reaction system in the form in which the protein is included in a transformant in which a polynucleotide encoding the protein is introduced into a host cell or in a treated product thereof.

To react the present invented protein (A) with an α-hydroxycarboxylic acid compound, specifically, for example, the present invented protein (A), an immobilized product of the present invented protein (A), a cultured product of a transformant producing the present invented protein (A) in which a polynucleotide encoding the present invented protein (A) is introduced into a host cell, or a treated product of the transformant can be provided to a reaction system in the step (i) of the present invented production method.

To react the present invented protein (B) with an α-hydroxycarboxylic acid compound, specifically, for example, the present invented protein (B), an immobilized product of the present invented protein (B), a cultured product of a transformant producing the present invented protein (B) in which a polynucleotide encoding the present invented protein (B) is introduced into a host cell, or a treated product of the transformant can be provided to a reaction system in the step (1) of the present invented production method.

A transformant in which a polynucleotide encoding the present invented protein (A) is introduced into a host cell or a treated product thereof, and a transformant in which a polynucleotide encoding the present invented protein (B) is introduced into a host cell or a treated product thereof may be provided to a reaction system in the step (1) of the present invented production method. A transformant in which both of a polynucleotide encoding the present invented protein (A) and a polynucleotide encoding the present invented protein (B) are introduced into the same host cell or a treated product thereof may be provided to the above reaction system. A polynucleotide encoding the present invented protein (A) and a polynucleotide encoding the present invented protein (B) may be separately integrated into a different vector and introduced into a host cell, or may be integrated into the same vector and introduced into a host cell. When both polynucleotides are integrated into a single vector, for example, the polynucleotides may be integrated into a vector by linking a region involved in the expression control such as a promoter and a terminator to each of both polynucleotides, or the polynucleotides may be integrated into a vector as an operon containing plural cistrons such as a lactose operon so that both polynucleotides are expressed. Any one or both of a polynucleotide encoding the present invented protein (A) and a polynucleotide encoding the present invented protein (B) may be on a chromosome of a host cell.

The step (1) of the present invented production method is usually performed in the presence of water and a coenzyme such as an oxidized β-nicotinamide adenine dinucleotide (hereinafter sometimes referred to as NAD+). Water used in this case may be a buffered aqueous solution. Examples of a buffer used for the buffered aqueous solution include tris(hydroxymethyl)aminomethane, alkali metal phosphates such as sodium phosphate or potassium phosphate, alkali metal acetates such as sodium acetate or potassium acetate, or mixtures thereof.

In the step (1) of the present invented production method, in addition to water, an organic solvent can also coexist in a reaction system. Examples of the organic solvent to be used include ethers such as t-butyl methyl ether, diisopropyl ether, and tetrahydrofuran; esters such as ethyl formate, ethyl acetate, propyl acetate, butyl acetate, ethyl propionate, and butyl propionate; hydrocarbons such as toluene, hexane, cyclohexane, heptane, and isooctane; alcohols such as methanol, ethanol, 2-propanol, butanol, and t-butyl alcohol; organic sulfur compounds such as dimethyl sulfoxide; ketones such as acetone; nitriles such as acetonitrile; and mixtures thereof.

In the step (1) of the present invented production method, since a cofactor is used as a conjugated system, usually it is better to add a coenzyme to a reaction system. Examples of the coenzyme to be added can include oxidized β-nicotinamide adenine dinucleotide (NAD+) and oxidized β-nicotinamide adenine dinucleotide phosphate (hereinafter sometimes referred to as NADP+). The amount of a cofactor in the reaction system is usually equimolar to or more than the amount of an α-hydroxycarboxylic acid compound as a substrate, and the cofactor is preferably added at the start of reaction.

In the step (1) of the present invented production method, as the oxidation reaction of an α-hydroxycarboxylic acid compound (e.g., sulfur-containing α-hydroxycarboxylic acid such as 2-hydroxy-4-(methylthio)butyric acid or α-hydroxy-isocaproic acid) proceeds, NAD+ in the reaction solution is converted into reduced β-nicotinamide adenine dinucleotide (hereinafter sometimes referred to as NADH). Since NADH occurred as a result of the conversion can return to the original NAD+ by being reacted with a protein having the ability to convert NADH into its oxidized form (NAD+), a protein having the ability to convert NADH into NAD+ may further exist in a reaction system in the above step (1). When a protein having the ability to convert NADH into NAD+ further exists in a reaction system in the above step (1), the amount of a cofactor in the reaction system may be usually a catalytic amount, and equimolar to or less than the amount of an α-hydroxycarboxylic acid compound as a substrate.

Examples of the protein having the ability to convert. NADH into NAD+ include organic acid dehydrogenases such as a malate dehydrogenase; a reductase, an alcohol dehydrogenase, an aldehyde dehydrogenase, an amino acid dehydrogenase, or an NADH oxidase. Examples of the amino acid dehydrogenase can include the present protein (C), more specifically, a leucine dehydrogenase of a microorganism belonging to the genus *Bacillus*.

When the protein having the ability to convert NADH into NAD$^+$ is an NADH oxidase, the activity of the protein is sometimes enhanced by coexistence of FAD, etc. in the reaction system, and, for example, FAD, etc. may be added to the reaction solution. When the protein having the ability to convert NADH into NAD$^+$ is an NADH oxidase, oxygen in the reaction solution is consumed and converted into hydrogen peroxide. Since hydrogen peroxide occurred as a result of the conversion can return to the original molecular oxygen by a protein having the ability to convert hydrogen peroxide into molecular oxygen, a protein having the ability to convert hydrogen peroxide into molecular oxygen may further coexist in a reaction system in the above step. Examples of the protein having the ability to convert hydrogen peroxide into molecular oxygen include a catalase.

Each of a protein having the ability to convert NADH into NAD+ and a protein having the ability to convert hydrogen peroxide into molecular oxygen may be provided to a reaction system in the step (1) of the present invented production method in the form of a purified protein or an immobilized product thereof, or may be provided to the reaction system in the form in which the protein is included in a microorganism producing the protein or in a treated product of the microorganism. "Treated product of microorganism" means that prepared in a similar manner to the above mentioned "treated product of transformant". For example, a transformant in which a polynucleotide encoding a protein having the ability to convert NADH into NAD+ is introduced into a host cell or a treated product thereof may be provided to the above reaction system. A transformant in which a polynucleotide encoding a protein having the ability to convert hydrogen peroxide into molecular oxygen is introduced into a host cell or a treated product thereof may be further provided to the above reaction system.

A transformant in which a polynucleotide encoding a protein having the ability to convert NADH into NAD+ is introduced into a host cell or a treated product thereof, and a transformant in which a polynucleotide encoding a protein having the ability to convert hydrogen peroxide into molecular oxygen is introduced into a host cell or a treated product thereof may be provided to the above reaction system.

A transformant in which both of a polynucleotide encoding a protein having the ability to convert NADH into NAD+ and a polynucleotide encoding a protein having the ability to convert hydrogen peroxide into molecular oxygen are introduced in the same host cell or a treated product thereof may be provided to the above reaction system. A polynucleotide encoding a protein having the ability to convert NADH into NAD+ and a polynucleotide encoding a protein having the ability to convert hydrogen peroxide into molecular oxygen may be separately integrated into a different vector and introduced into a host cell, or may be integrated into the same vector and introduced into a host cell. When both polynucleotides are integrated into a single vector, for example, the polynucleotides may be integrated into a vector by linking a region involved in the expression control such as a promoter and a terminator to each of both polynucleotides, or the polynucleotides may be integrated into a vector as an operon containing plural cistrons such as a lactose operon so that both polynucleotides are expressed. Any one or both of a polynucleotide encoding a protein having the ability to convert NADH into NAD+ and a polynucleotide encoding a protein having the ability to convert hydrogen peroxide into molecular oxygen may be on a chromosome of a host cell.

A transformant in which two or more polynucleotides selected from the group consisting of a polynucleotide encoding the present invented protein (A), a polynucleotide encoding the present invented protein (B), a polynucleotide encoding a protein having the ability to convert NADH into NAD+, and a polynucleotide encoding a protein having the ability to convert hydrogen peroxide into molecular oxygen are introduced into the same host cell or a treated product thereof may be provided to the above reaction system.

A reaction in the step (i) of the present invented production method is performed by, for example, mixing water, an α-hydroxycarboxylic acid compound (e.g., a sulfur-containing α-hydroxycarboxylic acid compound such as 2-hydroxy-4-(methylthio)butyric acid or α-hydroxy-isocaproic acid), NAD+, any one or both of the present invented protein (A) and the present invented protein (B) or a transformant producing them or a treated product thereof, and further, as needed, a reaction solution containing an organic solvent, a catalase, and the like by stirring, shaking, and the like.

The pH at the time of reaction in the above method can be appropriately selected, and is usually within a range of about 3 to about 10. The reaction temperature can be appropriately selected, and is usually within a range of about 0° C. to about 60° C. in terms of the stability and the reaction rate of raw materials and products.

As the oxidation reaction of an α-hydroxycarboxylic acid compound (e.g., sulfur-containing α-hydroxycarboxylic acid such 2-hydroxy-4-(methylthio)butyric acid or α-hydroxy-isocaproic acid) proceeds, NAD+ in the reaction solution is converted into NADH. Therefore, when a protein having the ability to convert NADH into NAD+ is not included in a reaction system in the above step (1), the progression of the oxidation reaction can be monitored by, for example, measuring the amount of increase of NADH in the reaction solution per unit time, namely the rate of increase.

The end point of the reaction can be determined by, for example, analyzing the amount of an α-hydroxycarboxylic acid compound (e.g., a sulfur-containing α-hydroxycarboxylic acid compound such as 2-hydroxy-4-(methylthio)butyric acid or α-hydroxy-isocaproic acid) in the reaction solution by liquid chromatography, etc.

The reaction time can be appropriately selected, and is usually within a range of about 0.5 hour to about 10 days.

Recovery of α-oxocarboxylic acid (e.g., a sulfur-containing α-oxocarboxylic acid compound such as 2-oxo-4-(methylthio)butyric acid or α-oxo-isocaproic acid) from the reaction solution may be performed by a generally known arbitrary method.

Example thereof include a method for purifying a target compound by performing post-treatment operations of the reaction solution such as extraction with an organic solvent and concentration in combination with column chromatography, distillation, or the like as needed.

An α-oxocarboxylic acid (e.g., a sulfur-containing α-oxocarboxylic acid compound such as 2-oxo-4-(methylthio) butyric acid or α-oxo-isocaproic acid) obtained in the step (1) of the present invented production method is purified or partially purified from the reaction solution, and then can be subjected to the step (2). By adding the reaction solution in the step (1) to the reaction solution in the step (2), an α-oxocarboxylic acid (e.g., a sulfur-containing α-oxocarboxylic acid compound such as 2-oxo-4-(methylthio)butyric acid or α-oxo-isocaproic acid) obtained in the step (1) can also be subjected to the step (2).

In the step (2) of the present invented production method, the present protein (C) can be provided to a reaction system for reaction with an α-oxocarboxylic acid compound, in various forms. The present protein (C) may be provided to a reaction system in the above step (2) in the form of a purified protein, or may be provided to the reaction system in the form in which the protein is included in a microorganism producing the protein or in a treated product of the microorganism. "Treated product of microorganism" means that prepared in a similar manner to the above mentioned "treated product of transformant". The present protein (C) may be provided to the above reaction system in the form in which the protein is included in a transformant in which a polynucleotide encoding the protein is introduced into a host cell or in a treated product thereof.

To react the present protein (C) with an α-oxocarboxylic acid compound, specifically, for example, the present protein (C), an immobilized product of the present protein (C), a cultured product of a transformant producing the present protein (C) in which a polynucleotide encoding the present protein (C) is introduced into a host cell, or a treated product of the transformant can be provided to a reaction system in the above step (2).

The step (2) of the present invented production method is usually performed in the presence of water, an ammonium ion, and a coenzyme such as NADH.

Water used in this case may be a buffered aqueous solution. Examples of a buffer used for the buffered aqueous solution include tris(hydroxymethyl)aminomethane, alkali metal phosphates such as sodium phosphate or potassium phosphate, alkali metal acetates such as sodium acetate or potassium acetate, or mixtures thereof.

In the step (2) of the present invented production method, in addition to water, an organic solvent can also coexist in a reaction system. Examples of the organic solvent to be used include ethers such as t-butyl methyl ether, diisopropyl ether, and tetrahydrofuran; esters such as ethyl formate, ethyl acetate, propyl acetate, butyl acetate, ethyl propionate, and butyl propionate; hydrocarbons such as toluene, hexane, cyclohexane, heptane, and isooctane; alcohols such as methanol, ethanol, 2-propanol, butanol, and t-butyl alcohol; organic sulfur compounds such as dimethyl sulfoxide; ketones such as acetone; nitriles such as acetonitrile; and mixtures thereof.

In the step (2) of the present invented production method, since an ammonium ion is used as an amino group donor, usually an ammonium salt compound is added to a reaction system. Examples of the ammonium salt compound to be added can include ammonium sulfate, ammonium formate, ammonium chloride, ammonium nitrate, ammonium phosphate, ammonium hydroxide, ammonium tartrate, and ammonium acetate. The amount of an ammonium ion in the reaction system is usually equimolar to or more than the amount of an α-oxocarboxylic acid compound as a substrate, and the ammonium ion is preferably added at the start of reaction.

In the step (2) of the present invented production method, since a cofactor is used as a conjugated system, usually it is better to add a coenzyme to a reaction system. Examples of the coenzyme to be added can include reduced β-nicotinamide adenine dinucleotide and reduced β-nicotinamide adenine dinucleotide phosphate (hereinafter sometimes referred to as NADPH). The amount of a cofactor in the reaction system is usually equimolar to or more than the amount of an α-oxocarboxylic acid compound as a substrate, and the cofactor is preferably added at the start of reaction.

In the step (2) of the present invented production method, as the reductive amination reaction of α-oxocarboxylic acid (e.g., sulfur-containing α-oxocarboxylic acid such as 2-oxo-4-(methylthio)butyric acid or α-oxo-isocaproic acid) proceeds, NADH in the reaction solution is converted into oxidized β-nicotinamide adenine dinucleotide (NAD+). Since NAD+ occurred as a result of the conversion can return to the original NADH by being reacted with a protein having the ability to convert NAD+ into its reduced form (NADH), a protein having the ability to convert NAD+ into NADH may further exist in a reaction system in the above step (2). When a protein having the ability to convert NAD+ into NADH further exists in a reaction system in the above step (2), the amount of a cofactor in the reaction system may be usually a catalytic amount, and equimolar to or less than the amount of an α-oxocarboxylic acid compound as a substrate.

Examples of the protein having the ability to convert NAD+ into NADH include organic acid dehydrogenases such as a formate dehydrogenase and a malate dehydrogenase; a glucose dehydrogenase, an alcohol dehydrogenase, an aldehyde dehydrogenase, or an amino acid dehydrogenase.

A protein having the ability to convert NAD+ into NADH may be provided to a reaction system in the step (2) of the present invented production method in the form of a purified protein or an immobilized product thereof, or may be provided to the reaction system in the form in which the protein is included in a microorganism producing the protein or in a treated product of the microorganism. "Treated product of microorganism" means that prepared in a similar manner to the above mentioned "treated product of transformant". A transformant in which a polynucleotide encoding a protein having the ability to convert NAD+ into NADH is introduced into a host cell or a treated product thereof may be provided to the above reaction system.

In the step (2) of the present invented production method, a transformant in which a polynucleotide encoding the present protein (C) is introduced into a host cell or a treated product thereof, and a transformant in which a polynucleotide encoding a protein having the ability to convert NAD+ into NADH is introduced into a host cell or a treated product thereof may be provided to a reaction system for reaction with an α-oxocarboxylic acid compound.

In the step (2) of the present invented production method, a transformant in which both of a polynucleotide encoding the present protein (C) and a polynucleotide encoding a protein having the ability to convert NAD+ into NADH are introduced in the same host cell or a treated product thereof may be provided to the reaction system. A polynucleotide encoding the present protein (C) and a polynucleotide encoding a protein having the ability to convert NAD+ into NADH may be separately integrated into a different vector and introduced into a host cell, or may be integrated into the same vector and introduced into a host cell. When both polynucleotides are integrated into a single vector, for example, the polynucleotides may be integrated into a vector by linking a region involved in the expression control such as a promoter and a terminator to each of both polynucleotides, or the polynucleotides may be integrated into a vector as an operon containing plural cistrons such as a lactose operon so that both polynucleotides are expressed. Any one or both of a polynucleotide encoding the present protein (C) and a polynucleotide encoding a protein having the ability to convert NAD+ into NADH may be on a chromosome of a host cell.

A reaction in the step (2) of the present invented production method is performed by, for example, mixing water, an ammonium salt compound, NADH, an α-oxocarboxylic acid compound (e.g., a sulfur-containing α-oxocarboxylic acid compound such as 2-oxo-4-(methylthio)butyric acid or α-oxo-isocaproic acid), the present protein (C) or a transformant producing it or a treated product thereof, and further, as needed, a reaction solution containing an organic solvent, a protein having the ability to convert NAD+ into NADH, and the like by stirring, shaking, and the like.

The pH at the time of reaction in the above method can be appropriately selected, and is usually within a range of about 3 to about 10. The reaction temperature can be appropriately selected, and is usually within a range of about 0° C. to about 60° C. in terms of the stability and the reaction rate of raw materials and products.

The end point of the reaction can be determined by, for example, analyzing the amount of an α-oxocarboxylic acid compound (e.g., a sulfur-containing α-oxocarboxylic acid compound such as 2-oxo-4-(methylthio)butyric acid or α-oxo-isocaproic acid) in the reaction solution by liquid chromatography, etc.

The reaction time can be appropriately selected, and is usually within a range of about 0.5 hour to about 10 days.

Recovery of L-α-amino acid (e.g., sulfur-containing L-α-amino acid such as L-methionine or L-leucine) from the reaction solution may be performed by a generally known arbitrary method.

Example thereof include a method for purifying a target compound by performing post-treatment operations of the reaction solution such as filtration, crystallization, extraction with an organic solvent, and concentration in combination with column chromatography, distillation, or the like as needed.

The step (1) and step (2) of the present invented production method can be performed in one reaction system.

In this case, the present invented protein (A), the present invented protein (B), and the present protein (C) can be provided to the above reaction system in different various forms.

The present invented protein (A), the present invented protein (B), and the present protein (C) may be provided to the above reaction system in the form of a purified protein, or may be provided to the above reaction system in the form in which the proteins are included in a microorganism producing these proteins or in a treated product of the microorganism.

The present invented protein (A), the present invented protein (B), and the present protein (C) may be provided to the above reaction system in the form in which the proteins are included in a transformant in which a polynucleotide encoding these proteins is introduced into a host cell or in a treated product thereof.

For example, any one or both of a transformant in which a polynucleotide encoding the present invented protein (A) is introduced into a host cell or a treated product thereof, a transformant in which a polynucleotide encoding the present invented protein (B) is introduced into a host cell or a treated product thereof, and a transformant in which a polynucleotide encoding the present protein (C) is introduced into a host cell or a treated product thereof may be provided to the above reaction system. A transformant in which any one or both of a polynucleotide encoding the present invented protein (A) and a polynucleotide encoding the present invented protein (B) and a polynucleotide encoding the present protein (C) are introduced into the same host cell or a treated product thereof may be provided to the above reaction system. Any one or both of a polynucleotide encoding the present invented protein (A) and a polynucleotide encoding the present invented protein (B) and a polynucleotide encoding the present protein (C) may be separately integrated into a different vector and introduced into a host cell, or may be integrated into the same vector and introduced into a host cell. When plural polynucleotides are integrated into a single vector, for example, the polynucleotides may be integrated into a vector by linking a region involved in the expression control, such as a promoter and a terminator to each of the above polynucleotides, or the polynucleotides may be integrated into a vector as an operon containing plural cistrons such as a lactose operon so that the above polynucleotides are expressed. Any one or two or more of a polynucleotide encoding the present invented protein (A), the present invented protein (B), and a polynucleotide encoding the present protein (C) may be on a chromosome of a host cell.

A reaction when the step (1) and the step (2) of the present invented production method are performed in one reaction system can be performed in a reaction solution and under a reaction condition in accordance with the reaction in the step (2) of the present invented production method mentioned above.

In the step (1), as the oxidation reaction of an α-hydroxycarboxylic acid compound (e.g., sulfur-containing α-hydroxycarboxylic acid such as 2-hydroxy-4-(methylthio)butyric acid or α-hydroxy-isocaproic acid) proceeds, NAD+ in the reaction solution is converted into NADH. In the step (2), as the reductive amination reaction of α-oxocarboxylic acid (e.g., sulfur-containing α-oxocarboxylic acid such as 2-oxo-4-(methylthio)butyric acid or α-oxo-isocaproic acid) proceeds, NADH in the reaction solution is converted into NAD+. Therefore, when the step (1) and the step (2) of the present invented production method are performed in one reaction system, coenzymes (NAD+ and NADH) can be recycled at a catalytic amount.

The end point of the reaction can be determined by, for example, analyzing the amount of an α-hydroxycarboxylic acid compound (e.g., a sulfur-containing α-hydroxycarboxylic acid compound such as 2-hydroxy-4-(methylthio)butyric acid or α-hydroxy-isocaproic acid) in the reaction solution by liquid chromatography, etc.

The reaction time can be appropriately selected, and is usually within a range of about 0.5 hour to about 10 days.

Recovery of L-α-amino acid (e.g., sulfur-containing L-α-amino acid such as L-methionine or L-leucine) from the reaction solution may be performed in the same manner as in the step (2) of the present invented production method mentioned above.

EXAMPLES

The present invention will be described in more detail below by way of Examples, etc., but the present invention is not limited to these Examples.

Reference Example 1 (Preparation of Chromosomal DNA)

Into each of two 500 ml flasks, 100 ml of a medium (2 g of glucose, 0.5 g of polypeptone, 0.3 g of yeast extract, 0.3 g of meat extract, 0.2 g of ammonium sulfate, 0.1 g of potassium dihydrogenphosphate, 0.05 q of magnesium sulfate heptahydrate were dissolved in 100 ml of water, and the pH was adjusted to 6 with 2 N HCl) was put, and the medium was sterilized at 121° C. for 15 minutes. To each thereof, 0.3 ml of a culture solution of an *Achromobacter denitrificans* ATCC55564 strain which was cultured by shaking in a medium of the same composition at 30° C. for 48 hours was added, and the medium was cultured by shaking at 30° C. for 24 hours. The culture solution thus obtained was centrifuged at 8,000 rpm and 4° C. for 10 minutes and the precipitate thus produced was collected. The precipitate thus obtained was washed with 50 ml of 0.85% saline to obtain 3.5 g of wet cells.

From the cells thus obtained, chromosomal DNA (hereinafter referred to as the chromosomal DNA (A)) was obtained using the QIAprep Genomic-tip System (manufactured by Qiagen).

Example 1 (Preparation of Present Invented Polynucleotide (A) and Present Invented Polynucleotide (B), Recombinant Vector Containing Each Thereof, and Transformant Having the Vector (1) Primer Synthesis Oligonucleotide primers each having a base sequence represented by any one of SEQ ID NO: 9 to 12 are synthesized.

TABLE 1

| Sense primer | Antisense primer |
| --- | --- |
| SEQ ID NO: 9<br>CCATATGAAAAAGCTC<br>TCCATCGCCCAAG | SEQ ID NO: 10<br>ACTCGAGGCCTTCGTG<br>CGGCAGGGCTTC |
| SEQ ID NO: 11<br>CCATATGAGCCAAAAA<br>CCGAAAATCATCG | SEQ ID NO: 12<br>ACTCGAGGCCGCGGGC<br>TTCCCACACCTGCGGG |

(2) Recombinant Vector Containing Present Invented Polynucleotide (B)

Using an oligonucleotide primer having a base sequence represented by SEQ ID NO: 9 and an oligonucleotide primer having a base sequence represented by SEQ ID NO: 10, PCR was performed using the above chromosomal DNA (A) as a template and with the following reaction solution composition.

[Reaction Solution Composition]
Chromosomal DNA (A) solution: 1.5 µl
dNTP (a mixture of 2 mM each): 10 µl
Primer (50 pmol/µl): 0.3 µl each
2× buffer: 25 µl
KOD-FX (1 U/µl, Toyobo): 1 µl
Ultrapure water: 11.9 µl A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.1 kb was detected.

By adding restriction enzymes NdeI and XhoI to the remaining PCR reaction solution, DNA was double-digested, and enzymatically digested DNA of about 1.1 kb was purified.

Plasmid vector pET-22b (manufactured by Novagen) was double-digested with restriction enzymes NdeI and XhoI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 µg/ml of ampicillin, eight colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NdeI and XhoI, and then subjected to agarose gel electrophoresis. In each of six plasmids, DNA of about 1.1 kb was confirmed to be inserted into the above vector. When the base sequence of the inserted DNA of about 1.1 kb of one of these plasmids was analyzed, it was found that the DNA has a base sequence represented by SEQ ID NO: 2. This plasmid was designated as pET774. A base sequence represented by SEQ ID NO: 2 encodes an amino acid sequence represented by SEQ ID NO: 1. The plasmid pET774 is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an amino acid sequence represented by SEQ ID NO: 1.

(3) Recombinant Vector Containing Present Invented Polynucleotide (A)

Using an oligonucleotide primer having a base sequence represented by SEQ ID NO: 11 and an oligonucleotide primer having a base sequence represented by SEQ ID NO: 12, PCR was performed using the above chromosomal DNA (A) as a template and with the following reaction solution composition using the Expand High Fidelity PCR System (manufactured by Roche Diagnostics).

[Reaction Solution Composition]
Chromosomal DNA (A) solution: 1 µl
dNTP (a mixture of 2.5 mM each): 1 µl Primer (20 pmol/μl): 0.4 μl each
5× buffer (with $MgCl_2$): 10 μl
enz.expandHiFi ($3.5×10^3$ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 65° C. for 30 seconds, followed by 72° C. for one minute was performed 10 times, and then an incubation cycle consisting of incubation at 94° C. for 15 seconds, followed by 70° C. for 30 seconds, followed by 72° C. for one minute was performed 20 times, and further the solution was maintained at 72° C. for 7 minutes.

Subsequently, a part of the above PCR reaction solution was subjected to agarose gel electrophoresis. A DNA band of about 1.0 kb was detected.

By adding restriction enzymes NdeI and XhoI to the remaining PCR reaction solution, DNA was double-digested, and enzymatically digested DNA of about 1.0 kb was purified.

Plasmid vector pET-22b (manufactured by Novagen) was double-digested with restriction enzymes NdeI and XhoI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NdeI and XhoI, and then subjected to agarose gel electrophoresis. In each of six plasmids, DNA of about 1.0 kb was confirmed to be inserted into the above vector. When the base sequence of the inserted DNA of about 1.0 kb of one of these plasmids was analyzed, it was found that the DNA has a base sequence represented by SEQ ID NO: 4. This plasmid was designated as pET43. A base sequence represented by SEQ ID NO: 4 encodes an amino acid sequence represented by SEQ ID NO: 3. The plasmid pET43 is designed so that it can express a protein having an amino acid sequence in which an amino acid sequence composed of 8 amino acids including consecutive 6 residues of histidine (SEQ ID NO: 45: Leu-GluHisHisHisHisHisHis) is added to the carboxy terminus of an amino acid sequence represented by SEQ ID NO: 3.

Example 2 (Preparation of Present Invented Protein (A) and Present Invented Protein (B), and Preparation of L-α-Amino Acid Compound Using the Proteins)

(1) Present Invented Protein (B)

An *E. coli* BL21(DE3) strain was transformed using the plasmid pET774. The transformant thus obtained was inoculated into 800 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 4.9 g of the wet cells were suspended in 40 ml of 20 mM phosphate buffer (pH 7.4) containing 0.5 M NaCl and 5 mM imidazole (hereinafter sometimes referred to as the binding buffer), and disrupted at 2,500 rpm for 20 minutes using the Multi-beads shocker (manufactured by Yasui Kikai Corporation) and glass beads (0.1 mm). The disruption liquid thus obtained was centrifuged at 8,000 rpm and 4° C. for 10 minutes to obtain about 28 ml of centrifuged supernatant liquid.

About 10 ml of the centrifuged supernatant liquid thus obtained was applied to an affinity column (HisTrap HP, gel bed 5 ml, GE Healthcare Japan) with a flow rate of 5 ml/min. By passing about 25 ml of the binding buffer through this column with a flow rate of 5 ml/min, non-adsorbed proteins were eluted. Then, while maintaining the flow rate, by passing about 35 ml of 20 mM phosphate buffer (pH 7.4) containing 0.5 M NaCl and 29.75 mM imidazole through the column, non-adsorbed proteins and low adsorbed proteins were eluted.

Next, adsorbed proteins were eluted by gradient elution in which the imidazole concentration was increased from 29.75 mM to 500 mM while 47.5 ml was passed through, and 25 ml of a fraction with the imidazole concentration of about 120 mM to 270 mM was collected. The fraction thus obtained was subjected to the Amicon Ultra-15 (manufactured by Merck Millipore), and desalting and concentration was performed and the buffer was replaced by 0.5 M Tris-HCl (pH 9) to obtain about 2 ml of a purified enzyme solution (40 g protein/L). With 0.31 ml of a 2-fold diluent of the purified enzyme solution thus obtained, 50 mg of a calcium salt of 2-hydroxy-4-(methylthio)butyric acid (manufactured by Tokyo Chemical Industry), 10 mg of NAD+, 0.04 ml of 0.5 M Tris-HCl buffer (pH 9.0), 40 mg of ammonium sulfate, and 60 U of a leucine dehydrogenase (manufactured by Wako Pure Chemical Industries) were mixed, and the solution was shaken at 30° C. for 24 hours. This reaction solution was subjected to content analysis by liquid chromatography under the following condition. It was found that L-methionine was produced in a proportion of 35.3% based on the amount of a calcium salt of 2-hydroxy-4-(methylthio)butyric acid used for the reaction.

(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm (2) Present Invented Protein (A)

An *E. coli* BL21(DE3) strain was transformed using the plasmid pET43. The transformant thus obtained was inoculated into 800 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 5.2 g of the wet cells were suspended in 40 ml of 20 mM phosphate buffer (pH 7.4) containing 0.5 M NaCl and 5 mM imidazole (namely the binding buffer), and disrupted at 2,500 rpm for 20 minutes using the Multi-beads shocker (manufactured by Yasui Eikai Corporation) and glass beads (0.1 mmΦ). The disruption liquid thus obtained was centrifuged at 8,000 rpm and 4° C. for 10 minutes to obtain about 28 ml of centrifuged supernatant liquid.

About 10 ml of the centrifuged supernatant liquid thus obtained was applied to an affinity column (HisTrap HP, gel bed 5 ml, GE Healthcare Japan) with a flow rate of 5 ml/min. By passing about 25 ml of the binding buffer through this column with a flow rate of 5 ml/min, non-adsorbed proteins were eluted. Then, while maintaining the flow rate, by passing about 35 ml of 20 mM phosphate buffer (pH 7.4) containing 0.5 M NaCl and 29.75 mM imidazole through the column, non-adsorbed proteins and low adsorbed proteins were eluted.

Next, adsorbed proteins were eluted by gradient elution in which the imidazole concentration was increased from 29.75 mM to 500 mM while 47.5 ml was passed through, and 25 ml of a fraction with the imidazole concentration of about 120 mM to 270 mM was collected. The fraction thus obtained was subjected to the Amicon Ultra-15 (manufactured by Merck Millipore), and desalting and concentration was performed and the buffer was replaced by 0.5 M Tris-HCl (pH 9) to obtain about 2 ml of a purified enzyme solution (9 g protein/L). Then, 0.62 ml of the purified enzyme solution thus obtained was concentrated 2-fold with the Amicon Ultra-15 (manufactured by Merck Millipore). With 0.31 ml of the concentrated solution thus obtained, 50 mg of a calcium salt of 2-hydroxy-4-(methylthio)butyric acid (manufactured by Tokyo Chemical Industry), 10 mg of NAD+, 0.04 ml of 0.5 M Tris-HCl buffer (pH 9.0), 40 mg of ammonium sulfate, and 60 U of a leucine dehydrogenase (manufactured by Wako Pure Chemical Industries) were mixed, and the solution was shaken at 30° C. for 24 hours. This reaction solution was subjected to content analysis by liquid chromatography under the following condition. It was found that L-methionine was produced in a proportion of 36.9% based on the amount of a calcium salt of 2-hydroxy-4-(methylthio)butyric acid used for the reaction.

(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm (3) Present Invented Protein (A) and Present Invented Protein (B)

After 0.31 ml of a 2-fold diluent of the purified enzyme solution prepared in Example 2 (1) (40 g protein/L) was mixed with 0.31 ml of a 2-fold concentrated solution of the purified enzyme solution prepared in Example 2 (2) (9 g protein/L), the mixture was concentrated 2-fold with the Amicon Ultra-15 (manufactured by Merck Millipore). With 0.31 ml of the enzyme solution thus obtained, 50 mg of a calcium salt of 2-hydroxy-4-(methylthio)butyric acid (manufactured by Tokyo Chemical Industry), 10 mg of NAD+, 0.04 ml of 0.5 M Tris-HCl buffer (pH 9.0), 40 mg of ammonium sulfate, and 60 U of a leucine dehydrogenase (manufactured by Wako Pure Chemical Industries) were mixed, and the solution was shaken at 30° C. for 3 hours. This reaction solution was subjected to content analysis by liquid chromatography under the following condition. It was found that L-methionine was produced in a proportion of 47.0% based on the amount of a calcium salt of 2-hydroxy-4-(methylthio)butyric acid used for the reaction.

(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm Example 3 (Preparation of Recombinant Vector Containing Present Polynucleotide (C) and Transformant Having the Vector, and Preparation of Present Protein (C))

(1) Preparation of Recombinant Vector Containing Present Polynucleotide (C)

A *Bacillus sphaericus* IFO3525 strain was cultured in 100 ml of a sterilized LB medium to obtain 0.4 g of cells. From the cells, chromosomal DNA (hereinafter referred to as the chromosomal DNA (B)) was purified using the Qiagen Genomic Tip (manufactured by Qiagen) in accordance with the method mentioned in the manual attached thereto.

Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide primer having a base sequence represented by SEQ ID NO: 14 (GCCATGGAAATCTTCAAGTATATGG) and an oligonucleotide primer having a base sequence represented by SEQ ID NO: 15 (GGGCCCGGGTTAACGGCCGTTCAAAAAATATT) are synthesized.

Using an oligonucleotide primer having a base sequence represented by SEQ ID NO: 14 and an oligonucleotide primer having a base sequence represented by SEQ ID NO: 15, PCR was performed using the above chromosomal DNA (B) as a template and with the following reaction solution composition using the Expand High Fidelity PCR System (Roche Diagnostics).

[Reaction Solution Composition]
Chromosomal DNA (B) solution: 1 μl
dNTP (a mixture of 2.5 mM each): 1 μl
Primer (20 pmol/μl): 0.4 μl
Primer (4 pmol/μl): 2 μl
5× buffer (with $MgCl_2$): 10 μl
enz.expandHiFi ($3.5×10^3$ U/ml): 0.5 μl
Ultrapure water: 35.1 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 20 seconds, followed by 55° C. for 30 seconds, followed by 72° C. for 1.5 minutes was performed 25 times, and further the solution was maintained at 72° C. for 7 minutes.

Subsequently, a part of the above PCR reaction solution was subjected to agarose gel electrophoresis. A DNA band of about 1.1 kb was detected.

By adding restriction enzymes NcoI and SmaI to the remaining PCR reaction solution, DNA was double-digested, and enzymatically digested DNA of about 1.1 kb was purified.

Plasmid vector pTrc99A (manufactured by GE Healthcare Japan) was double-digested with restriction enzymes NcoI and SmaI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C.

for 17 hours. Plasmids were removed from each cultured cell using the QIAprep Spin Miniprep Kit (manufactured by Qiagen). A part of each of the removed plasmids was double-digested with restriction enzymes NcoI and XbaI, and then subjected to agarose gel electrophoresis. In each of six plasmids, DNA of about 1.1 kb was confirmed to be inserted into the above vector. One of these plasmids was designated as pTrcLD.

(2) Recombinant Vector Containing Present Polynucleotide (C)

Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide having a base sequence represented by SEQ ID NO: 16 (GTCGCTATATT ACCGGTGAAGATGTTG) (sense primer) and an oligonucleotide having a base sequence represented by SEQ ID NO: 17 (CAACATCTTCACCGGTAATATAGCGAC) (antisense primer) are synthesized as a primer for mutation introduction for substituting the 113th alanine in the enzyme by glycine. Using an oligonucleotide having a base sequence represented by SEQ ID NO: 16 and an oligonucleotide having a base sequence represented by SEQ ID NO: 17 as a primer, PCR was performed using the recombinant vector pTrcLD mentioned in Example 3 (1) as a template and with the following reaction solution composition using the QuikChange II Site-Directed Mutagenesis Kit (manufactured by STRATAGENE).

[Reaction Solution Composition]
DNA solution of pTrcLD: 0.4 μl
dNTP mix (contained in the above Kit): 1 μl
Sense primer (50 μM): 0.4 μl
Antisense primer (50 μM): 0.4 μl
10× buffer (contained in the above Kit): 5 μl
PfuUltra (contained in the above Kit): 1 μl
Ultrapure water: 41.8 μl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 55° C. for one minute, followed by 68° C. for 5 minutes was performed 12 times, and then the solution was stored at 4° C.

To the PCR reaction solution thus obtained, 1 μl of a DpnI restriction enzyme (contained in the above Kit) was added, and then the solution was incubated at 37° C. for 1 hour. Using the incubated solution thus obtained, *E. coli* DH5α was transformed.

From each of the transformants thus obtained, plasmids were extracted, and then a base sequence at the mutation site was determined by the dideoxy method to confirm that the designed mutation was introduced. A plasmid having a base sequence represented by SEQ ID NO: 8 was designated as pTrcLD(A113G). A base sequence represented by SEQ ID NO: 8 encodes an amino acid sequence represented by SEQ ID NO: 7.

(3) Recombinant Vector Containing Present Polynucleotide (C)

(3-1) Introduction of Site-Specific Mutation for Base Substitution

Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide having a base sequence represented by SEQ ID NO: 18 (GATAGTATTC-CAACCTATGTTGCGGC) (sense primer) and an oligonucleotide having a base sequence represented by SEQ ID NO: 19 (GCCGCAACATAGGTTGAATACTATC) (antisense primer) are synthesized as a primer for mutation introduction for substituting the 993rd adenine by cytosine.

Using an oligonucleotide having a base sequence represented by SEQ ID NO: 18 and an oligonucleotide having a base sequence represented by SEQ ID NO: 19 as a primer, PCR was performed using the recombinant vector pTrcLD (A113G) mentioned in Example 3 (2) as a template and with the following reaction solution composition using the QuikChange II Site-Directed Mutagenesis Kit (manufactured by STRATAGENE).

[Reaction Solution Composition]
DNA solution of pTrcLD(A113G): 1 μl
dNTP mix (contained in the above Kit): 1 μl
Sense primer (50 μM): 0.4 μl
Antisense primer (50 μM): 0.4 μl
10× buffer (contained in the above Kit): 5 μl
PfuUltra (contained in the above Kit): 1 μl
Ultrapure water: 41.2 μl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 μl of a DpnI restriction enzyme (contained in the above Kit) was added, and then the solution was incubated at 37° C. for 1 hour. Using the incubated solution thus obtained, *E. coli* DH5α was transformed.

From the transformants thus obtained, plasmids were extracted, and then a base sequence at the mutation site was determined by the dideoxy method. A plasmid into which the designed mutation was confirmed to be introduced was designated as pTrcLD(A113G)nd.

(3-2) Recombinant Vector Containing Present Polynucleotide (C)

Based on a base sequence encoding a leucine dehydrogenase derived from a *Bacillus sphaericus* IFO3525 strain mentioned in Journal of Molecular Catalysis B: Enzymatic, 23 (2003) 239-247, an oligonucleotide primer having a base sequence represented by SEQ ID NO: 20 (GGGCATATG-GAAATCTTCAAGTATATGG; (sense primer) and an oligonucleotide primer having a base sequence represented by SEQ ID NO: 21 (GGATCCTTAACGGCCGTTCAAAAT-ATT) (antisense primer) are synthesized. Using an oligonucleotide primer having a base sequence represented by SEQ ID NO: 20 and an oligonucleotide primer having a base sequence represented by SEQ ID NO: 21 as a primer, PCR was performed using the recombinant vector pTrcLD (A113G)nd mentioned in Example 3 (3-1) as a template and with the following reaction solution composition using the Expand High Fidelity PCR System (Roche Diagnostics).

[Reaction Solution Composition]
DNA solution of pTrcLD(A113G)nd: 1 μl
dNTP (a mixture of 2.5 mM each): 1 μl
Primer (20 pmol/μl): 0.4 μl each
5× buffer (with MgCl$_2$): 10 μl
enz.expandHiFi (3.5×10$^3$ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 55° C. for 30 seconds, followed by 72° C. for 1.5 minutes was performed 10 times, and then an incubation cycle consisting of incubation at 94° C. for 15 seconds, followed by 60° C. for 30 seconds, followed by 72° C. for 1.5 minutes was performed 20 times, and further the solution was maintained at 72° C. for 7 minutes.

Subsequently, a part of the above PCR reaction solution was subjected to agarose gel electrophoresis. A DNA band of about 1.1 kb was detected.

By adding restriction enzymes NdeI and BamHI to the remaining PCR reaction solution, DNA was double-digested, and enzymatically digested DNA of about 1.1 kb was purified.

Plasmid vector pET-15b (manufactured by Novagen) was double-digested with restriction enzymes NdeI and BamHI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 µg/ml of ampicillin, 10 colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NdeI and BamHI, and then subjected to agarose gel electrophoresis. In each of four plasmids, DNA of about 1.1 kb was confirmed to be inserted into the above vector. The plasmids thus obtained are designed so that they can express a protein in which an amino acid sequence composed of 20 amino acids including consecutive 6 residues of histidine (SEQ ID NO: 44: Met-GlySerSerHSeisHisHisHisHisHisSerSerGlyLeuValProArg-GlySerHis) is added to the amino terminus of a leucine dehydrogenase encoded by the recombinant vector pTrcLD (A113G)nd. One of the plasmids thus obtained was designated as pETLD(A113G).

(4) Present Protein (C)

An *E. coli* BL21(DE3) strain was transformed using the recombinant vector pETLD(A113G). The transformant thus obtained was inoculated into 800 ml of a sterilized LB medium containing 0.1 mM IPTG and 50 µg/ml of ampicillin, and the medium was cultured by shaking at 30° C. for 15 hours. The culture solution thus obtained was centrifuged to obtain about 6 g of wet cells. About 6 g of the wet cells were suspended in 40 ml of 20 mM phosphate buffer (pH 7.4) containing 0.5 M NaCl and 5 mM imidazole (namely the binding buffer), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 25 ml of centrifuged supernatant liquid. About 10 ml of the centrifuged supernatant liquid thus obtained was applied to an affinity column (HisTrap HP, gel bed 5 ml, manufactured by GE Healthcare Japan) with a flow rate of 5 ml/min. By passing about 25 ml of the binding buffer through this column with a flow rate of 5 ml/min, non-adsorbed proteins were eluted. Then, while maintaining the flow rate, by passing about 35 ml of 20 mM phosphate buffer (pH 7.4) containing 0.5 M NaCl and 29.75 mM imidazole through the column, non-adsorbed proteins and low adsorbed proteins were eluted. Next, adsorbed proteins were eluted by gradient elution in which the imidazole concentration was increased from 29.75 mM to 500 mM while 47.5 ml was passed through, and 30 ml of a fraction with the imidazole concentration of about 160 mM to 443 mM was collected. The fraction thus obtained was subjected to the Amicon Ultra-15 (manufactured by Merck Millipore), and desalting and concentration was performed and the buffer was replaced by 0.5 M Tris-HCl (pH 9) to obtain about 2 ml of a fraction (32.6 g protein/L). This fraction is hereinafter referred to as the leucine dehydrogenase (A113G) purified enzyme solution.

Example 4 (Preparation of L-α-Amino Acid Compound Using Present Invented Protein (A), Present Invented Protein (B), and Present Protein (C))

After 0.31 ml of a 2-fold diluent of the purified enzyme solution prepared in Example 2 (1) (40 g protein/L) was mixed with 0.31 ml of a 2-fold concentrated solution of the purified enzyme solution prepared in Example 2 (2) (9 g protein/L), the mixture was concentrated 2-fold with the Amicon Ultra-15 (manufactured by Merck Millipore). With 0.31 ml of the enzyme solution thus obtained, 50 mg of a calcium salt of 2-hydroxy-4-(methylthio)butyric acid (manufactured by Tokyo Chemical Industry), 10 mg of NAD+, 0.04 ml of 0.5 M Tris-HCl buffer (pH 9.0), 40 mg of ammonium sulfate, and 0.15 ml of the leucine dehydrogenase (A113G) purified enzyme solution prepared in Example 3 (4) (32.6 g protein/L) were mixed, and the solution was shaken at 30° C. for 1 hour. This reaction solution was subjected to content analysis by liquid chromatography under the following condition. It was found that L-methionine was produced in a proportion of 49.9% based on the amount of a calcium salt of 2-hydroxy-4-(methylthio) butyric acid used for the reaction.

(Content Analysis Condition)
Column: UNISON UK-C18 (4.6 mmφ×25 cm, 3 µm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm Example 5 (Preparation of Present Invented Polynucleotide (A), Present Invented Recombinant Vector (ABC), and Transformant Having the Vector)

(1) Recombinant Vector Containing Present Invented Polynucleotide (A)

Double-stranded DNA having a base sequence represented by SEQ ID NO: 13 in which the base sequence ccatggct is added to its 5' end and the base sequence ggatcc is added to its 3' end is prepared. A base sequence represented by SEQ ID NO: 13 encodes an amino acid sequence represented by SEQ ID NO: 3.

The double-stranded DNA of about 1.0 kb thus prepared was double-digested with restriction enzymes NcoI and BamHI, and enzymatically digested DNA was purified.

Plasmid vector pTrc99A (manufactured by GE Healthcare Japan) was double-digested with restriction enzymes NcoI and BamHI, and enzymatically digested vector DNA was purified.

These purified DNAs were mixed and ligated with a T4 DNA ligase, and using the ligation solution thus obtained, an *E. coli* JM109 strain was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and BamHI, and then subjected to agarose gel electrophoresis. In each of six plasmids, DNA of about 1.0 kb was confirmed to be inserted into the above vector. Base sequences of the plasmids thus obtained were determined, and a plasmid having the target base sequence was designated as pTrc43SC.

(2) Present Invented Recombinant Vector (ABC)

(2-1) Recombinant Vector Containing Present Polynucleotide (C)

Based on a base sequence of a leucine dehydrogenase derived from a *Bacillus sphaericus* IFO3525 strain mentioned in Journal of Molecular Catalysis B: Enzymatic 23 (2003) 239-247, an oligonucleotide having a base sequence represented by SEQ ID NO: 22 (CGTAGCTTAC AAACTTTGCGAGTATTTAC) (sense primer) and an oligonucleotide having a base sequence represented by SEQ ID NO: 23 (GTAAATACTCGCAAAGTTTGTAAGCTACG) (antisense primer) are synthesized as a primer for mutation introduction for substituting the 561st guanine by adenine. Using an oligonucleotide having a base sequence represented by SEQ ID NO: 22 and an oligonucleotide having a base sequence represented by SEQ ID NO: 23 as a primer, PCR was performed using the plasmid pTrcLD(A113G)nd mentioned in Example 3 (3) as a template and with the following reaction solution composition using the QuikChange II Site-Directed Mutagenesis Kit (manufactured by STRATAGENE).

[Reaction Solution Composition]
DNA solution of pTrcLD(A113G)nd: 1 μl
dNTP mix (contained in the above Kit): 1 μl
Sense primer (50 μM): 0.4 μl
Antisense primer (50 μM): 0.4 μl
10× buffer (contained in the above Kit): 5 μl
PfuUltra (contained in the above Kit): 1 μl
Ultrapure water: 41.2 μl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 μl of a DpnI restriction enzyme (contained in the above Kit) was added, and then the solution was incubated at 37° C. for 1 hour. Using the incubated solution thus obtained, *E. coli* DH5α was transformed.

From the transformants thus obtained, plasmids were extracted, and then a base sequence at the mutation site was determined by the dideoxy method. A plasmid into which the designed mutation was confirmed to be introduced was designated as pTrcLD(A113G)ndhd.

(2-2) Recombinant Vector Containing Present Invented Polynucleotide (B)

Using an oligonucleotide having a base sequence represented by SEQ ID NO: 24 (CCATGGCTAT-GAAAAAGCTCTCCATCGCCC) (sense primer) and an oligonucleotide having a base sequence represented by SEQ ID NO: 25 (CAAGCTTGCTAGCCTTCGTGCGGCA-GGGCTTC) (antisense primer) as a primer, PCR was performed using the plasmid pET774 mentioned in Example 1 (2) as a template and with the following reaction solution composition.

[Reaction Solution Composition]
DNA solution of pET774: 1.5 μl
dNTP (a mixture of 2 mM each): 10 μl
Primer (50 pmol/μl): 0.3 μl each
2× buffer: 25 μl
KOD-FX (1 U/μl, Toyobo): 1 μl
Ultrapure water: 11.9 μl A container containing a reaction solution with the above composition was set in a thermal cycler (PERKIN ELMER-GeneAmp PCR System 9700) and incubated at 944° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.1 kb was detected.

By adding restriction enzymes NcoI and HindIII to the remaining PCR reaction solution, DNA was double-digested, and enzymatically digested DNA of about 1.1 kb was purified.

Plasmid vector pTrc99A (manufactured by GE Healthcare Japan) was double-digested with restriction enzymes NcoI and HindIII, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and HindIII, and then subjected to agarose gel electrophoresis. In each of six plasmids, DNA of about 1.1 kb was confirmed to be inserted into the above vector. One of these plasmids was designated as pTrc774NH.

(2-3) Recombinant Vector Containing Present Invented Polynucleotide (B) and Present Polynucleotide (C)

Using an oligonucleotide having a base sequence represented by SEQ ID NO: 26 (CGGATCCGAGGAAACA-GACCATGG) (sense primer) and an oligonucleotide having a base sequence represented by SEQ ID NO: 27 (GCTGCA-GCCTAGCCTTCGTGCGGCAGGGCTTC) (antisense primer), PCR was performed using the plasmid pTrc774NH mentioned in Example 5 (2-2) as a template and with the following reaction solution composition.

[Reaction Solution Composition]
DNA solution of pTrc774NH: 1.5 μl
dNTP (a mixture of 2 mM each): 10 μl
Primer (50 pmol/μl): 0.3 μl each
2× buffer: 25 μl
KOD-FX (1 U/μl, Toyobo): 1 μl
Ultrapure water: 11.9 μl A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.1 kb was detected.

By adding restriction enzymes BamHI and PstI to the remaining PCR reaction solution, DNA was double-digested, and enzymatically digested DNA of about 1.1 kb was purified.

The plasmid pTrcLD(A113G)ndhd mentioned in Example 5 (2-1) was double-digested with restriction enzymes BamHI and PstI, and enzymatically digested plasmid DNA was purified.

These purified DNAs were mixed and ligated with a T4 DNA ligase, and using the ligation solution thus obtained, $E.$ $coli$ DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes BamHI and PstI, and then subjected to agarose gel electrophoresis. In each of six plasmids, DNA of about 1.1 kb was confirmed to be inserted into the plasmid pTrcLD(A113G)ndhd. One of these plasmids was designated as pTrcLD(A113G)/774.

(2-4) Recombinant Vector Containing Present Invented Polynucleotide (A), Present Invented Polynucleotide (B), and Present Polynucleotide (C)

Using an oligonucleotide having a base sequence represented by SEQ ID NO: 28 (GCTGCAGCAGGAAACA-GACCATGG) (sense primer) and an oligonucleotide having a base sequence represented by SEQ ID NO: 29 (CAAGCT-TGTTAGCCACGGGCTTCCCACACC) (antisense primer) as a primer, PCR was performed using the plasmid pTrc43SC mentioned in Example 5 (1) as a template and with the following reaction solution composition using the Expand High Fidelity PCR System (Roche Diagnostics).
[Reaction Solution Composition]
DNA solution of pTrc43SC: 1 μl
dNTP (a mixture of 2.5 mM each): 1 μl
Primer (20 pmol/μl): 0.4 μl each
5× buffer (with MgCl$_2$): 10 μl
enz.expandHiFi (3.5×10$^3$ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 65° C. for 30 seconds, followed by 72° C. for one minute was performed 10 times, and then an incubation cycle consisting of incubation at 94° C. for 15 seconds, followed by 70° C. for 30 seconds, followed by 72° C. for one minute was performed 20 times, and further the solution was maintained at 72° C. for 7 minutes.

Subsequently, a part of the above PCR reaction solution was subjected to agarose gel electrophoresis. A DNA band of about 1.0 kb was detected.

By adding restriction enzymes PstI and HindIII to the remaining PCR reaction solution, DNA was double-digested, and enzymatically digested DNA of about 1.0 kb was purified.

The plasmid pTrcLD(A113G)/774 mentioned in Example 5 (2-3) was double-digested with restriction enzymes PstI and HindIII, and enzymatically digested plasmid DNA was purified.

These purified DNAs were mixed and ligated with a T4 DNA ligase, and using the ligation solution thus obtained, $E.$ $coli$ DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes PstI and HindIII, and then subjected to agarose gel electrophoresis. In each of six plasmids, DNA of about 1.0 kb was confirmed to be inserted into the plasmid pTrcLD(A113G/774. One of these plasmids was designated as pTrcLD(A113G)/774/43SC.

Example 6 (Preparation of L-α-Amino Acid Compound Using Treated Product of Transformant Having Present Invented Recombinant Vector (ABC))

An $E.$ $coli$ JM109 strain was transformed using the plasmid pTrcLD(A113G)/774/43SC. The transformant thus obtained was inoculated into 100 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 0.8 g of the wet cells were suspended in 5 ml of 0.5 M Tris-HCl buffer (pH 9), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 3.5 ml of centrifuged supernatant liquid (28 g protein/L).

Then, 0.34 ml of the centrifuged supernatant liquid thus obtained was concentrated 3.4-fold with the Amicon Ultra-15 (manufactured by Merck Millipore). With 0.1 ml of the concentrated centrifuged supernatant liquid thus obtained, 0.35 ml of a 40% aqueous solution of 2-hydroxy-4-(methylthio)butyric acid (manufactured by Tokyo Chemical Industry) whose pH was adjusted to 9 with ammonia water, 10 mg of NAD+, 0.05 ml of 0.5 M Tris-HCl buffer (pH 9.0), and 20 mg of ammonium sulfate were mixed, and the solution was shaken at 30° C. for 1 hour. This reaction solution was subjected to content analysis by liquid chromatography under the following condition. It was found that 93.5 g/L of L-methionine was produced. The yield of L-methionine based on the amount of 2-hydroxy-4-(methylthio)butyric acid used for the reaction was 30.4%.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10

Flow rate: 0.8 ml/min
Column temperature: 37° C.
Detection: 210 nm

Example 7 (Preparation of Recombinant Vector Containing Polynucleotide Encoding Present Invented Protein (A) and Transformant Having the Vector (1) Recombinant Vector Containing Polynucleotide Encoding Present Invented Protein (A) Having Amino Acid Sequence Represented by SEQ ID NO: 3
(1-1)
An oligonucleotide having a base sequence represented by SEQ ID NO: 30 (CCATATGTCTCAAAAAC-CAAAAATCATCG) (sense primer) and an oligonucleotide having a base sequence represented by SEQ ID NO: 31 (ACTCGAGGCCACGGGCTTCCCACACCTGCG) (antisense primer) are synthesized. Using an oligonucleotide primer having a base sequence represented by SEQ ID NO: 30 and an oligonucleotide primer having a base sequence represented by SEQ ID NO: 31, PCR was performed using the plasmid pTrc43SC mentioned in Example 5 (1) as a template and with the following reaction solution composition using the Expand High Fidelity PCR System (Roche Diagnostics).
[Reaction Solution Composition]
DNA solution of pTrc43SC: 1 μl
dNTP (a mixture of 2.5 mM each): 1 μl
Primer (20 pmol/μl): 0.4 μl each
5× buffer (with MgCl$_2$): 10 μl
enz.expandHiFi (3.5×10$^3$ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 55° C. for 30 seconds, followed by 72° C. for 1.5 minutes was performed 10 times, and then an incubation cycle consisting of incubation at 94° C. for 15 seconds, followed by 60° C. for 30 seconds, followed by 72° C. for 1.5 minutes was performed 20 times, and further the solution was maintained at 72° C. for 7 minutes.

Subsequently, a part of the above PCR reaction solution was subjected to agarose gel electrophoresis. A DNA band of about 1.0 kb was detected.

By adding restriction enzymes NdeI and XhoI to the remaining PCR reaction solution, DNA was double-digested, and enzymatically digested DNA of about 1.0 kb was purified.

Plasmid vector pET-22b (manufactured by Novagen) was double-digested with restriction enzymes NdeI and XhoI, and enzymatically digested DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, 10 colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NdeI and XhoI, and then subjected to agarose gel electrophoresis. In each of four plasmids, DNA of about 1.0 kb was confirmed to be inserted into the above vector. One of these plasmids was designated as pET43SCcHis. The plasmid pET43SCcHis is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an amino acid sequence represented by SEQ ID NO: 3.
(1-2)
An oligonucleotide having a base sequence represented by SEQ ID NO: 32 (GCCATGGCTATGTCTCAAAAAC-CAAAAATC) (sense primer) and an oligonucleotide having a base sequence represented by SEQ ID NO: 33 (GGATC-CTCAGTGGTGGTGGTGGTGGTG) (antisense primer) are synthesized. Using an oligonucleotide primer having a base sequence represented by SEQ ID NO: 32 and an oligonucleotide primer having a base sequence represented by SEQ ID NO: 33, PCR was performed using the plasmid pET43SCcHis mentioned in Example 7 (1-1) as a template and with the following reaction solution composition using the Expand High Fidelity PCR System (Roche Diagnostics).
[Reaction Solution Composition]
DNA solution of pET43SCcHis: 1 μl
dNTP (a mixture of 2.5 mM each): 1 μl
Primer (20 pmol/μl): 0.4 μl each
5× buffer (with MgCl$_2$): 10 μl
enz.expandHiFi (3.5×10$^3$ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 55° C. for 30 seconds, followed by 72° C. for 1.5 minutes was performed 10 times, and then an incubation cycle consisting of incubation at 94° C. for 15 seconds, followed by 60° C. for 30 seconds, followed by 72° C. for 1.5 minutes was performed 20 times, and further the solution was maintained at 72° C. for 7 minutes.

Subsequently, a part of the above PCR reaction solution was subjected to agarose gel electrophoresis. A DNA band of about 1.0 kb was detected.

By adding restriction enzymes NcoI and BamHI to the remaining PCR reaction solution, DNA was double-digested, and enzymatically digested DNA was purified.

Plasmid vector pTrc99A (manufactured by GE Healthcare Japan) was double-digested with restriction enzymes NcoI and BamHI, and enzymatically digested DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, 10 colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and BamHI, and then subjected to agarose gel electrophoresis. In each of four plasmids, the DNA of about 1.0 kb was confirmed to be inserted. One of these plasmids was designated as pTrc43SCcHis. The plasmid pTrc43SCcHis is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an amino acid sequence represented by SEQ ID NO: 3.

(2) Recombinant Vector Containing Polynucleotide Encoding Present Invented Protein (A) Having Altered Amino Acid Sequence V109I Based on a base sequence represented by SEQ ID NO: 13, an oligonucleotide having a base sequence represented by SEQ ID NO: 34 (CGCTGTTGCTGATATTAC CATCGGCCTG) (sense primer) and an oligonucleotide having a base sequence represented by SEQ ID NO: 35 (CAGGCCGATGGTAATATCAGCAACAGCG) (antisense primer) are synthesized as a primer for mutation introduction for substituting the 325th guanine by adenine. Substitution of the 325th guanine by adenine in a base sequence represented by SEQ ID NO: 13 brings about substitution of the 109th valine by isoleucine in an amino acid sequence represented by SEQ ID NO: 3.

Using an oligonucleotide having a base sequence represented by SEQ ID NO: 34 and an oligonucleotide having a base sequence represented by SEQ ID NO: 35 as a primer, PCR was performed using the plasmid pTrc43SCcHis mentioned in Example 7 (1-2) as a template and with the following reaction solution composition using the QuikChange II Site-Directed Mutagenesis Kit (manufactured by STRATAGENE).
[Reaction Solution Composition]
DNA solution of pTrc43SCcHis: 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit): 1 µl
Ultrapure water: 41.2 µl A container containing a reaction solution with the above composition was set in a thermal cycler (PERKIN ELMERGeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, E. coli DH5α was transformed.

From the transformants thus obtained, plasmids were extracted, and then a base sequence at the mutation site was determined by the dideoxy method. A plasmid into which the designed mutation was confirmed to be introduced was designated as pTrc43SCcHis-g325a. The plasmid pTrc43SCcHis-g325a is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an altered amino acid sequence having substitution of the 109th valine by isoleucine in an amino acid sequence represented by SEQ ID NO: 3.

(3) Recombinant Vector Containing Polynucleotide Encoding Present Invented Protein (A) Having Altered Amino Acid Sequence G191D Based on a base sequence represented by SEQ ID NO: 13, an oligonucleotide having a base sequence represented by SEQ ID NO: 36 (GGCGGCATACGTCGATCGT GACGAGCTG) (sense primer) and an oligonucleotide having a base sequence represented by SEQ ID NO: 37 (CAGCTCGTCACGATCGACGTATGCCGCC) (antisense primer) are synthesized as a primer for mutation introduction for substituting the 572nd guanine by adenine. Substitution of the 572nd guanine by adenine in a base sequence represented by SEQ ID NO: 13 brings about substitution of the 191st glycine by aspartic acid in an amino acid sequence represented by SEQ ID NO: 3.

Using an oligonucleotide having a base sequence represented by SEQ ID NO: 36 and an oligonucleotide having a base sequence represented by SEQ ID NO: 37 as a primer, PCR was performed using the plasmid pTrc43SCcHis mentioned in Example 7 (1-2) as a template and with the following reaction solution composition using the QuikChange II Site-Directed Mutagenesis Kit (manufactured by STRATAGENE).
[Reaction Solution Composition]
DNA solution of pTrc43SCcHis: 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit): 1 µl
Ultrapure water: 41.2 µl A container containing a reaction solution with the above composition was set in a thermal cycler (PERKIN ELMERGeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, E. coli DH5α was transformed.

From the transformants thus obtained, plasmids were extracted, and then a base sequence at the mutation site was determined by the dideoxy method. A plasmid into which the designed mutation was confirmed to be introduced was designated as pTrc43SCcHis-g572a. The plasmid pTrc43SCcHis-g572a is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an altered amino acid sequence having substitution of the 191st glycine by aspartic acid in an amino acid sequence represented by SEQ ID NO: 3.

(4) Recombinant Vector Containing Polynucleotide Encoding Present Invented Protein (A) Having Altered Amino Acid Sequence Q246R Based on a base sequence represented by SEQ ID NO: 13, an oligonucleotide having a base sequence represented by SEQ ID NO: 38 (GCAGCACTGGTACGGGCACT GCGCTCTG) (sense primer) and an oligonucleotide having a base sequence represented by SEQ ID NO: 39 (CAGAGCGCAGTGCCCGTACCAGTGCTGC) (antisense primer) are synthesized as a primer for mutation introduction for substituting the 737th adenine by guanine. Substitution of the 737th adenine by guanine in a base sequence represented by SEQ ID NO: 13 brings about substitution of the 246th glutamine by arginine in an amino acid sequence represented by SEQ ID NO: 3.

Using an oligonucleotide having a base sequence represented by SEQ ID NO: 38 and an oligonucleotide having a base sequence represented by SEQ ID NO: 39 as a primer, PCR was performed using the plasmid pTrc43SCcHis mentioned in Example 7 (1-2) as a template and with the following reaction solution composition using the QuikChange II Site-Directed Mutagenesis Kit (manufactured by STRATAGENE).

[Reaction Solution Composition]
DNA solution of pTrc43SCcHis: 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit): 1 µl
Ultrapure water: 41.2 µl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, E. coli DH5α was transformed.

From the transformants thus obtained, plasmids were extracted, and then a base sequence at the mutation site was determined by the dideoxy method. A plasmid into which the designed mutation was confirmed to be introduced was designated as pTrc43SCcHis-a737g. The plasmid pTrc43SCcHis-a737g is designed so that it can express a protein having an amino acid sequence in which an amino acid sequence composed of 8 amino acids including consecutive 6 residues of histidine (SEQ ID NO: 45: Leu-GluHisHisHisHisHisHis) is added to the carboxy terminus of an altered amino acid sequence having substitution of the 246th glutamine by arginine in an amino acid sequence represented by SEQ ID NO: 3.

(5) Recombinant Vector Containing Polynucleotide Encoding Present Invented Protein (A) Having Altered Amino Acid Sequence V109I/G191D Using an oligonucleotide having a base sequence represented by SEQ ID NO: 36 and an oligonucleotide having a base sequence represented by SEQ ID NO: 37, which are primers for mutation introduction for converting the 572nd guanine in a base sequence represented by SEQ ID NO: 13 to adenine, as a primer, PCR was performed using the plasmid pTrc43SCcHis-g325a mentioned in Example 7 (2) as a template and with the following reaction solution composition using the QuikChange II Site-Directed Mutagenesis Kit (manufactured by STRATAGENE).

[Reaction Solution Composition]
DNA solution of pTrc43SCcHis-g325a: 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit); 1 µl
Ultrapure water: 41.2 µl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, E. coli DH5α was transformed.

From the transformants thus obtained, plasmids were extracted, and then a base sequence at the mutation site was determined by the dideoxy method. A plasmid into which the designed mutation was confirmed to be introduced was designated as pTrc43SCcHis-g325a/g572a. The plasmid pTrc43SCcHis-g325a/g572a is designed so that it can express a protein having an amino acid sequence in which an amino acid sequence composed of 8 amino acids including consecutive 6 residues of histidine (SEQ ID NO: 45: Leu-GluHisHisHisHisHisHis) is added to the carboxy terminus of an altered amino acid sequence having substitution of the 109th valine by isoleucine and substitution of the 191st glycine by aspartic acid in an amino acid sequence represented by SEQ ID NO: 3.

(6) Recombinant Vector Containing Polynucleotide Encoding Present Invented Protein (A) Having Altered Amino Acid Sequence V109I/Q246R Using an oligonucleotide having a base sequence represented by SEQ ID NO: 38 and an oligonucleotide having a base sequence represented by SEQ ID NO: 39, which are primers for mutation introduction for converting the 737th adenine in a base sequence represented by SEQ ID NO: 13 to guanine, as a primer, PCR was performed using the plasmid pTrc43SCcHis-g325a mentioned in Example 7 (2) as a template and with the following reaction solution composition using the QuikChange II Site-Directed Mutagenesis Kit (manufactured by STRATAGENE).

[Reaction Solution Composition]
DNA solution of pTrc43SCcHis-g325a: 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit): 1 µl
Ultrapure water: 41.2 µl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, E. coli DH5α, was transformed.

From the transformants thus obtained, plasmids were extracted, and then a base sequence at the mutation site was determined by the dideoxy method. A plasmid into which the designed mutation was confirmed to be introduced was designated as pTrc43SCcHis-g325a/a737g. The plasmid pTrc43SCcHis-g325a/a737g is designed so that it can express a protein having an amino acid sequence in which an amino acid sequence composed of 8 amino acids including consecutive 6 residues of histidine (SEQ ID NO: 45: Leu-GluHisHisHisHisHisHis) is added to the carboxy terminus of an altered amino acid sequence having substitution of the 109th valine by isoleucine and substitution of the 246th glutamine by arginine in an amino acid sequence represented by SEQ ID NO: 3.

(7) Recombinant Vector Containing Polynucleotide Encoding Present Invented Protein (A) Having Altered Amino Acid Sequence G191D/Q246R Using an oligonucleotide having a base sequence represented by SEQ ID NO: 38 and an oligonucleotide having a base sequence represented by SEQ ID NO: 39, which are primers for mutation introduction for converting the 737th adenine in a base sequence represented by SEQ ID NO: 13 to guanine, as a primer, PCR was performed using the plasmid pTrc43SCcHis-g572a mentioned in Example 7 (3) as a template and with the following reaction solution composition using the QuikChange II Site-Directed Mutagenesis Kit (manufactured by STRATAGENE).

[Reaction Solution Composition]
DNA solution of pTrc43SCcHis-g572a: 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit): 1 µl
Ultrapure water: 41.2 µl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, *E. coli* DI-15a was transformed.

From the transformants thus obtained, plasmids were extracted, and then a base sequence at the mutation site was determined by the dideoxy method. A plasmid into which the designed mutation was confirmed to be introduced was designated as pTrc43SCcHis-g572a/a737g. The plasmid pTrc43SCcHis-g572a/a737g is designed so that it can express a protein having an amino acid sequence in which an amino acid sequence composed of 8 amino acids including consecutive 6 residues of histidine (SEQ ID NO: 45: Leu-GluHisHisHisHisHisHis) is added to the carboxy terminus of an altered amino acid sequence having substitution of the 191st glycine by aspartic acid and substitution of the 246th glutamine by arginine in an amino acid sequence represented by SEQ ID NO: 3.

(8) Recombinant Vector Containing Polynucleotide Encoding Present Invented Protein (A) Having Altered Amino Acid Sequence V109I/G191D/Q246R Using an oligonucleotide having a base sequence represented by SEQ ID NO: 38 and an oligonucleotide having a base sequence represented by SEQ ID NO: 39, which are primers for mutation introduction for converting the 737th adenine in a base sequence represented by SEQ ID NO: 13 to guanine, as a primer, PCR was performed using the plasmid pTrc43SCcHis-g325a/g572a mentioned in Example 7 (5) as a template and with the following reaction solution composition using the QuikChange II Site-Directed Mutagenesis Kit (manufactured by STRATAGENE).

[Reaction Solution Composition]
DNA solution of pTrc43SCcHis-g325a/g572a: 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit): 1 µl
Ultrapure water: 41.2 µl A container containing a reaction solution with the above composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 5.5 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, *E. coli* DH5α was transformed.

From the transformants thus obtained, plasmids were extracted, and then a base sequence at the mutation site was determined by the dideoxy method. A plasmid into which the designed mutation was confirmed to be introduced was designated as pTrc43SCcHis-g325a/g572a/a737g. The plasmid pTrc43SCcHis-g325a/g572a/a737g is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an altered amino acid sequence having substitution of the 109th valine by isoleucine, substitution of the 191st glycine by aspartic acid, and substitution of the 246th glutamine by arginine in an amino acid sequence represented by SEQ ID NO: 3.

Example 8

Thermal Stability Evaluation of Present Invented Protein (A)

(1)

An *E. coli* JM109 strain was transformed using the plasmid pTrc43SCcHis, pTrc43SCcHis-g325a/g572a, pTrc43SC cHis-g325a/a737g, or pTrc43SCcHis-g325a/g572a/a737g. The transformant thus obtained was inoculated into 20 ml of a sterilized LB medium containing 0.1 mM IPTG and 50 µg/ml of ampicillin, and the medium was cultured by shaking at 30° C. for 15 hours. Each of the culture solutions thus obtained was centrifuged to obtain about 0.1 g of wet cells. About 0.1 g of each of the wet cells was suspended in 1 ml of 20 mM phosphate buffer (pH 7.4) containing 0.5 M NaCl and 5 mM imidazole (namely the binding buffer), and disrupted at 2,500 rpm for 20 minutes using the Multi-beads shocker (manufactured by Yasui Kikai Corporation) and glass beads (0.1 mmΦ). The disruption liquid thus obtained was centrifuged at 13,000 rpm and 4° C. for 10 minutes to obtain about 0.7 ml of each of centrifuged supernatant liquid.

About 0.3 ml of the binding buffer was added to each of the centrifuged supernatant liquid thus obtained to make about 1 ml, and then this solution was applied to an affinity column (HisTrap HP, gel bed 1 ml, GE Healthcare Japan). By passing about 3 ml of the binding buffer through this column, non-adsorbed proteins were eluted. Then, by passing about 2 ml of 20 mM phosphate buffer (pH 7.4) containing 0.5 M NaCl and 500 mM imidazole through this column, each adsorbed protein was eluted, and eluates were collected. About 2 ml of each eluate was subjected to the Amicon Ultra-15 (manufactured by Merck Millipore), and desalting and concentration was performed and the buffer was replaced by 0.5 M Tris-HCl (pH 9) to obtain about 0.4 ml of each of purified enzyme solutions. The protein concentration of each purified enzyme solution was measured. The protein concentration of the purified enzyme solution from the pTrc43SCcHis-introduced transformant was 3.1 g protein/L, that from the pTrc43SCcHis-g325a/g572a-introduced transformant was 2.5 g protein/L, that from the pTrc43SCcHis-g325a/a737g-introduced transformant was 3.1 g protein/L, and that from the pTrc43SCcHis-g325a/g572a/a737g-introduced transformant was 3.2 g protein/L.

Each of the purified enzyme solutions thus obtained was diluted so that the concentration was 0.45 g protein/L, and 0.06 ml of the diluted enzyme solution thus obtained was heated at 41° C. for 30 minutes and then cooled to 4° C. After 0.045 ml of the enzyme solution thus obtained was mixed with 0.055 ml of 0.5 M Tris-HCl buffer (pH 9.0), calcium 2-hydroxy-4-(methylthio)butyrate (manufactured by Tokyo Chemical Industry) and NAD+ were added so that the concentration was 47 mM and 3.2 mM, respectively, and the solution was incubated at 30° C. The absorbance of the reaction solution was measured at a wavelength of 340 nm for about 10 minutes at 10-second intervals. The enzyme activity was calculated by defining the enzyme amount which reduces 1 pmol of NAD+ per minute as 1 U. A reaction was performed in the same manner using a non-heated diluted enzyme solution as a control, and the absorbance of the reaction solution was measured to calculate the enzyme activity. By defining the enzyme activity in a reaction using a non-heated diluted enzyme solution as 100%, the remaining activity of a heated diluted enzyme solution was calculated. The results are shown in Table 2.

column (HisTrap HP, gel bed 1 ml, GE Healthcare Japan). By passing about 3 ml of the binding buffer through this column, non-adsorbed proteins were eluted. Then, by passing about 2 ml of 20 mM phosphate buffer (pH 7.4) containing 0.5 M NaCl and 500 mM imidazole through this column, each adsorbed protein was eluted, and eluates were collected. About 2 ml of each eluate was subjected to the Amicon Ultra-15 (manufactured by Merck Millipore), and desalting and concentration was performed and the buffer was replaced by 0.5 M Tris-HCl (pH 9) to obtain about 0.4 ml of each of purified enzyme solutions. The protein concentration of each purified enzyme solution was measured. The protein concentration of the purified enzyme solution from the pTrc43SCcHis-introduced transformant was 2.3 g protein/L, that from the pTrc43SCcHis-g325a-introduced transformant was 2.9 g protein/L, that from the pTrc43SCcHis-g572a-introduced transformant was 2.9 g protein/L, that from the pTrc43SCcHis-a737g-introduced transformant was 4.2 g protein/L, that from the pTrc43SCcHis-g325a/g572a-introduced transformant was 2.1 g protein/L, that from the pTrc43SCcHis-g572a/a737g-introduced transformant was 3.3 g protein/L, that from the pTrc43SCcHis-g325a/a737g-introduced transformant was 2.6 g protein/L, and that from the pTrc43SCcHis-g325a/g572a/a737g-introduced transformant was 2.7 g protein/L.

TABLE 2

| Enzyme solution | | Remaining activity (%) | |
| --- | --- | --- | --- |
| Introduced plasmid | Amino acid sequence | Non-heated | Heated (41° C., 30 min) |
| pTrc43SCcHis | SEQ ID NO: 3 | 100 | 0 |
| pTrc43SCcHis-g325a/g572a | V109I/G191D | 100 | 51.6 |
| pTrc43SCcHis-g325a/a737g | V109I/Q246R | 100 | 56.4 |
| pTrc43SCcHis-g325a/g572a/a737g | V109I/G191D/Q246R | 100 | 59.9 |

(2)

An *E. coli* JM109 strain was transformed using the pTrc43SCcHis, pTrc43SCcHis-g325a, pTrc43SCcHis-g572a, pTrc435SCcHis-a737g, pTrc43SCcHis-g325a/g572a, pTrc43SC cHis-g572a/a737g, pTrc43SCcHis-g325a/a737g, or pTrc43SCcHis-g325a/g572a/a737g. The transformant thus obtained was inoculated into 20 ml of a sterilized LB medium containing 0.1 mM IPTG and 50 µg/ml of ampicillin, and the medium was cultured by shaking at 30° C. for 15 hours. Each of the culture solutions thus obtained was centrifuged to obtain about 0.1 g of wet cells. About 0.1 g of each of the wet cells was suspended in 1 ml of 20 mM phosphate buffer (pH 7.4) containing 0.5 M NaCl and 5 mM imidazole (namely the binding buffer), and disrupted at 2,500 rpm for 20 minutes using the Multi-beads shocker (manufactured by Yasui Kikai Corporation) and glass beads (0.1 mmΦ). The disruption liquid thus obtained was centrifuged at 12,000 rpm and 4° C. for 10 minutes to obtain about 0.7 ml of each of centrifuged supernatant liquid.

About 0.3 ml of the binding buffer was added to each of the centrifuged supernatant liquid thus obtained to make about 1 ml, and then this solution was applied to an affinity Each of the purified enzyme solutions thus obtained was diluted so that the concentration was 0.45 g protein/L, and 0.06 ml of the diluted enzyme solution thus obtained was heated at 40.5° C. for 30 minutes and then cooled to 4° C. After 0.045 ml of the enzyme solution thus obtained was mixed with 0.055 ml of 0.5 M Tris-HCl buffer (pH 9.0), calcium 2-hydroxy-4-(methylthio)butyrate (manufactured by Tokyo Chemical Industry) and NAD+ were added so that the concentration was 47 mM and 3.2 mM, respectively, and the solution was incubated at 30° C. The absorbance of the reaction solution was measured at a wavelength of 340 nm for about 10 minutes at 10-second intervals. The enzyme activity was calculated by defining the enzyme amount which reduces 1 µmol of NAD+ per minute as 1 U. A reaction was performed in the same manner using a non-heated diluted enzyme solution as a control, and the absorbance of the reaction solution was measured to calculate the enzyme activity. By defining the enzyme activity in a reaction using a non-heated diluted enzyme solution as 100%, the remaining activity of a heated diluted enzyme solution was calculated. The results are shown in Table 3.

TABLE 3

| Enzyme solution | | Remaining activity (%) | |
|---|---|---|---|
| Introduced plasmid | Amino acid sequence | Non-heated | Heated (40.5° C., 30 min) |
| PTrc43SCcHis | SEQ ID NO: 3 | 100 | 6.9 |
| pTrc43SCcHis-g325a | V109I | 100 | 16.6 |
| pTrc43SCcHis-g572a | G191D | 100 | 8.1 |
| pTrc43SCcHis-a737g | Q246R | 100 | 22.5 |
| pTrc43SCcHis-g325a/g572a | V109I/G191D | 100 | 10.9 |
| pTrc43SCcHis-g572a/a737g | G191D/Q246R | 100 | 11.9 |
| pTrc43SCcHis-g325a/a737g | V109I/Q246R | 100 | 53.1 |
| pTrc43SCcHis-g325a/g572a/a737g | V109I/G191D/Q246R | 100 | 65.1 |

Example 9 (Preparation of Present Invented Recombinant Vector (ABC) and Transformant Having the Vector)

(1) Present Invented Recombinant Vector (ABC) Containing Polynucleotide Encoding Present Invented Protein (A) Having Amino Acid Sequence Represented by SEQ ID NO: 3
(1-1) Recombinant Vector Containing Present Polynucleotide (C)

Based on a base sequence of a leucine dehydrogenase derived from a *Bacillus sphaericus* IFO3525 strain mentioned in Journal of Molecular Catalysis B: Enzymatic 23 (2003) 239-247, an oligonucleotide having a base sequence represented by SEQ ID NO: 22 (CGTAGCTTAC AAACTTTGCGAGTATTTAC) (sense primer) and an oligonucleotide having a base sequence represented by SEQ ID NO: 23 (GTAAATACTCGCAAAGTTTGTAAGCTACG) (antisense primer) are synthesized as a primer for mutation introduction for converting the 561st guanine to adenine.

Using an oligonucleotide having a base sequence represented by SEQ ID NO: 22 and an oligonucleotide having a base sequence represented by SEQ ID NO: 23 as a primer, PCR was performed using the plasmid pETLD(A113G) mentioned in Example 3 (3-2) as a template and with the following reaction solution composition using the QuikChange II Site-Directed Mutagenesis Kit (manufactured by STRATAGENE).
[Reaction Solution Composition]
DNA solution of pETLD(A113G): 1 µl
dNTP mix (contained in the above Kit): 1 µl
Sense primer (50 µM): 0.4 µl
Antisense primer (50 µM): 0.4 µl
10× buffer (contained in the above Kit): 5 µl
PfuUltra (contained in the above Kit): 1 µl
Ultrapure water: 41.2 µl
[PCR Reaction Condition]
A container containing a reaction solution with the above reaction solution composition was set in a thermal cycler (PERKIN ELMER-GeneAmp PCR System 2400) and incubated at 95° C. for one minute, and an incubation cycle consisting of incubation at 95° C. for 50 seconds, followed by 60° C. for one minute, followed by 68° C. for 6.8 minutes was performed 12 times, and then the solution was stored at 4° C.

To the PCR reaction solution thus obtained, 1 µl of a DpnI restriction enzyme (contained in the above Kit) was added, and then the solution was incubated at 37° C. for 1 hour. Using the incubated solution thus obtained, *E. coli* DH5α was transformed.

From the transformants thus obtained, plasmids were extracted, and then a base sequence at the mutation site was determined by the dideoxy method. A plasmid into which the designed mutation was confirmed to be introduced was designated as pETLD(A113G)hd.

By adding restriction enzymes NcoI and BamHI to the plasmid pETLD(A113G)hd, the plasmid DNA was double-digested, and enzymatically digested DNA of about 1.1 kb was purified.

Plasmid vector pTrc99A (manufactured by GE Healthcare Japan) was double-digested with restriction enzymes NcoI and BamHI, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 µg/ml of ampicillin, 10 colonies were randomly selected from the growing colonies. Each of the selected colonies was inoculated into 2 ml of a sterilized LB medium containing 50 µg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and BamHI, and then subjected to agarose gel electrophoresis. In each of four plasmids, DNA of about 1.1 kb was confirmed to be inserted into the above vector. One of these plasmids was designated as pTrcLD(A113G)nh. The plasmid pTrcLD(A113G)nh is designed so that it can express a protein having an amino acid sequence in which an amino acid sequence composed of 20 amino acids including consecutive 6 residues of histidine (SEQ ID NO: 44: MetGlySerSerHisHisHisHisHisHisSerSerGlyLeuValProArgGlySerHis) is added to the amino terminus of an amino acid sequence represented by SEQ ID NO: 7.

(1-2) Recombinant Vector Containing Present Invented Polynucleotide (B)

Using an oligonucleotide having a base sequence represented by SEQ ID NO: 24 (CCATGGCTATGAAAAAGCTCTCCATCGCCC) (sense primer) and an oligonucleotide having a base sequence represented by SEQ ID NO: 40 (GCTGCAGCTCAGTGGTGGTGGTGGTGGG) (antisense primer) as a primer, PCR was performed using the plasmid pET774 mentioned in Example 1 (2) as a template and with the following reaction solution composition.
[Reaction Solution Composition]
DNA solution of plasmid pET774: 1.5 µl
dNTP (a mixture of 2 mM each): 10 µl
Primer (50 pmol/µl): 0.3 µl each
2× buffer: 25 µl
KOD-FX (1 U/µl, Toyobo): 1 µl
Ultrapure water: 11.9 µl A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.1 kb was detected.

By adding restriction enzymes NcoI and PstI to the remaining PCR reaction solution, DNA was double-digested, and enzymatically digested DNA of about 1.1 kb was purified.

Plasmid vector pTrc99A (manufactured by GE Healthcare Japan) was double-digested with restriction enzymes NcoI and PstI, and enzymatically digested vector DNA was purified.

These purified DNAs were mixed and ligated with a T4 DNA ligase, and using the ligation solution thus obtained, $E.\ coli$ DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and PstI, and then subjected to agarose gel electrophoresis. In each of six plasmids, DNA of about 1.1 kb was confirmed to be inserted into the above vector. One of these plasmids was designated as pTrc774chNP. The plasmid pTrc774chNP is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an amino acid sequence represented by SEQ ID NO: 1.

(1-3) Recombinant Vector Containing Present Invented Polynucleotide (B) and Present Polynucleotide (C)

Using an oligonucleotide having a base sequence represented by SEQ ID NO: 26 (CGGATCCGAGGAAACA-GACCATGG) (sense primer) and an oligonucleotide having a base sequence represented by SEQ ID NO: 40 (GCTGCA-GCTCAGTGGTGGTGGTGGTGGTG) (antisense primer) as a primer, PCR was performed using the plasmid pTrc774chNP mentioned in Example 9 (1-2) as a template and with the following reaction solution composition.
[Reaction Solution Composition]
DNA solution of pTrc774chNP: 1.5 μl
dNTP (a mixture of 2 mM each): 10 μl
Primer (50 pmol/μl): 0.3 μl each
2× buffer: 25 μl
KOD-FX (1 U/μl, Toyobo): 1 μl
Ultrapure water: 11.9 μl A container containing a reaction solution with the above composition was set in a thermal cycler (PERKIN ELMER-GeneAmp PCR System 9700) and incubated at 94° C. for 2 minutes, and an incubation cycle consisting of incubation at 98° C. for 10 seconds, followed by 60° C. for 30 seconds, followed by 68° C. for 60 seconds was performed 30 times, and then the solution was maintained at 4° C.

Subsequently, a part of the above PCR reaction solution was subjected to agarose gel electrophoresis. A DNA band of about 1.1 kb was detected.

By adding restriction enzymes BamHI and PstI to the remaining PCR reaction solution, DNA was double-digested, and enzymatically digested DNA of about 1.1 kb was purified.

The plasmid pTrcLD(A113G)nh mentioned in Example 9 (1-1) was double-digested with restriction enzymes BamHI and PstI, and enzymatically digested plasmid DNA was purified.

These purified DNAs were mixed and ligated with a T4 DNA ligase, and using the ligation solution thus obtained, $E.\ coli$ DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes BamHI and PstI, and then subjected to agarose gel electrophoresis. In each of six plasmids, DNA of about 1.1 kb was confirmed to be inserted into the plasmid pTrcLD(A113G)nh. One of these plasmids was designated as plasmid pTrcLD(A113G)nh/774ch.

(1-4) Recombinant Vector Containing Present Invented Polynucleotide (A)

An oligonucleotide having a base sequence represented by SEQ ID NO: 32 (GCCATGGCTATGTCTCAAAAAC-CAAAAATC) (sense primer) and an oligonucleotide having a base sequence represented by SEQ ID NO: 41 (CAAGCT-TGTCAGTGGTGGTGGTGGTGGTG) (antisense primer) are synthesized. Using an oligonucleotide primer having a base sequence represented by SEQ ID NO: 32 and an oligonucleotide primer having a base sequence represented by SEQ ID NO: 41, PCR was performed using the plasmid pET43SCcHis mentioned in Example 7 (1-1) as a template and with the following reaction solution composition using the Expand High Fidelity PCR System (Roche Diagnostics).
[Reaction Solution Composition]
DNA solution of pET43SCcHis: 1 μl
dNTP (a mixture of 2.5 mM each): 1 μl
Primer (20 pmol/μl): 0.4 μl each
5× buffer (with $MgCl_2$): 10 μl
enz.expandHiFi (3.5×10³ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 55° C. for 30 seconds, followed by 72° C. for 1.5 minutes was performed 10 times, and then an incubation cycle consisting of incubation at 94° C. for 15 seconds, followed by 60° C. for 30 seconds, followed by 72° C. for 1.5 minutes was performed 20 times, and further the solution was maintained at 72° C. for 7 minutes.

Subsequently, a part of the above PCR reaction solution was subjected to agarose gel electrophoresis. A DNA band of about 1.0 kb was detected.

By adding restriction enzymes NcoI and HindIII to the remaining PCR reaction solution, DNA was double-digested, and enzymatically digested DNA of about 1.0 kb was purified.

Plasmid vector pTrc99A (manufactured by GE Healthcare Japan) was double-digested with restriction enzymes NcoI and HindIII, and enzymatically digested vector DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, 10 colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes NcoI and HindIII, and then subjected to agarose gel electrophoresis. In each of four plasmids, DNA of about 1.0 kb was confirmed to be inserted into the above vector. One of these plasmids was designated as pTrc43SCchNH. The plasmid pTrc43SCchNH is designed so that it can express a protein having an amino acid sequence in which an amino acid sequence composed of 8 amino acids including consecutive 6 residues of histidine (SEQ ID NO: 45: LeuGluHisHisHisHisHisHis) is added to the carboxy terminus of an amino acid sequence represented by SEQ ID NO: 3.

(1-5) Recombinant Vector Containing Present Invented Polynucleotide (A), Present Invented Polynucleotide (B), and Present Polynucleotide (C)

Using an oligonucleotide having a base sequence represented by SEQ ID NO: 28 (GCTGCAGCAGGAAACA-GACCATGG) (sense primer) and an oligonucleotide having a base sequence represented by SEQ ID NO: 41 (CAAGCT-TGTCAGTGGTGGTGGTGGTGGTG) (antisense primer) as a primer, PCR was performed using the plasmid pTrc43SCchNH mentioned in Example 9 (1-4) as a template and with the following reaction solution composition using the Expand High Fidelity PCR System (Roche Diagnostics).

[Reaction Solution Composition]
DNA solution of pTrc43SCchNH: 1 μl
dNTP (a mixture of 2.5 mM each): 1 μl
Primer (20 pmol/μl): 0.4 μl each
5× buffer (with MgCl$_2$): 10 μl
enz.expandHiFi (3.5×10$^3$ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 65° C. for 30 seconds, followed by 72° C. for one minute was performed 10 times, and then an incubation cycle consisting of incubation at 94° C. for 15 seconds, followed by 70° C. for 30 seconds, followed by 72° C. for one minute was performed 20 times, and further the solution was maintained at 72° C. for 7 minutes.

Subsequently, a part of the above PCR reaction solution was subjected to agarose gel electrophoresis. A DNA band of about 1.0 kb was detected.

By adding restriction enzymes PstI and HindIII to the remaining PCR reaction solution, a DNA fragment was double-digested, and enzymatically digested DNA of about 1.0 kb was purified.

The plasmid pTrcLD(A113G)nh/774ch mentioned in Example 9 (1-3) was double-digested with restriction enzymes PstI and HindIII, and enzymatically digested plasmid DNA was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes PstI and HindIII, and then subjected to agarose gel electrophoresis. In each of six plasmids, DNA of about 1.0 kb was confirmed to be inserted into the plasmid pTrcLD(A113G)nh/774ch. One of these plasmids was designated as pTrcLD(A113G)nh/774ch/43SCch.

(2) Present Invented Recombinant Vector (ABC) Containing Polynucleotide Encoding Present Invented Protein (A) Having Altered Amino Acid Sequence V109I/G191D/Q246R Using an oligonucleotide having a base sequence represented by SEQ ID NO: 28 (GCTGCAGCAGGAAACA-GACCATGG) (sense primer) and an oligonucleotide having a base sequence represented by SEQ ID NO: 41 (CAAGCT-TGTCAGTGGTGGTGGTGGTGGTG) (antisense primer) as a primer, PCR was performed using the plasmid pTrc43SCcHis-g325a/g572a/a737g mentioned in Example 7 (8) as a template and with the following reaction solution composition using the Expand High Fidelity PCR System (Roche Diagnostics).

[Reaction Solution Composition]
DNA solution of pTrc43SCcHis-g325a/g572a/a737g: 1 μl
dNTP (a mixture of 2.5 mM each): 1 μl
Primer (20 pmol/μl): 0.4 μl each
5× buffer (with MgCl$_2$): 10 μl
enz.expandHiFi (3.5×10$^3$ U/ml): 0.5 μl
Ultrapure water: 36.7 μl A container containing a reaction solution with the above composition was set in a thermal cycler (PERKIN ELMER-GeneAmp PCR System 2400) and incubated at 94° C. for 2 minutes, and an incubation cycle consisting of incubation at 94° C. for 15 seconds, followed by 65° C. for 30 seconds, followed by 72° C. for one minute was performed 10 times, and then an incubation cycle consisting of incubation at 94° C. for 15 seconds, followed by 70° C. for 30 seconds, followed by 72° C. for one minute was performed 20 times, and further the solution was maintained at 72° C. for 7 minutes.

Subsequently, a part of the above PCR reaction solution was subjected to agarose gel electrophoresis. A DNA band of about 1.0 kb was detected.

By adding restriction enzymes PstI and HindIII to the remaining PCR reaction solution, DNA was double-digested, and enzymatically digested DNA of about 1.0 kb was purified.

The plasmid TrcLD(A113G)nh/774ch/43SCch mentioned in Example 9 (1-5) was double-digested with restriction enzymes PstI and HindIII, and enzymatically digested plasmid DNA of about 6.4 kb was purified.

These purified DNAs were mixed and ligated with a T4 DNA ligase, and using the ligation solution thus obtained, *E. coli* DH5α was transformed.

The transformant thus obtained was cultured in an LB agar medium containing 50 μg/ml of ampicillin, eight colonies were randomly selected from the growing colonies. Each of the selected colonies was inoculated into 2 ml of a sterilized LB medium containing 50 μg/ml of ampicillin, and the medium was cultured by shaking in a test tube at 37° C. for 17 hours. Plasmids were removed from each cultured cell using the QIAprep Spin Miniprep Kit (manufactured by Qiagen). A part of each of the removed plasmids was double-digested with restriction enzymes PstI and HindIII, and then subjected to agarose gel electrophoresis. In each of six plasmids, DNA of about 1.0 kb was confirmed to be inserted into the above plasmid DNA of about 6.4 kb. One of these plasmids was designated as pTrcLD(A113G)nh/774ch/43SCMch.

Example 10 (Preparation of L-α-Amino Acid Compound Using Treated Product of Transformant Having Present Invented Recombinant Vector (ABC))

(1) Transformant Having Present Invented Recombinant Vector (ABC) Containing Polynucleotide Encoding Present Invented Protein (A) Having Amino Acid Sequence Represented by SEQ ID NO: 3

An *E. coli* JM109 strain was transformed using the plasmid pTrcLD(A113G)nh/774ch/43SCch. The transformant thus obtained was inoculated into 20 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 0.1 g of the wet cells were suspended in 1 ml of 0.5 M Tris-HCl buffer (pH 9), and disrupted at 2,500 rpm for 20 minutes using the Multi-beads shocker (manufactured by Yasui Kikai Corporation) and glass beads (0.1 mm). The disruption liquid thus obtained was centrifuged at 8,000 rpm and 4° C. for 10 minutes to obtain about 0.7 ml of centrifuged supernatant liquid.

With 0.1 ml of the centrifuged supernatant liquid thus obtained, 0.4 ml of a 40% aqueous solution of 2-hydroxy-4-(methylthio)butyric acid (manufactured by Tokyo Chemical Industry) whose pH was adjusted to 9 with ammonia water, 10 mg of NAD+, and 20 mg of ammonium sulfate were mixed, and the solution was shaken at 30° C. for 18 hours. This reaction solution was subjected to content analysis by liquid chromatography under the following condition. It was found that 85.1 g/L of L-methionine was produced. The yield of L-methionine based on the amount of 2-hydroxy-4-(methylthio)butyric acid used for the reaction was 21.5%.

(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm (2) Transformant Having Present Invented Recombinant Vector (ABC) Containing Polynucleotide Encoding Present Invented Protein (A) Having Altered Amino Acid Sequence V109I/G191D/Q246R An *E. coli* JM109 strain was transformed using the plasmid pTrcLD(A113G)nh/774ch/43SCMch. The transformant thus obtained was inoculated into 20 ml of a sterilized LB medium containing 0.1 mM IPTG and 50 μg/ml of ampicillin, and the medium was cultured by shaking at 30° C. for 15 hours. The culture solution thus obtained was centrifuged to obtain wet cells. About 0.1 g of the wet cells were suspended in 1 ml of 0.5 M Tris-HCl buffer (pH 9), and disrupted at 2,500 rpm for 20 minutes using the Multi-beads shocker (manufactured by Yasui Kikai Corporation) and glass beads (0.1 mmΦ). The disruption liquid thus obtained was centrifuged at 8,000 rpm and 4° C. for 10 minutes to obtain about 0.7 ml of centrifuged supernatant liquid.

With 0.1 ml of the centrifuged supernatant liquid thus obtained, 0.4 ml of a 40% aqueous solution of 2-hydroxy-4-(methylthio)butyric acid (manufactured by Tokyo Chemical Industry) whose pH was adjusted to 9 with ammonia water, 10 mg of NAD+, and 20 mg of ammonium sulfate were mixed, and the solution was shaken at 30° C. for 2 hours. This reaction solution was subjected to content analysis by liquid chromatography under the following condition. It was found that 82.5 g/L of L-methionine was produced. The yield of L-methionine based on the amount of 2-hydroxy-4-(methylthio)butyric acid used for the reaction was 20.8%.

(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm Example 11 (Preparation of L-α-Amino Acid Compound Using Present Invented Protein (A), Present Invented Protein (B), and Present Protein (C))

(1) Production of L-α-Amino Acid Compound Using Present Invented Protein (A), Present Invented Protein (B), and Present Protein (C) Having Amino Acid Sequence Represented by SEQ ID NO: 3

After 0.1 ml of a 2-fold diluent of the purified enzyme solution of the present invented protein (B) prepared in Example 2 (1) (40 g protein/L, was mixed with 0.1 ml of a 2-fold concentrated solution of the purified enzyme solution of the present invented protein (A) prepared in Example 2 (2) (9 g protein/L) and 0.1 ml of a 2-fold diluent of the leucine dehydrogenase (A113G) purified enzyme solution prepared in Example 3 (4) (32.6 g protein/L), the mixture was concentrated with the Amicon Ultra-15 (manufactured by Merck Millipore) to obtain 0.1 ml of a purified enzyme mixture. With 0.1 ml of the purified enzyme mixture thus obtained, 0.1 ml of a 40% aqueous solution of DL-α-hydroxy-isocaproic acid (ACROSORGANICS) whose pH was adjusted to 9 with ammonia water, 10 mg of NAD+, 0.3 ml of 0.5 M Tris-HCl buffer (pH 9.0), and 20 mg of ammonium sulfate were mixed, and the solution was shaken at 30° C. for 18 hours. This reaction solution was subjected to content analysis by liquid chromatography under the following condition. It was found that L-leucine was produced in a proportion of 60.9% based on the amount of DL-α-hydroxy-isocaproic acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm
(2) Preparation of L-α-Amino Acid Compound Using Present Invented Protein (A), Present Invented Protein (B), and Present Protein (C) Having Altered Amino Acid Sequence V109I/G191D/0246R After 0.1 ml of a 2.5-fold diluent of the purified enzyme solution of the present invented protein (B) prepared in Example 2 (1) (40 g protein/L) was mixed with 0.1 ml of a 4.5-fold concentrated solution of the purified enzyme solution of the present invented protein (A) prepared from the pTrc43SCcHis-g325a/g572a/a737g transformant in Example 8 (1) (3.2 g protein/L) and 0.1 ml of a 2-fold diluent of the leucine dehydrogenase (A113G) purified enzyme solution prepared in Example 3 (4) (32.6 g protein/L), the mixture was concentrated with the Amicon Ultra-15 (manufactured by Merck Millipore) to obtain 0.1 ml of a purified enzyme mixture. With 0.1 ml of the purified enzyme mixture thus obtained, 0.1 ml of a 40% aqueous solution of DL-α-hydroxy-isocaproic acid (manufactured by ACROS ORGANICS) whose pH was adjusted to 9 with ammonia water, 10 mg of NAD+, 0.3 ml of 0.5 M Tris-HCl buffer (pH 9.0), and 20 mg of ammonium sulfate were mixed, and the solution was shaken at 30° C. for 18 hours. This reaction solution was subjected to content analysis by liquid chromatography under the following condition. It was found that L-leucine was produced in a proportion of 88.0% based on the amount of DL-α-hydroxy-isocaproic acid used for the reaction.
(Content Analysis Condition)
Column: UNISON UK-C18 (4.6 mmφ×25 cm, 3 μm)
Mobile phase: A mixture of a 12 mM sodium 1-heptanesulfonate solution containing 50 mM phosphoric acid (Solution A) and acetonitrile (Solution B) in a rate of Solution A (%):Solution B (%)=90:10
Flow rate: 0.8 ml/min
Column temperature: 37° C.
Detection: 210 nm

INDUSTRIAL APPLICABILITY

According to the present invention, it is possible to provide an oxidase, a polynucleotide encoding the same, a method for producing an α-amino acid compound such as methionine and leucine using these, and the like.

SEQUENCE LISTING FREE TEXT

SEQ ID NO: 9-12
An oligonucleotide primer designed for PCR
SEQ ID NO: 13
A polynucleotide encoding a dehydrogenase
SEQ ID NO: 14-41
An oligonucleotide primer designed for PCR
SEQ ID NO: 44-45
An amino acid sequence designed

The invention claimed is:

1. A method for producing an L-α-amino acid compound, which comprises (1) the step of reacting any one or both of a protein having any one of the following amino acid sequences (A1) to (A4) and having the ability to oxidize an α-hydroxycarboxylic acid compound and convert the same into a corresponding α-oxocarboxylic acid compound:

(A1) the amino acid sequence of SEQ ID NO: 3, (A2) an amino acid sequence i) having at least 95% sequence identity to the amino acid sequence of SEQ ID NO: 3, and ii) of a protein having any one or both of the ability to oxidize a 2-hydroxy-4-(methylthio) butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, (A3) an amino acid sequence i) comprising SEQ ID NO: 3 in which one or plural amino acids are deleted, substituted, or added, wherein the plural amino acids are 2, 3, 4, 5, 6, 7, or 10 amino acids, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or (A4) an amino acid sequence i) comprising SEQ ID NO: 3 altered by one or more amino acid substitutions selected from the group consisting of substitution of the 109th valine by isoleucine, substitution of the 191st glycine by aspartic acid, and substitution of the 246th glutamine by arginine, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative;

and a protein having any one of the following amino acid sequences (B1) to (B3):

(B1) the amino acid sequence of SEQ ID NO: 1

(B2) an amino acid sequence i) having at least 95% sequence identity to the amino acid sequence of SEQ ID NO: 1, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative, or (B3) an amino acid sequence i) comprising SEQ ID NO: 1 in which one or plural amino acids are deleted, substituted, or added, wherein the plural amino acids are 2, 3, 4, 5, 6, 7, or 10 amino acids, and ii) of a protein having any one or both of the ability to oxidize a 2-hydroxy-4-(methylthio)butyric acid derivative and convert the same into a corresponding 2-oxo-4-(methylthio)butyric acid derivative and the ability to oxidize an α-hydroxy-isocaproic acid derivative and convert the same into a corresponding α-oxo-isocaproic acid derivative;

with an α-hydroxycarboxylic acid compound to obtain a corresponding α-oxocarboxylic acid compound, and (2) the step of reacting a protein having the ability to aminate an α-oxocarboxylic acid compound and convert the same into a corresponding L-α-amino acid compound with the α-oxocarboxylic acid compound obtained in the step (1) to obtain a corresponding L-α-amino add compound as the produced L-α-amino add compound.

2. The production method according to claim 1, wherein the α-hydroxycarboxylic acid compound is a sulfur-containing α-hydroxycarboxylic acid compound, the corresponding α-oxocarboxylic acid compound is a sulfur-containing α-oxocarboxylic acid compound, the corresponding L-α-amino acid compound is a sulfur-containing L-α-amino acid compound, the protein reacted with an α-hydroxycarboxylic acid compound in the step (1) is a protein at least having the ability to oxidize a 2-hydroxy-4-(methylthio)butyric acid derivative and convert the same into a corresponding 2-oxo-4-(methylthio)butyric acid derivative.

3. The production method according to claim 2, wherein the sulfur-containing α-hydroxycarboxylic acid compound is a compound of formula (1):

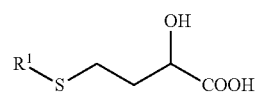

wherein R¹ represents a hydrogen atom or an optionally substituted C1-8 alkyl group;

the sulfur-containing α-oxocarboxylic acid compound is a compound of formula (2):

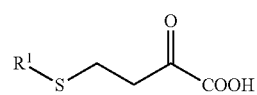

wherein R¹ is the same as defined above;

and the sulfur-containing L-α-amino acid compound is a compound of formula (3):

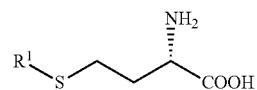

wherein R¹ is the same as defined above.

4. The production method according to claim 1, wherein the α-hydroxycarboxylic acid compound is α-hydroxy-isocaproic acid, the corresponding α-oxocarboxylic acid compound is α-oxo-isocaproic acid, the corresponding L-α-amino acid compound is L-leucine, and the protein reacted with an α-hydroxycarboxylic acid compound in the step (1) is a protein at least having the ability to oxidize an α-hydroxy-isocaproic acid derivative and convert the same into a corresponding α-oxo-isocaproic acid derivative.

5. The production method according to claim 1, wherein the protein having the ability to aminate an α-oxocarboxylic acid compound and convert the same into a corresponding L-α-amino acid compound is a leucine dehydrogenase.

6. The production method according to claim 1, wherein the amino acid sequence of the protein having the ability to aminate an α-oxocarboxylic acid compound and convert the same into a corresponding L-α-amino acid compound is any one of the following amino acid sequences (C1) to (C3):

(C1) the amino acid sequence of SEQ ID NO: 7, (C2) an amino acid sequence i) having at least 90% sequence identity to the amino acid sequence of SEQ ID NO: 7, and ii) of a protein having the ability to aminate an α-oxocarboxylic acid compound and convert the same into a corresponding L-α-amino add compound, or (C3) an amino acid sequence i) comprising SEQ ID NO: 7 in which one or plural amino acids are deleted, substituted, or added, wherein the plural amino adds are 2, 3, 4, 5, 6, 7, 10, 15, 18, 20, 25, 30, 35, 36, or 40 amino acids, and II) of a protein having the ability to aminate an α-oxocarboxylic add compound and convert the same into a corresponding L-α-amino add compound.

7. The production method according to claim 1, wherein the protein reacted with the α-hydroxycarboxylic acid compound in the step (1) is provided in a reaction system in the form in which the protein is included in a transformant in which a polynucleotide encoding the protein is introduced into a host cell or in a treated product of the transformant selected from the group consisting of a freeze-dried transformant, an organic solvent-treated transformant, a dried transformant, a triturated transformant, an autolysate of a transformant, a sonicate of a transformant, a transformant extract, and an alkali-treated product of a transformant.

8. The production method according to claim 7, wherein the transformant is a transformant in which a recombinant vector comprising a polynucleotide encoding any one of amino acid sequences (A1) to (A3) or (A5) or a polynucleotide encoding any one of amino acid sequences (B1) to (B3) is introduced into the host cell or in the treated product thereof.

9. The production method according to claim 1, wherein the protein having the ability to aminate an α-oxocarboxylic acid compound and convert the same into a corresponding L-α-amino add compound is provided in a reaction system in the form in which the protein is included in a transformant in which a polynucleotide encoding the protein is introduced into a host cell or in a treated product of the transformant selected from the group consisting of a freeze-dried transformant; an organic solvent-treated transformant, a dried transformant, a triturated transformant, an autolysate of a transformant, a sonicate of a transformant, a transformant extract, and an alkali-treated product of a transformant.

10. The production method according to claim 9, wherein the transformant is a transformant in which a recombinant vector comprising the polynucleotide encoding any one of the amino acid sequences (C1) to (C3) is introduced into the host cell or in the freeze-dried transformant, organic solvent-treated transformant, dried transformant, triturated transformant, autolysate of a transformant, sonicate of a transformant, transformant extract, or alkali-treated product of a transformant:
   (C1) the amino acid sequence of SEQ ID NO: 7,
   (C2) an amino acid sequence i) having at least 90% sequence identity to the amino acid sequence of SEQ ID NO: 7, and ii) of a protein having the ability to aminate an α-oxocarboxylic acid compound and convert the same into a corresponding L-α-amino acid compound, or
   (C3) an amino acid sequence i) comprising SEQ ID NO: 7 in which one or plural amino acids are deleted, substituted, or added, wherein the plural amino acids are 2, 3, 4, 5, 6, 7, 10, 15, 18, 20, 25, 30, 35, 36, or 40 amino acids, and ii) of a protein having the ability to aminate are α-oxocarboxylic acid compound and convert the same into a corresponding L-α-amino acid compound.

11. The production method according to claim 1, wherein the step (1) is performed in the presence of a protein having the ability to convert a reduced β-nicotinamide adenine dinucleotide or a reduced β-nicotinamide adenine dinucleotide phosphate into its oxidized form.

12. The production method according to claim 11, wherein the protein having the ability to convert a reduced β-nicotinamide adenine dinucleotide or a reduced β-nicotinamide adenine dinucleotide phosphate into its oxidized form is the protein having the ability to aminate an α-oxocarboxylic acid compound and convert the same into a corresponding L-α-amino acid compound.

13. The production method according to claim 11, wherein the protein having the ability to convert a reduced β-nicotinamide adenine dinucleotide or a reduced β-nicotinamide adenine dinucleotide phosphate into its oxidized form is provided in a reaction system in the form in which the protein is included in a transformant in which a polynucleotide encoding the protein is introduced into a host cell or in a freeze-dried transformant, an organic solvent-treated transformant, a dried transformant, a triturated transformant, an autolysate of a transformant, a sonicate of a transformant, a transformant extract, or an alkali-treated product of a transformant.

14. The production method according to claim 1, wherein the step (2) is performed in the presence of a protein having the ability to convert an oxidized β-nicotinamide adenine dinucleotide or an oxidized β-nicotinamide adenine dinucleotide phosphate into its reduced form.

15. The production method according to claim 14, wherein the protein having the ability to convert an oxidized β-nicotinamide adenine dinucleotide or an oxidized β-nicotinamide adenine dinucleotide phosphate into its reduced form is the protein having the ability to oxidize an α-hydroxycarboxylic acid compound and convert the same into a corresponding α-oxocarboxylic acid compound.

16. The production method according to claim 14, wherein the protein having the ability to convert an oxidized β-nicotinamide adenine dinucleotide or an oxidized β-nicotinamide adenine dinucleotide phosphate into its reduced form is provided in a reaction system in the form in which the protein is included in a transformant in which a polynucleotide encoding the protein is introduced into a host cell or in a treated product of the transformant selected from the group consisting of a freeze-dried transformant, an organic solvent-treated transformant, a dried transformant, a triturated transformant, an autolysate of a transformant, a sonicate of a transformant, a transformant extract, and an alkali-treated product of a transformant.

17. The production method according to claim 1, wherein the step (1) and the step (2) are performed in one reaction system.

* * * * *

SEQUENCE LISTING

<160> NUMBER OF SEQ ID NOS: 45

<210> SEQ ID NO 1
<211> LENGTH: 353
<212> TYPE: PRT
<213> ORGANISM: Achromobacter denitrificans

<400> SEQUENCE: 1

Met Lys Lys Leu Ser Ile Ala Gln Ala Tyr Glu Tyr Gly Arg Arg Val
1               5                   10                  15

Leu Met Ala Gln Gly Val Pro Glu Asp Ile Ala Arg Asp Val Ala Glu
            20                  25                  30

His Leu Val Glu Ser Asp Arg Val Gly Tyr Ala Ser His Gly Leu Ser
        35                  40                  45

Ile Leu Thr Asn Tyr Arg Arg Val Leu Ser Glu Gly Leu Ala Arg Pro
    50                  55                  60

Asp Gly Arg Pro Glu Leu Val Asn Asp Arg Gly Ala Met Leu Ala Tyr
65                  70                  75                  80

Asp Gly His Asn Gly Leu Gly Gln Tyr Val Gly Lys Val Ile Glu
            85                  90                  95

Lys Ala Ile Glu Arg Thr Gln Glu His Gly Gln Cys Ile Leu Thr Leu
            100                 105                 110

Arg His Ser His His Leu Gly Arg Met Gly His Phe Gly Glu Met Val
        115                 120                 125

Ala Ala Lys Gly Leu Ile Leu Leu Ala Phe Thr Asn Val Ile Asn Arg
    130                 135                 140

Ala Pro Thr Val Ala Pro Phe Gly Gly Ala Gln Ala Cys Leu Thr Thr
145                 150                 155                 160

Asn Pro Leu Cys Phe Ala Gly Pro Leu Gly Gly Arg Pro Pro Phe
            165                 170                 175

Ile Val Asp Met Ala Thr Ser Ser Ile Ala Val Asn Lys Ala Arg Val
                180                 185                 190

Leu Ala Ala Lys Gly Glu Pro Ala Pro Glu Gly Ala Leu Ile Asp Ala
        195                 200                 205

Gln Gly Asn Pro Thr Thr Asp Pro Gly Ala Leu Phe Thr Asp Pro Pro
    210                 215                 220

Gly Ala Leu Leu Pro Phe Gly His Lys Gly Tyr Ala Leu Gly Leu
225                 230                 235                 240

Val Ala Glu Leu Leu Ala Gly Val Leu Ser Gly Gly Thr Ile Gln
                245                 250                 255

Pro Glu His Pro Arg Asn Gly Val Ala Thr Asn Asn Met Phe Ala Leu
                260                 265                 270

Leu Leu Asp Pro Gln Val Asp Phe Asn Thr Asp Trp Arg Ser Leu Glu
        275                 280                 285

Val Gly Ala Phe Ile Asp Tyr Leu His Ala Cys Lys Pro Gln Pro Gly
290                 295                 300

Val Glu Ser Val Gln Tyr Pro Gly Glu Tyr Glu Ala Arg Asn Arg Ala
305                 310                 315                 320

Ile Asn Ala Asp Thr Val Glu Phe Asp Thr Arg Ile Trp Glu Gly Leu
                325                 330                 335

Thr Arg Leu Ala Val Asp Leu Gly Val Pro Glu Ala Leu Pro His Glu
        340                 345                 350

Gly

<210> SEQ ID NO 2
<211> LENGTH: 1059
<212> TYPE: DNA
<213> ORGANISM: Achromobacter denitrificans

<400> SEQUENCE: 2

```
atgaaaaagc tctccatcgc ccaagcctat gaatacggcc gccgcgtgct gatggcgcaa    60
ggcgtgcccg aggacatcgc ccgcgacgtg gccgaacacc tggtcgaatc cgaccgcgtg   120
ggctacgcca gccacggcct gtccatcctg acgaactacc gccgcgtgct gtccgagggc   180
ctggcccgcc ccgacggccg ccccgaactg gtcaacgacc gcggcgccat gctggcctac   240
gacggccaca acggcctggg ccagtacgtc ggcaaggtgg tcatcgaaaa agccatcgag   300
cgcacccagg agcacggcca gtgcatcctg accctgcgcc acagccacca cctgggccgc   360
atgggccatt cggcgaaat ggtggcggcc aagggcctga tcctgctggc cttcaccaac   420
gtgatcaacc gcgccccac cgtggccccc ttcgcggcg cgcaggcctg cctgaccacc   480
aacccgctgt gcttcgccgg ccccctgccc ggaggccgcc cgcccttcat cgtggacatg   540
gccaccagct ccatcgccgt caacaaggcc cgcgtgctgg ccgccaaggg cgaacccgcc   600
cccgaaggcg cgctgatcga cgcccagggc aaccccacca cggacccgg cgcgctcttc   660 accgaccccgc ccggcgccct gctgcccttc ggcggccaca agggctacgc cctgggcctg   720
gtggccgaac tgctggccgg cgtcctgtcc ggcggcggca cgatccagcc ggaacacccc   780
cgcaacggcg tggccacgaa caacatgttc gcgctcctgc tggacccgca ggtggacttc   840
aacaccgact ggcgctccct ggaagtcggc gccttcatcg actacctgca cgcctgcaag   900
```

```
cccaacccg gcgtcgaatc ggtgcaatat cccggcgaat acgaagcccg caaccgcgcc      960
atcaacgcgg acaccgtgga attcgacacc cgcatctggg aaggcctgac cagactcgcc     1020
gtggacctgg gcgtcccgga agccctgccg cacgaaggc                            1059
```

<210> SEQ ID NO 3
<211> LENGTH: 325
<212> TYPE: PRT
<213> ORGANISM: Achromobacter denitrificans

<400> SEQUENCE: 3

```
Met Ser Gln Lys Pro Lys Ile Ile Val Ser Ala Pro Val Pro Ala Asp
1               5                   10                  15

Leu Arg Glu Arg Val Ala Ala Ala Cys Glu Ile Ile Asp Val Pro Val
            20                  25                  30

Gly Gln Asn Pro Ala Gln Ala Val Pro Glu Ala Gln Arg Ala Glu Val
        35                  40                  45

Ala Gly Met Val Cys Thr Val Arg Thr Arg Val Asp Gln Ala Leu Leu
    50                  55                  60

Asp Ala Phe Pro Ala Leu Ala Val Ser Ser Asn Phe Ala Val Gly Phe
65                  70                  75                  80

Asp Asn Val Asp Leu Asp Ala Ala Asn Arg Arg Gln Val Leu Ile Cys
                85                  90                  95

Asn Thr Pro Gly Val Leu Asp Gly Ala Val Ala Asp Val Thr Ile Gly
            100                 105                 110

Leu Met Leu Cys Leu Ala Arg Asn Leu Val Ala Gly Asp Ala Phe Val
        115                 120                 125

Arg Ser Gly Ala Trp Thr Lys Ser Ala Phe Pro Leu Thr Thr Asp Ile
    130                 135                 140

Arg Gly Lys Thr Leu Gly Leu Leu Gly Met Gly Arg Ile Gly Lys Val
145                 150                 155                 160

Val Ala Arg Thr Ala Gln Ala Phe Asp Met Lys Val Ile Tyr His Asn
                165                 170                 175

Arg Arg Glu Asp Arg Ser Val Gln Gly Leu Ala Ala Tyr Val Gly Arg
            180                 185                 190

Asp Glu Leu Phe Lys Phe Ser Asp Val Leu Ser Ile His Ile Pro Leu
        195                 200                 205

Ser Ala Glu Thr Arg His Ser Val Gly Lys Arg Glu Phe Glu Leu Met
    210                 215                 220

Lys Pro Thr Ala Tyr Val Ile Asn Thr Ala Arg Gly Pro Val Leu Asp
225                 230                 235                 240

Glu Ala Ala Leu Val Gln Ala Leu Arg Ser Gly Thr Ile Ala Gly Ala
                245                 250                 255

Gly Leu Asp Val Met Glu Gln Glu Pro Leu Pro Ser Ser Pro Leu
            260                 265                 270

Cys Glu Leu Pro Asn Val Leu Gln Ala His Val Gly Ser Ala Thr
        275                 280                 285

His Glu Thr Arg Arg Ala Met Ile Asp Leu Ala Val Ala Asn Leu Leu
    290                 295                 300

Asp Ala Leu Ala Gly Arg Lys Pro Gln Ala Met Val Asn Pro Gln Val
305                 310                 315                 320

Trp Glu Ala Arg Gly
            325
```

<210> SEQ ID NO 4

<211> LENGTH: 975
<212> TYPE: DNA
<213> ORGANISM: Achromobacter denitrificans

<400> SEQUENCE: 4

```
atgagccaaa aaccgaaaat catcgtatcc gcgccggtgc ccgccgatct gcgcgagcgc    60
gtggccgccg cctgtgaaat catcgacgtg cccgtggggc agaaccccgc gcaagccgtg   120
cccgaggcgc agcgcgccga agtcgctggc atggtctgca cggtgcgcac ccgcgtggac   180
caggcgttgc tcgacgcttt tcccgcgcta gccgtcagtt ccaatttcgc cgtgggattc   240
gacaacgtcg atctggacgc ggccaaccgc cgccaggtgc tcatctgcaa tacgcccggc   300
gtgctggacg gcgcggtcgc ggacgtgacc atcggcctga tgctgtgcct ggcccgcaac   360
ctggtggccg cgacgcgtt cgtgcgcagc ggcgcctgga ccaagagcgc gtttccactg   420
accacggaca tacgcggcaa gacgctgggc ctgctcggca tgggccgtat cggcaaggtg   480
gtggcgcgca cggcgcaggc tttcgacatg aaggtgatct atcacaaccg cgcgaggat   540
cggtcggtgc aaggtctggc cgcctacgtc gggcgcgacg agctgttcaa gttctcggac   600
gtgctgagca tccacatccc gctgtcggcc gagacgcgcc attccgtggg caagcgtgaa   660
ttcgagctga tgaagcctac ggcttatgtc atcaatacgg cgcgcggccc ggtgctggac   720
gaggcggcgc tggtccaggc gctgcgcagc ggcacgatcg ccggcgccgg cctggacgtg   780
atggagcagg agccgctgcc gccgtccagc cccttgtgcg agctgcccaa cgtggtgttg   840
caggcgcacg tgggcagcgc cacccacgag acgcggcgcg ccatgatcga cctggcggtg   900
gccaacctgc tggacgcgct ggccgggcgc aagccgcagg ccatggtcaa cccgcaggtg   960
tgggaagccc gcggc                                                    975
```

<210> SEQ ID NO 5
<211> LENGTH: 325
<212> TYPE: PRT
<213> ORGANISM: Achromobacter denitrificans

<400> SEQUENCE: 5

```
Met Ser Gln Lys Pro Lys Ile Ile Val Ser Ala Pro Val Pro Ala Asp
1               5                   10                  15

Leu Arg Glu Arg Val Ala Ala Ala Cys Glu Ile Ile Asp Val Pro Val
            20                  25                  30

Gly Gln Asn Pro Ala Gln Ala Val Pro Glu Ala Gln Arg Ala Glu Val
        35                  40                  45

Ala Gly Met Val Cys Thr Val Arg Thr Arg Val Asp Gln Ala Leu Leu
    50                  55                  60

Asp Ala Phe Pro Ala Leu Ala Val Ser Ser Asn Phe Ala Val Gly Phe
65                  70                  75                  80

Asp Asn Val Asp Leu Asp Ala Ala Asn Arg Arg Gln Val Leu Ile Cys
                85                  90                  95

Asn Thr Pro Gly Val Leu Asp Gly Ala Val Ala Asp Ile Thr Ile Gly
            100                 105                 110

Leu Met Leu Cys Leu Ala Arg Asn Leu Val Ala Gly Asp Ala Phe Val
        115                 120                 125

Arg Ser Gly Ala Trp Thr Lys Ser Ala Phe Pro Leu Thr Thr Asp Ile
    130                 135                 140

Arg Gly Lys Thr Leu Gly Leu Leu Gly Met Gly Arg Ile Gly Lys Val
145                 150                 155                 160

Val Ala Arg Thr Ala Gln Ala Phe Asp Met Lys Val Ile Tyr His Asn
```

```
                165                 170                 175
Arg Arg Glu Asp Arg Ser Val Gln Gly Leu Ala Ala Tyr Val Asp Arg
            180                 185                 190

Asp Glu Leu Phe Lys Phe Ser Asp Val Leu Ser Ile His Ile Pro Leu
        195                 200                 205

Ser Ala Glu Thr Arg His Ser Val Gly Lys Arg Glu Phe Glu Leu Met
    210                 215                 220

Lys Pro Thr Ala Tyr Val Ile Asn Thr Ala Arg Gly Pro Val Leu Asp
225                 230                 235                 240

Glu Ala Ala Leu Val Arg Ala Leu Arg Ser Gly Thr Ile Ala Gly Ala
                245                 250                 255

Gly Leu Asp Val Met Glu Gln Glu Pro Leu Pro Ser Ser Pro Leu
            260                 265                 270

Cys Glu Leu Pro Asn Val Val Leu Gln Ala His Val Gly Ser Ala Thr
        275                 280                 285

His Glu Thr Arg Arg Ala Met Ile Asp Leu Ala Val Ala Asn Leu Leu
    290                 295                 300

Asp Ala Leu Ala Gly Arg Lys Pro Gln Ala Met Val Asn Pro Gln Val
305                 310                 315                 320

Trp Glu Ala Arg Gly
                325
```

<210> SEQ ID NO 6
<211> LENGTH: 978
<212> TYPE: DNA
<213> ORGANISM: Achromobacter denitrificans

<400> SEQUENCE: 6

| | |
|---|---|
| atgtctcaaa aaccaaaaat catcgttagc gcaccagttc cggccgatct gcgcgaacgt | 60 |
| gttgcagcgg cctgcgaaat tatcgatgtg cctgttggtc agaatccggc gcaggcggtt | 120 |
| ccagaggcgc agcgtgcgga agtagccggt atggtatgta ctgtacgtac gcgtgtggat | 180 |
| caggctctgc tggatgcgtt cccggccctg gccgtttcca gcaacttcgc ggtgggtttt | 240 |
| gacaacgtgg acctggacgc ggcgaaccgt cgccaggtac tgatttgcaa caccccctggc | 300 |
| gttctggacg gcgctgttgc tgatattacc atcggcctga tgctgtgcct ggctcgtaac | 360 |
| ctggtggcag gtgacgcttt cgttcgcagc ggtgcttgga ccaaatccgc ctttccgctg | 420 |
| accaccgaca tccgtggtaa aaccctgggc ctgctgggca tgggccgcat cggcaaagtc | 480 |
| gtcgcacgca ccgcgcaggc tttcgatatg aaggtgatct accataaccg tcgtgaagat | 540 |
| cgctctgtac agggcctggc ggcatacgtc gatcgtgacg agctgttcaa attcagcgac | 600 |
| gtcctgtcta tccacatccc gctgtctgct gaaacgcgcc actccgtagg caaacgtgag | 660 |
| tttgaactga tgaagccgac cgcgtatgtt attaacactg cgcgtggtcc ggttctggat | 720 |
| gaagcagcac tggtacgggc actgcgctct ggtacgattg ctggtgctgg tctggacgtg | 780 |
| atggaacagg aaccgctgcc gccgtcttcc ccgctgtgtg agctgccgaa tgtcgtgctg | 840 |
| caagctcacg tgggttccgc gactcacgaa actcgtcgtg ctatgattga tctggcggtt | 900 |
| gctaacctgc tggacgcact ggcaggccgt aaaccgcagg caatggttaa cccgcaggtg | 960 |
| tgggaagccc gtggctaa | 978 |

<210> SEQ ID NO 7
<211> LENGTH: 364
<212> TYPE: PRT
<213> ORGANISM: Bacillus sphaericus

<400> SEQUENCE: 7

Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
            20                  25                  30

Asp Thr Thr Leu Gly Pro Ala Leu Gly Gly Ala Arg Met Trp Thr Tyr
        35                  40                  45

Ala Thr Glu Glu Asn Ala Ile Glu Asp Ala Leu Arg Leu Ala Arg Gly
    50                  55                  60

Met Thr Tyr Lys Asn Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
            100                 105                 110

Gly Glu Asp Val Gly Thr Thr Val Thr Asp Met Asp Leu Ile His Glu
        115                 120                 125

Glu Thr Asn Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
210                 215                 220

Glu Ile Tyr Ser Gln Glu Val Asp Ile Phe Ser Pro Cys Ala Leu Gly
225                 230                 235                 240

Ala Ile Leu Asn Asp Glu Thr Ile Pro Gln Leu Lys Ala Lys Val Ile
                245                 250                 255

Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335

Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
        355                 360

<210> SEQ ID NO 8
<211> LENGTH: 1095
<212> TYPE: DNA
<213> ORGANISM: Bacillus sphaericus

<400> SEQUENCE: 8

```
atggaaatct tcaagtatat ggaaaagtat gattatgaac aattggtatt ttgccaagac      60
gaagcatctg ggttaaaagc gattatcgct atccatgaca caacacttgg accagcatta     120
ggtggtgctc gtatgtggac ctacgcgaca gaagaaaatg cgattgagga tgcattaaga     180
ttagcacgcg ggatgacata taaaaatgca gctgctggtt taaaccttgg cggtggaaaa     240
acggtcatta ttggggaccc atttaaagat aaaaacgaag aaatgttccg tgctttaggt     300
cgtttcattc aaggattaaa cggtcgctat attaccggtg aagatgttgg tacaaccgta     360
acagatatgg atttaatcca tgaggaaaca aattacgtta caggtatatc gccagcgttt     420
ggttcatcgg gtaatccttc accagtaact gcttatggcg tttatcgtgg catgaaagca     480
gcggcgaaag aagcatttgg tacggatatg ctagaaggtc gtactatatc ggtacaaggg     540
ctaggaaacg tagcttacaa gctttgcgag tatttacata tgaaggtgc aaaacttgta      600 gtaacagata ttaaccaagc ggctattgat cgtgttgtca atgattttgg cgctacagca     660
gttgcacctg atgaaatcta ttcacaagaa gtcgatattt tctcaccgtg tgcacttggc     720
gcaattttaa atgacgaaac gattccgcaa ttaaaagcaa agttattgc tggttctgct      780 aataaccaac tacaagattc acgacatgga gattatttac acgagctagg cattgtttat     840
gcacctgact atgtcattaa tgcaggtggt gtaataaatg tcgcggacga attatatggc     900
tataatcgtg aacgagcgtt gaaacgtgta gatggtattt acgatagtat tgaaaaaatc     960
tttgaaattt ccaaacgtga tagtattcca acatatgttg cggcaaatcg tttggcagaa    1020
gaacgtattg ctcgtgtagc gaaatcgcgt agtcagttct aaaaaatga aaaaatatt     1080 ttgaacggcc gttaa                                                     1095

<210> SEQ ID NO 9
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 9
ccatatgaaa aagctctcca tcgcccaag                                        29

<210> SEQ ID NO 10
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 10
actcgaggcc ttcgtgcggc agggcttc                                         28

<210> SEQ ID NO 11
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 11
ccatatgagc caaaaaccga aaatcatcg                                        29

<210> SEQ ID NO 12
<211> LENGTH: 32
<212> TYPE: DNA
```

-continued

```
<213> ORGANISM: Artificial Sequence
<220> FEATURE:
<223> OTHER INFORMATION: Designed oligonucleotide primer for PCR

<400> SEQUENCE: 12
actcgaggcc gcgggcttcc cacacctgcg gg                                    32

<210> SEQ ID NO 13
<211> LENGTH: 978
<212> TYPE: DNA
<213> ORGANISM: Artificial Sequence
<220> FEATURE:
<223> OTHER INFORMATION: Polynucleotide encoding Dehydrogenase

<400> SEQUENCE: 13
atgtctcaaa aaccaaaaat catcgttagc gcaccagttc cggccgatct gcgcgaacgt       60
gttgcagcgg cctgcgaaat tatcgatgtg cctgttggtc agaatccggc gcaggcggtt      120
ccagaggcgc agcgtgcgga agtagccggt atggtatgta ctgtacgtac gcgtgtggat      180
caggctctgc tggatgcgtt cccggccctg ccgtttccag caacttcgc ggtgggtttt      240 gacaacgtgg acctggacgc ggcgaaccgt cgccaggtac tgatttgcaa caccctggc      300 gttctggacg gcgctgttgc tgatgttacc atcggcctga tgctgtgcct ggctcgtaac      360
ctggtggcag gtgacgcttt cgttcgcagc ggtgcttgga ccaaatccgc ctttccgctg      420
accaccgaca tccgtggtaa aaccctgggc ctgctgggca tgggccgcat cggcaaagtc      480
gtcgcacgca ccgcgcaggc tttcgatatg aaggtgatct accataaccg tcgtgaagat      540
cgctctgtac agggcctggc ggcatacgtc ggtcgtgacg agctgttcaa attcagcgac      600
gtcctgtcta ccacatcc gctgtctgct gaaacgcgcc actccgtagg caaacgtgag      660
tttgaactga tgaagccgac cgcgtatgtt attaacactg cgcgtggtcc ggttctggat      720
gaagcagcac tggtacaggc actgcgctct ggtacgattg ctggtgctgg tctggacgtg      780
atggaacagg aaccgctgcc gccgtcttcc ccgctgtgtg agctgccgaa tgtcgtgctg      840
caagctcacg tgggttccgc gactcacgaa actcgtcgtg ctatgattga tctggcggtt      900
gctaacctgc tggacgcact ggcaggccgt aaaccgcagg caatggttaa cccgcaggtg      960
tgggaagccc gtggctaa                                                    978

<210> SEQ ID NO 14
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 14
gccatggaaa tcttcaagta tatgg                                             25

<210> SEQ ID NO 15
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 15
gggcccgggt taacggccgt tcaaaatatt                                        30

<210> SEQ ID NO 16
<211> LENGTH: 27
```

```
<212> TYPE: DNA
<213> ORGANISM: Artificial Sequence
<220> FEATURE:
<223> OTHER INFORMATION: Designed oligonucleotide primer for PCR

<400> SEQUENCE: 16
gtcgctatat taccggtgaa gatgttg                                           27

<210> SEQ ID NO 17
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 17
caacatcttc accggtaata tagcgac                                           27

<210> SEQ ID NO 18
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 18
gatagtattc caacctatgt tgcggc                                            26

<210> SEQ ID NO 19
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 19
gccgcaacat aggttggaat actatc                                            26

<210> SEQ ID NO 20
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 20
gggcatatgg aaatcttcaa gtatatgg                                          28

<210> SEQ ID NO 21
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 21
ggatccttaa cggccgttca aaatatt                                           27

<210> SEQ ID NO 22
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 22
```
cgtagcttac aaactttgcg agtatttac                                29

<210> SEQ ID NO 23
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 23
gtaaatactc gcaaagtttg taagctacg                                29

<210> SEQ ID NO 24
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 24
ccatggctat gaaaaagctc tccatcgccc                               30

<210> SEQ ID NO 25
<211> LENGTH: 32
<212> TYPE: DNA
<213> ORGANISM: Artificial Sequence
<220> FEATURE:
<223> OTHER INFORMATION: Designed oligonucleotide primer for PCR

<400> SEQUENCE: 25
caagcttgct agccttcgtg cggcagggct tc                            32

<210> SEQ ID NO 26
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 26
cggatccgag gaaacagacc atgg                                     24

<210> SEQ ID NO 27
<211> LENGTH: 32
<212> TYPE: DNA
<213> ORGANISM: Artificial Sequence
<220> FEATURE:
<223> OTHER INFORMATION: Designed oligonucleotide primer for PCR

<400> SEQUENCE: 27
gctgcagcct agccttcgtg cggcagggct tc                            32

<210> SEQ ID NO 28
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 28
gctgcagcag gaaacagacc atgg                                     24

<210> SEQ ID NO 29
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 29
caagcttgtt agccacgggc ttcccacacc                                           30

<210> SEQ ID NO 30
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 30
ccatatgtct caaaaaccaa aaatcatcg                                            29

<210> SEQ ID NO 31
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 31
actcgaggcc acgggcttcc cacacctgcg                                           30

<210> SEQ ID NO 32
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 32
gccatggcta tgtctcaaaa accaaaaatc                                           30

<210> SEQ ID NO 33
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 33
ggatcctcag tggtggtggt ggtggtg                                              27

<210> SEQ ID NO 34
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 34
cgctgttgct gatattacca tcggcctg                                             28

<210> SEQ ID NO 35
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 35
caggccgatg gtaatatcag caacagcg                                             28

<210> SEQ ID NO 36
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 36
ggcggcatac gtcgatcgtg acgagctg                                    28

<210> SEQ ID NO 37
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 37
cagctcgtca cgatcgacgt atgccgcc                                    28

<210> SEQ ID NO 38
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 38
gcagcactgg tacgggcact gcgctctg                                    28

<210> SEQ ID NO 39
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 39
cagagcgcag tgcccgtacc agtgctgc                                    28

<210> SEQ ID NO 40
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 40
gctgcagctc agtggtggtg gtggtggtg                                   29

<210> SEQ ID NO 41
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 41
caagcttgtc agtggtggtg gtggtggtg                                   29

<210> SEQ ID NO 42
<211> LENGTH: 364
<212> TYPE: PRT
<213> ORGANISM: Bacillus sphaericus

<400> SEQUENCE: 42

Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
            20                  25                  30

Asp Thr Thr Leu Gly Pro Ala Leu Gly Gly Ala Arg Met Trp Thr Tyr
        35                  40                  45

Ala Thr Glu Glu Asn Ala Ile Glu Asp Ala Leu Arg Leu Ala Arg Gly
    50                  55                  60

Met Thr Tyr Lys Asn Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
                100                 105                 110

Ala Glu Asp Val Gly Thr Thr Val Thr Asp Met Asp Leu Ile His Glu
            115                 120                 125

Glu Thr Asn Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
210                 215                 220

Glu Ile Tyr Ser Gln Glu Val Asp Ile Phe Ser Pro Cys Ala Leu Gly
225                 230                 235                 240

Ala Ile Leu Asn Asp Glu Thr Ile Pro Gln Leu Lys Ala Lys Val Ile
                245                 250                 255

Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335

Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
            355                 360

<210> SEQ ID NO 43
<211> LENGTH: 1095
<212> TYPE: DNA
<213> ORGANISM: Bacillus sphaericus

<400> SEQUENCE: 43
atggaaatct tcaagtatat ggaaaagtat gattatgaac aattggtatt ttgccaagac    60

-continued

```
gaagcatctg ggttaaaagc gattatcgct atccatgaca caacacttgg accagcatta      120
ggtggtgctc gtatgtggac ctacgcgaca gaagaaaatg cgattgagga tgcattaaga      180
ttagcacgcg ggatgacata taaaaatgca gctgctggtt taaaccttgg cggtggaaaa      240
acggtcatta ttggggaccc atttaaagat aaaaacgaag aaatgttccg tgctttaggt      300
cgtttcattc aaggattaaa cggtcgctat attaccgctg aagatgttgg tacaaccgta      360
acagatatgg atttaatcca tgaggaaaca aattacgtta caggtatatc gccagcgttt      420
ggttcatcgg gtaatccttc accagtaact gcttatggcg tttatcgtgg catgaaagca      480
gcggcgaaag aagcatttgg tacggatatg ctagaaggtc gtactatatc ggtacaaggg      540
ctaggaaacg tagcttacaa gctttgcgag tatttacata atgaaggtgc aaaacttgta      600
gtaacagata ttaaccaagc ggctattgat cgtgttgtca atgattttgg cgctacagca      660
gttgcacctg atgaaatcta ttcacaagaa gtcgatattt tctcaccgtg tgcacttggc      720
gcaattttaa atgacgaaac gattccgcaa ttaaaagcaa aagttattgc tggttctgct      780
aataaccaac tacaagattc acgacatgga gattatttac acgagctagg cattgtttat      840
gcacctgact atgtcattaa tgcaggtggt gtaataaatg tcgcggacga attatatggc      900
tataatcgtg aacgagcgtt gaaacgtgta gatggtattt acgatagtat tgaaaaaatc      960
tttgaaattt ccaaacgtga tagtattcca acatatgttg cggcaaatcg tttggcagaa     1020
gaacgtattg ctcgtgtagc gaaatcgcgt agtcagttct taaaaatgaa aaaaatatt      1080 ttgaacggcc gttaa                                                      1095

<210> SEQ ID NO 44
<211> LENGTH: 20
<212> TYPE: PRT
<213> ORGANISM: Artificial Sequence
<220> FEATURE:
<223> OTHER INFORMATION: Designed amino acid sequence

<400> SEQUENCE: 44

Met Gly Ser Ser His His His His His His Ser Ser Gly Leu Val Pro
1               5                   10                  15

Arg Gly Ser His
            20

<210> SEQ ID NO 45
<211> LENGTH: 8
<212> TYPE: PRT
<213> ORGANISM: Artificial Sequence
<220> FEATURE:
<223> OTHER INFORMATION: Designed amino acid sequence

<400> SEQUENCE: 45

Leu Glu His His His His His His
1               5
```